US011690960B2

(12) United States Patent
Shetty et al.

(10) Patent No.: US 11,690,960 B2
(45) Date of Patent: Jul. 4, 2023

(54) VARIABLE DOSING SYRINGE

(71) Applicant: Congruence Medical Solutions, LLC, Hanover, MD (US)

(72) Inventors: Gautam Nithyanand Shetty, Hanover, MD (US); Lou Castagna, Middletown, PA (US)

(73) Assignee: Congruence Medical Solutions, LLC, Hanover, MD (US)

( * ) Notice: Subject to any disclaimer, the term of this patent is extended or adjusted under 35 U.S.C. 154(b) by 220 days.

(21) Appl. No.: 17/098,276

(22) Filed: Nov. 13, 2020

(65) Prior Publication Data

US 2021/0146058 A1 May 20, 2021

Related U.S. Application Data

(60) Provisional application No. 62/935,193, filed on Nov. 14, 2019.

(51) Int. Cl.
*A61M 5/315* (2006.01)
*A61M 5/32* (2006.01)

(52) U.S. Cl.
CPC ...... *A61M 5/31551* (2013.01); *A61M 5/3157* (2013.01); *A61M 5/3234* (2013.01); *A61M 2205/581* (2013.01)

(58) Field of Classification Search
CPC ............ A61M 5/31551; A61M 5/3157; A61M 5/3234; A61M 5/3146; A61M 5/3155;
(Continued)

(56) References Cited

U.S. PATENT DOCUMENTS 3,122,280 A 2/1964 Goda
3,770,026 A 11/1973 Isenberg
(Continued)

FOREIGN PATENT DOCUMENTS

CN 101932350 A 12/2010
EA 201590139 A1 7/2015
(Continued)

OTHER PUBLICATIONS

Notification of Reasons for Refusal dated Sep. 14, 2021, directed to JP Application No. 2019-505122; 16 pages.
(Continued)

*Primary Examiner* — Tasnim Mehjabin Ahmed
(74) *Attorney, Agent, or Firm* — Morrison & Foerster LLP

(57) ABSTRACT

A syringe includes a dosage setter operatively coupled to a plunger rod and comprising a rotatable body that comprises a set of one or more stops for engaging the set of one or more protrusions of the plunger rod depending on at least a rotational position of the set of one or more stops relative to the set of one or more protrusions, wherein a first rotational adjustment associated with the dosage setter is configured to set a first dosage increment by adjusting a relative axial position between the rotatable body and the plunger rod, and a second rotational adjustment associated with the dosage setting assembly is configured to set a second dosage increment that is larger than the first dosage increment by adjusting a relative rotational alignment between the set of one or more stops and the set of one or more protrusions.

38 Claims, 43 Drawing Sheets

(58) Field of Classification Search
CPC ............ A61M 5/3153; A61M 5/31556; A61M 5/3156; A61M 5/31573; A61M 5/3158; A61M 5/31591; A61M 5/3216; A61M 5/31511; A61M 2205/581; A61M 2005/3217
See application file for complete search history.

(56) References Cited

U.S. PATENT DOCUMENTS

| | | | |
|---|---|---|---|
| 4,073,321 | A | 2/1978 | Moskowitz |
| 4,244,366 | A | 1/1981 | Raines |
| 4,563,178 | A | 1/1986 | Santeramo |
| 4,921,487 | A | 5/1990 | Buffet et al. |
| 4,929,238 | A | 5/1990 | Baum |
| 5,104,380 | A | 4/1992 | Holman et al. |
| 5,318,544 | A | 6/1994 | Drypen et al. |
| 5,782,633 | A | 7/1998 | Muhlbauer |
| 5,951,526 | A | 9/1999 | Korisch et al. |
| 7,678,084 | B2 | 3/2010 | Judson |
| 8,535,277 | B2 | 9/2013 | Oden et al. |
| 8,915,889 | B2 | 12/2014 | Cox et al. |
| 9,956,351 | B2 | 5/2018 | Møller |
| 2004/0162528 | A1 | 8/2004 | Horvath et al. |
| 2005/0165363 | A1 | 7/2005 | Judson |
| 2005/0215957 | A1 | 9/2005 | Hynes |
| 2006/0217670 | A1* | 9/2006 | Cecchi ............ A61M 5/19 604/209 |
| 2007/0073224 | A1 | 3/2007 | Dries |
| 2012/0041366 | A1 | 2/2012 | Fayyaz et al. |
| 2012/0053516 | A1 | 3/2012 | Cronenberg et al. |
| 2012/0172815 | A1* | 7/2012 | Holmqvist ........ A61M 5/31555 604/208 |
| 2013/0204193 | A1 | 8/2013 | Holmqvist |
| 2013/0267908 | A1 | 10/2013 | Leak |
| 2014/0012227 | A1 | 1/2014 | Sigg |
| 2018/0056009 | A1 | 3/2018 | Filman et al. |
| 2018/0126085 | A1 | 5/2018 | Bowman et al. |
| 2018/0200446 | A1 | 7/2018 | Grimoldby et al. |
| 2021/0146058 | A1 | 5/2021 | Shetty |
| 2021/0178080 | A1 | 6/2021 | Shetty et al. |

FOREIGN PATENT DOCUMENTS

| | | | |
|---|---|---|---|
| EP | 0058536 | A1 | 8/1982 |
| EP | 0584531 | A2 | 3/1994 |
| EP | 0800798 | A1 | 10/1997 |
| JP | 2005520646 | A | 7/2005 |
| JP | 2015-131114 | A | 7/2015 |
| RU | 2011127107 | A | 1/2013 |
| TW | 201315502 | A1 | 4/2013 |
| WO | 03/080160 | A1 | 10/2003 |
| WO | 2008/101829 | A1 | 8/2008 |
| WO | 2009/154803 | A2 | 3/2010 |
| WO | 2010/063687 | A1 | 6/2010 |
| WO | 2011/088894 | A1 | 7/2011 |
| WO | 2014/005728 | A1 | 1/2014 |
| WO | 2015/052704 | A1 | 4/2015 |
| WO | 2017/180480 | A1 | 10/2017 |
| WO | 2018/141633 | A1 | 8/2018 |
| WO | 2018/141634 | A1 | 8/2018 |

OTHER PUBLICATIONS

Office Action dated Oct. 29, 2021, directed to KR Application No. 10-2018-7031807; 7 pages.
Extended European Search Report dated Mar. 9, 2021, directed to EP Application No. 21152295; 10 pages.
Extended European Search Report, dated Sep. 20, 2019, for European Patent Application No. 17782891.0, 9 pages.
International Preliminary Report on Patentability received for PCT Patent Application No. PCT/US2017/026684, dated Oct. 16, 2018, 7 pages.
International Search Report and Written Opinion received for PCT Patent Application No. PCT/US2017/026684, dated Jun. 19, 2017, 9 pages.
Invitation to Pay Additional Fees dated Mar. 9, 2021, directed to International Application No. PCT/US2020/060589; 14 pages.
Notification of Reasons for Refusal dated Feb. 2, 2021, directed to JP Application No. 2019-505122; 19 pages.
Notification of the First Office Action dated Sep. 25, 2020, directed to CN Application No. 201780023860.9; 24 pages.
Notification of the Second Office Action dated Mar. 17, 2021, directed to CN Application No. 201780023860.9; 6 pages.
Official Action dated Jul. 24, 2020, directed to RU Application No. 2018139650; 24 pages.
Examination Report dated Jun. 30, 2021, directed to IN Application No. 201817038141; 5 pages.
International Search Report and Written Opinion dated Jun. 17, 2021, directed to International Application No. PCT/US2020/060589; 24 pages.
Office Action dated May 4, 2021, directed to TW Application No. 106112496; 14 pages.

* cited by examiner

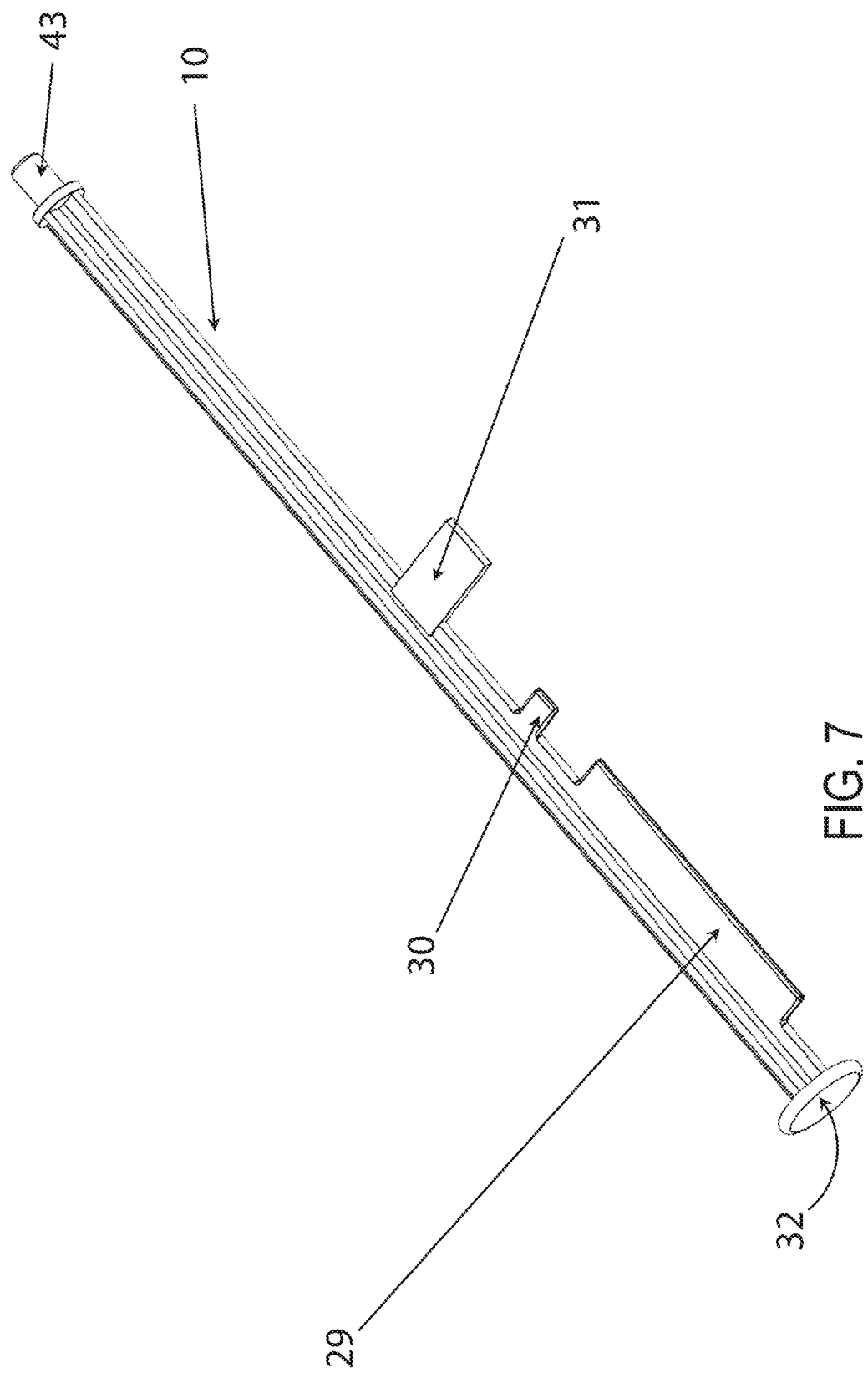

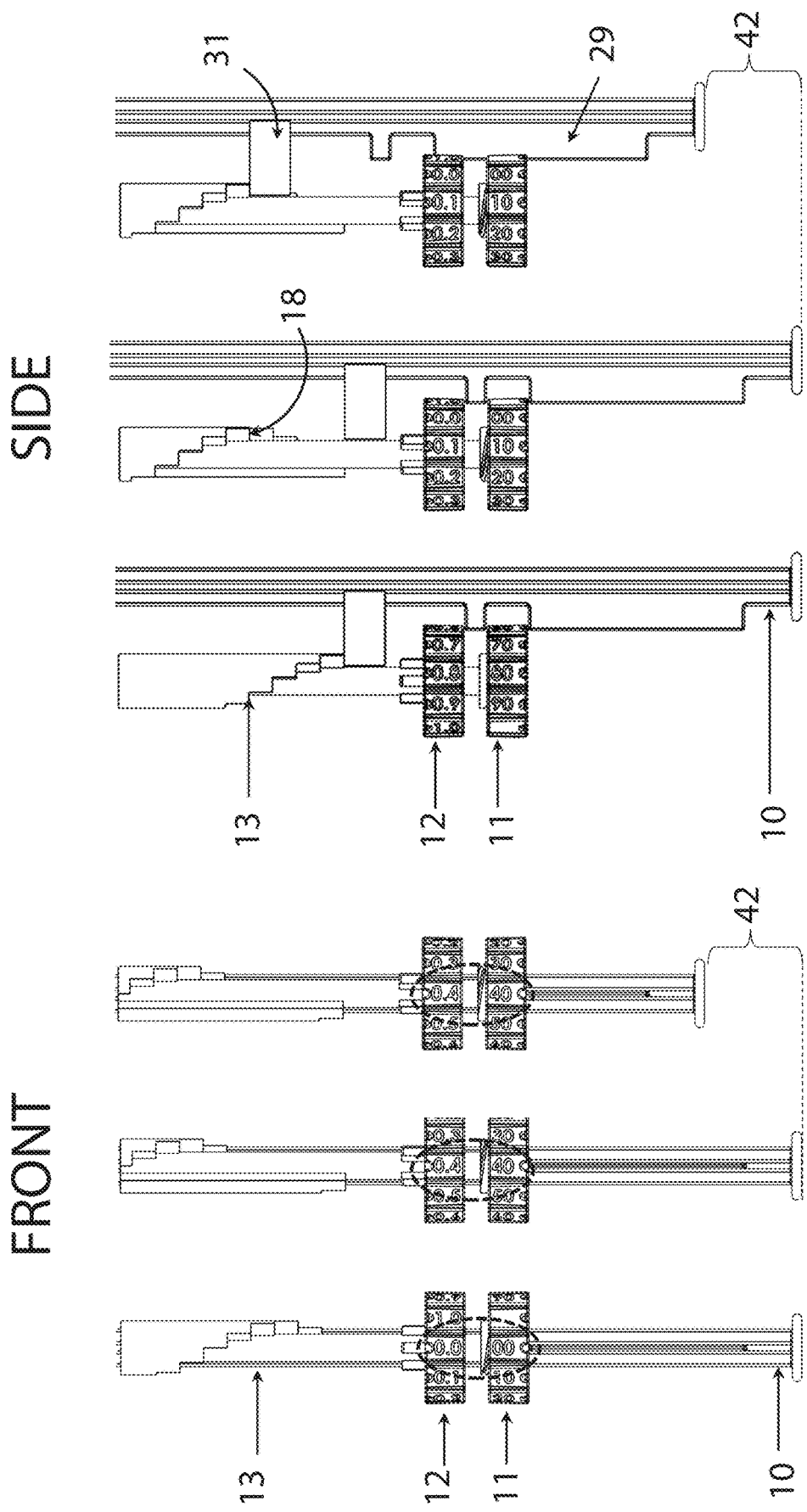

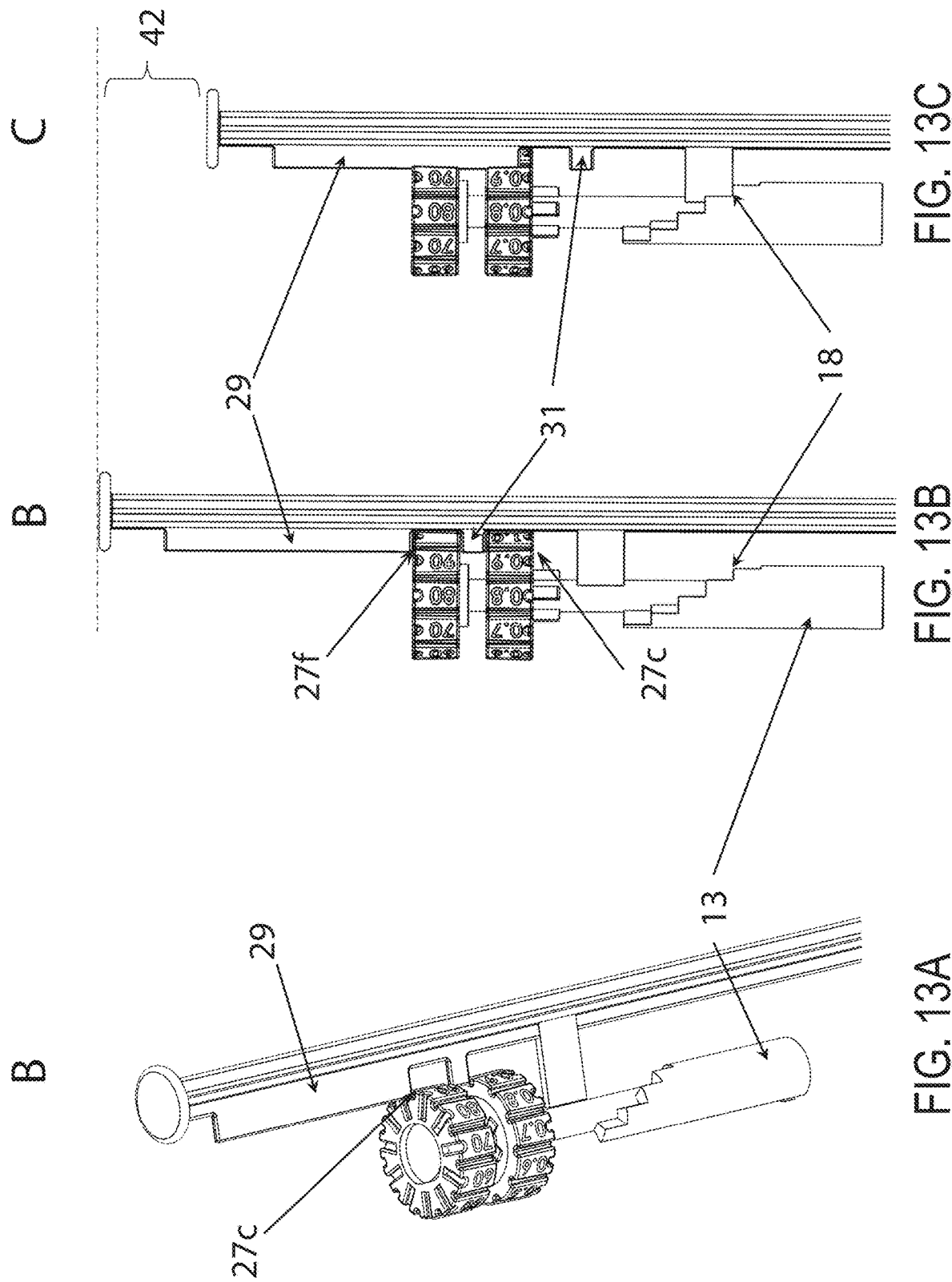

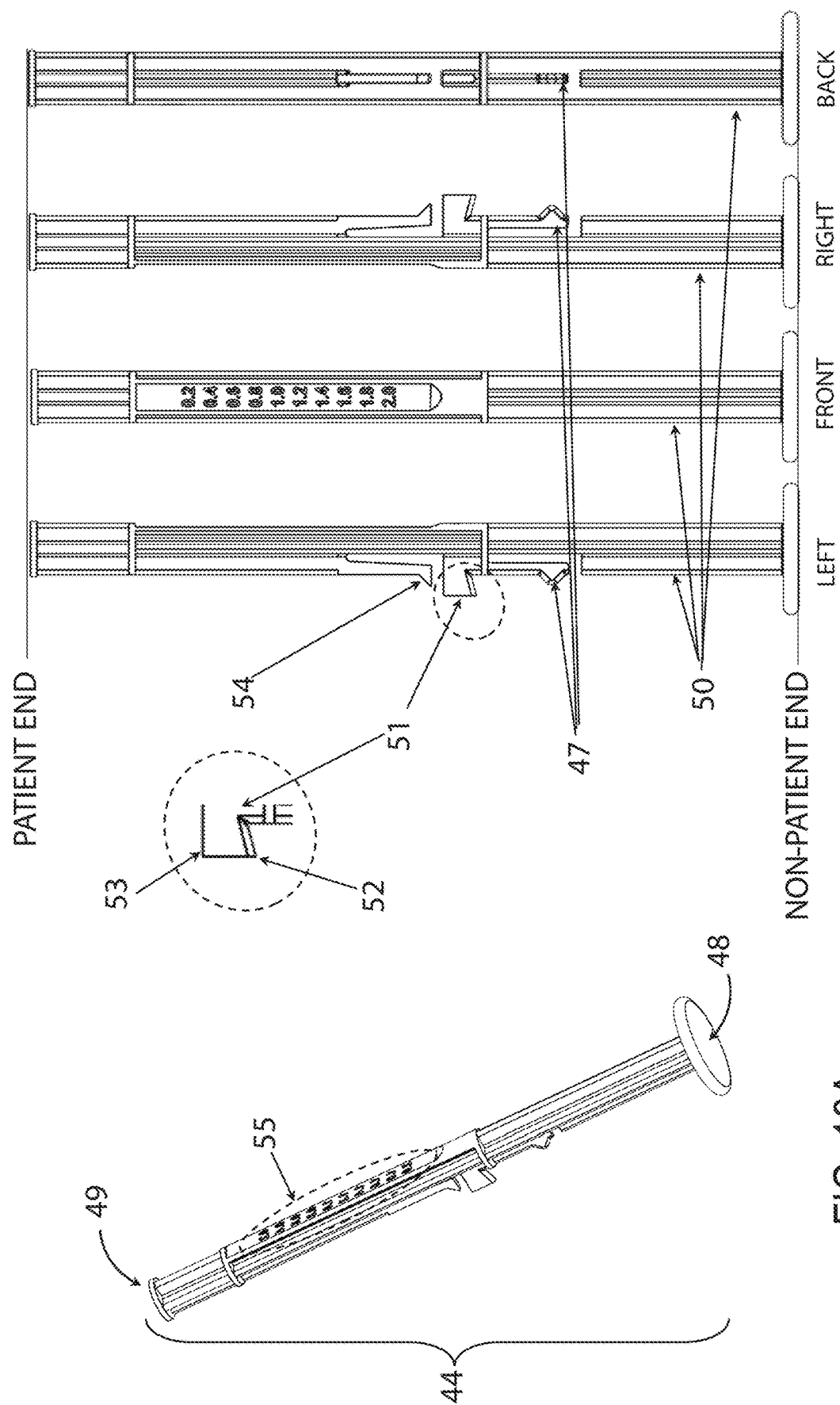

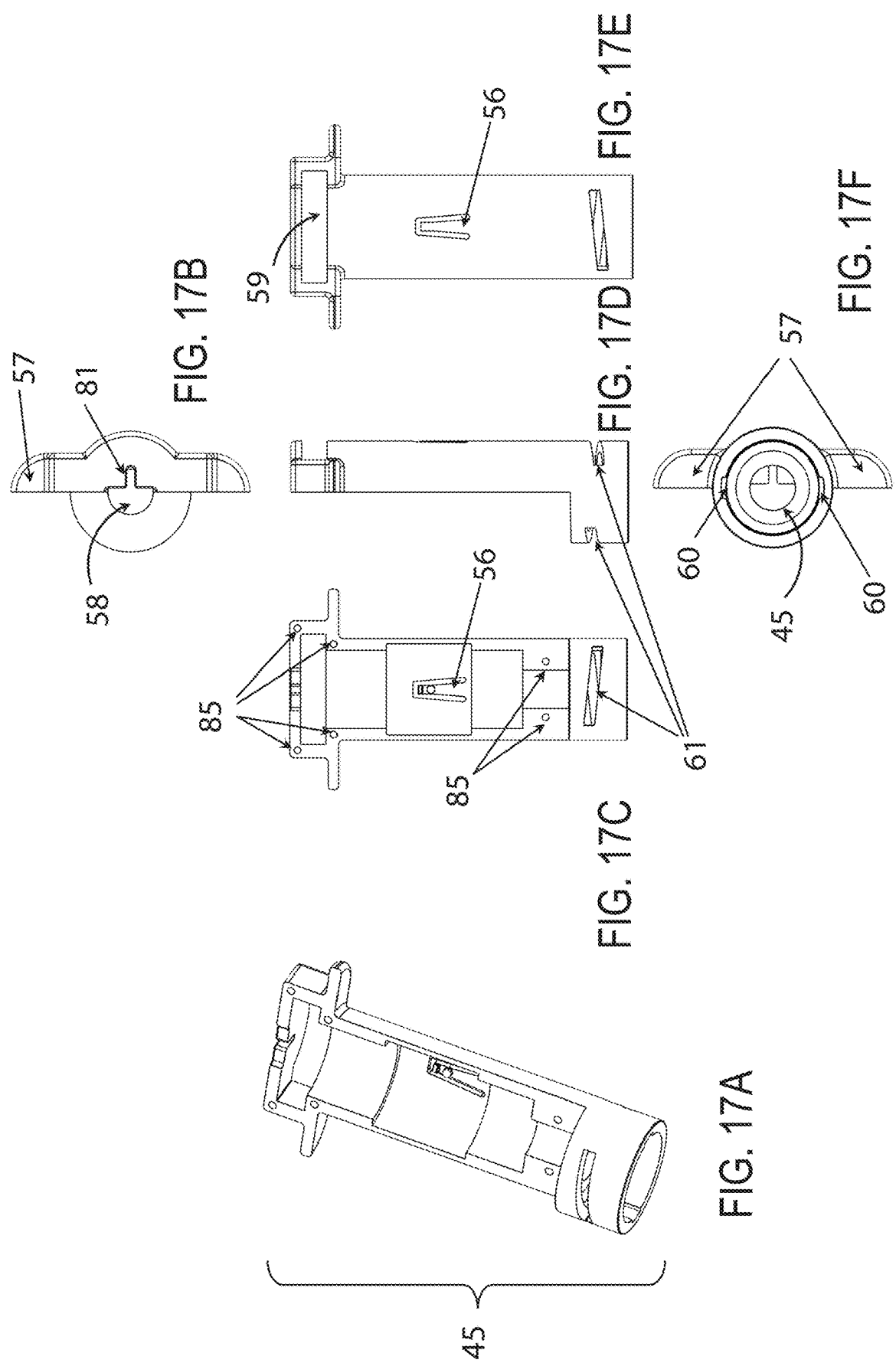

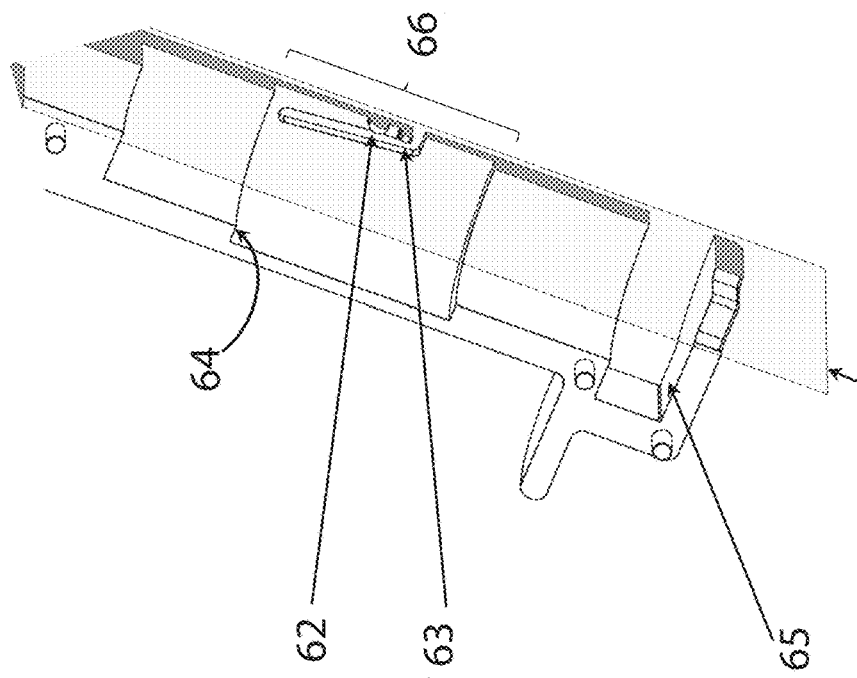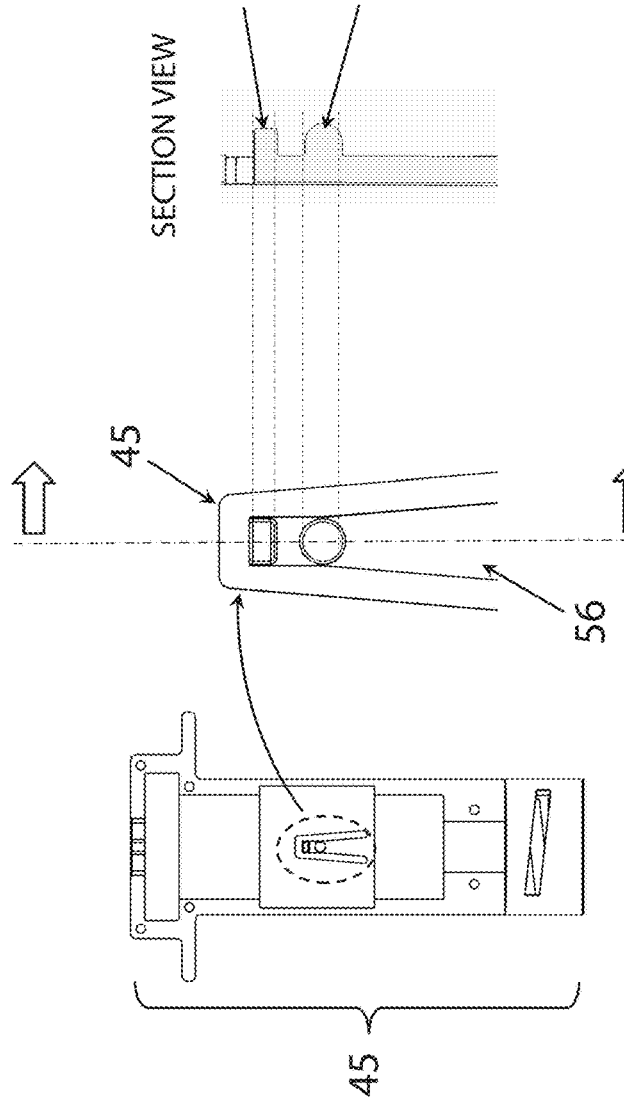
FIG. 18A  FIG. 18B  FIG. 18C  FIG. 18D

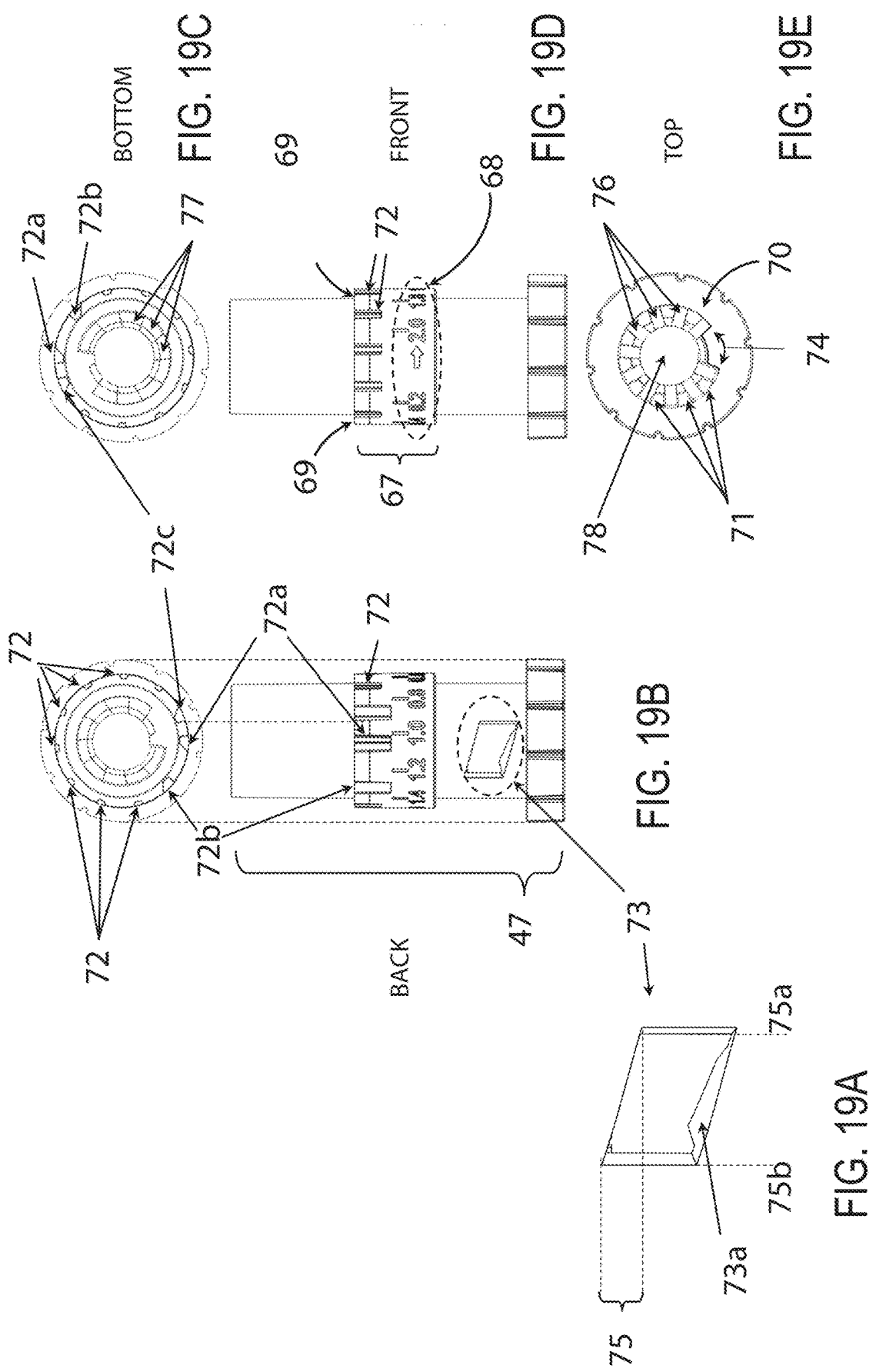

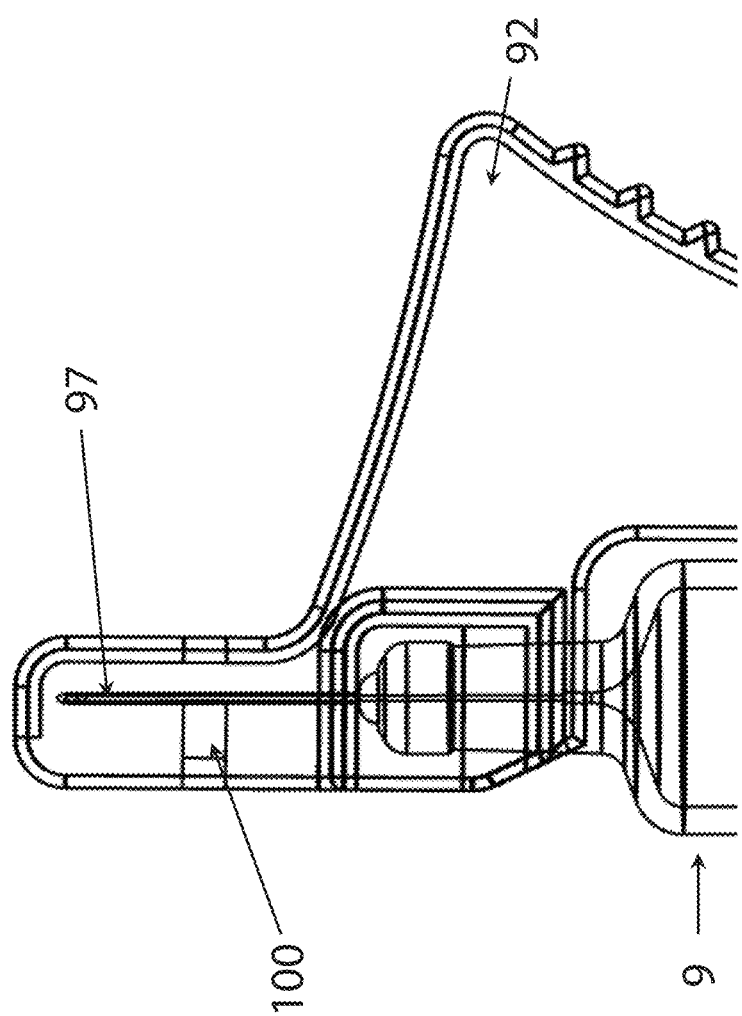

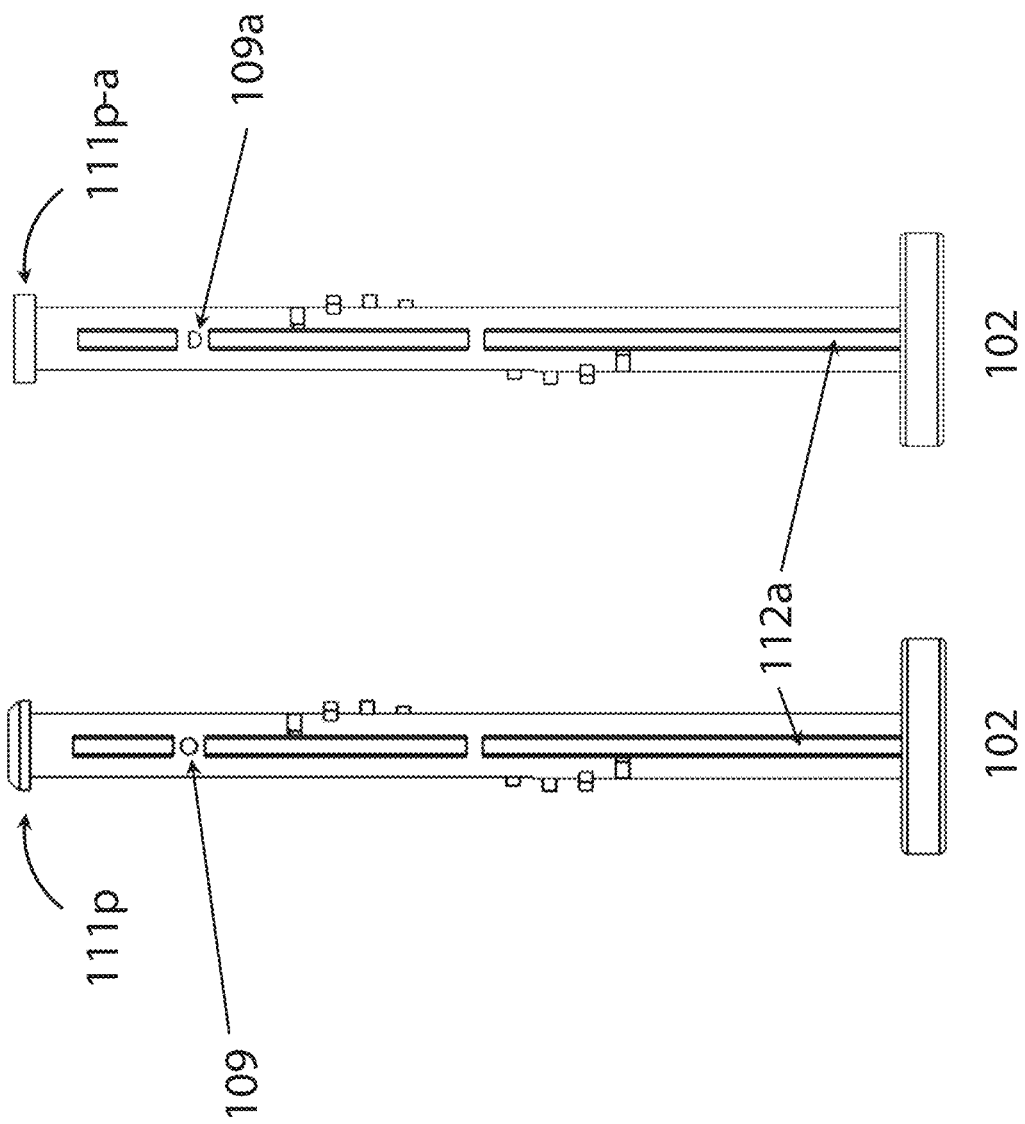

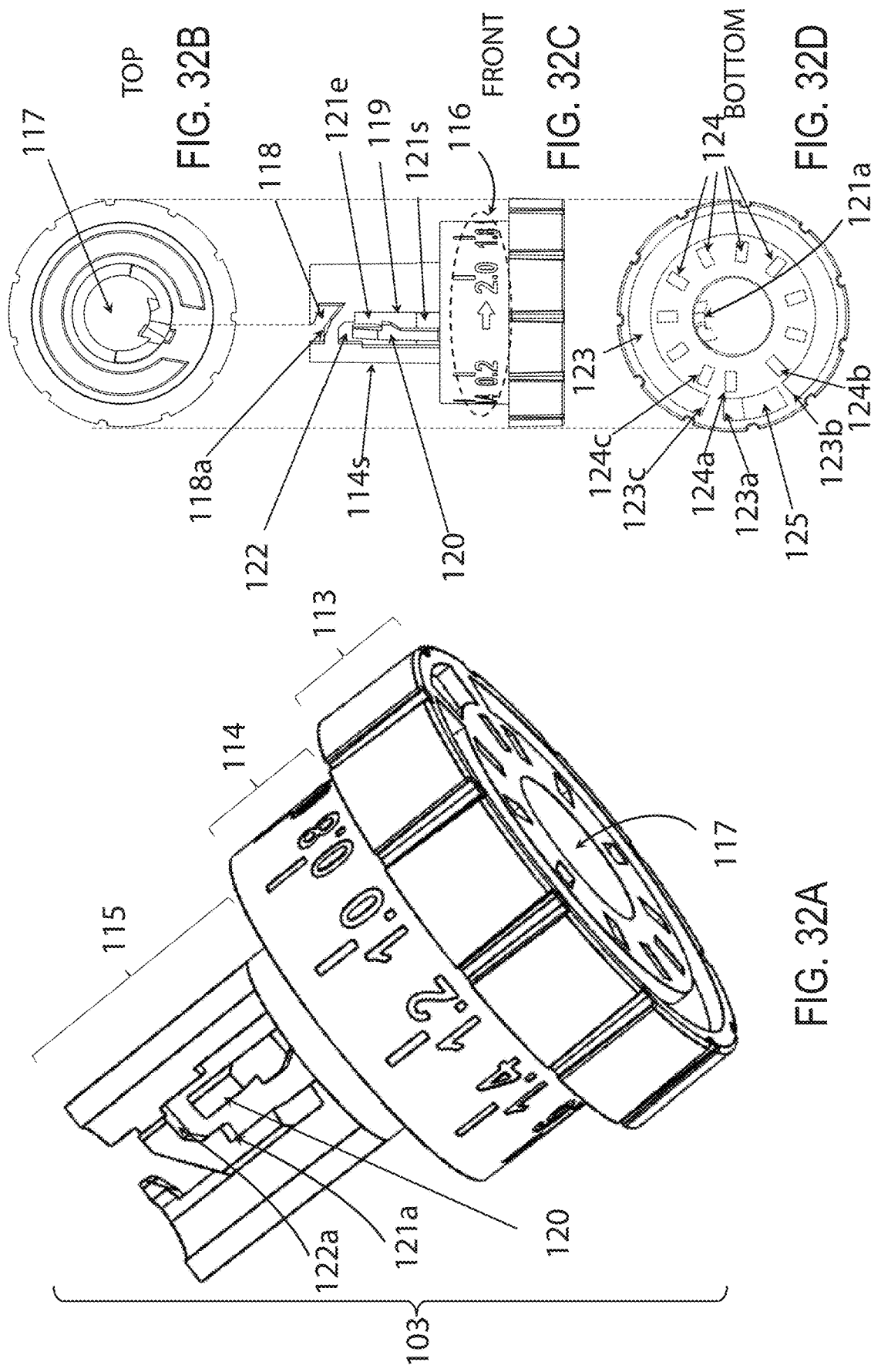

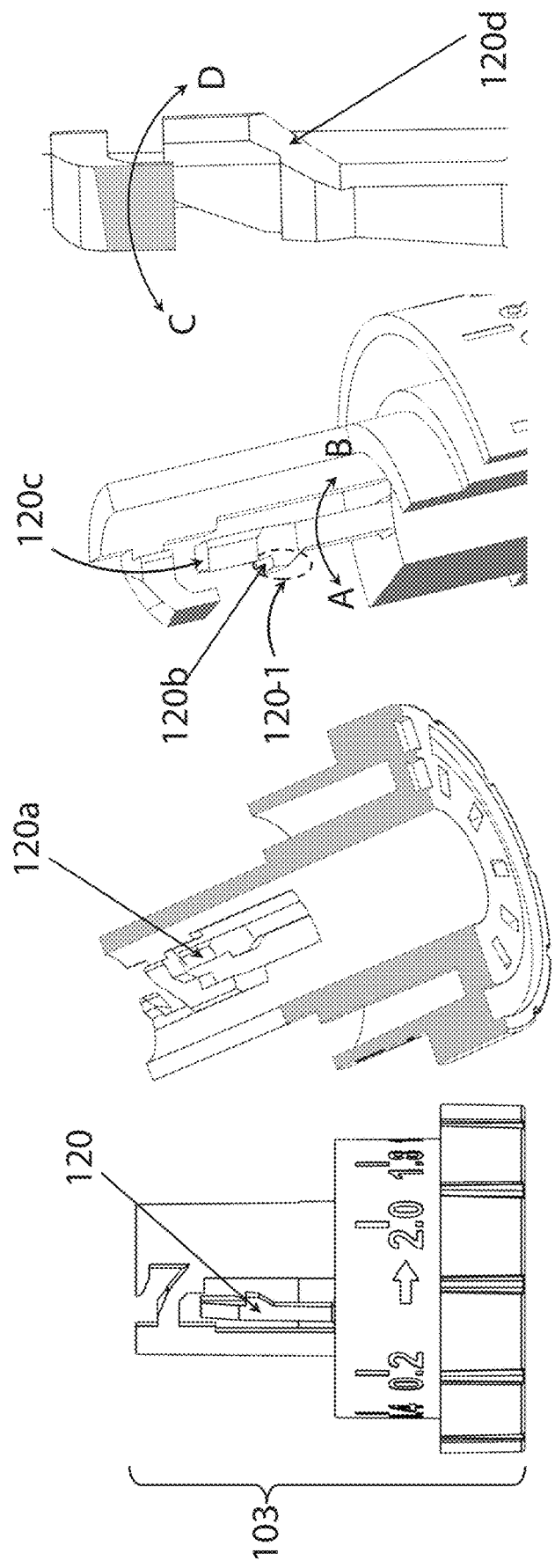

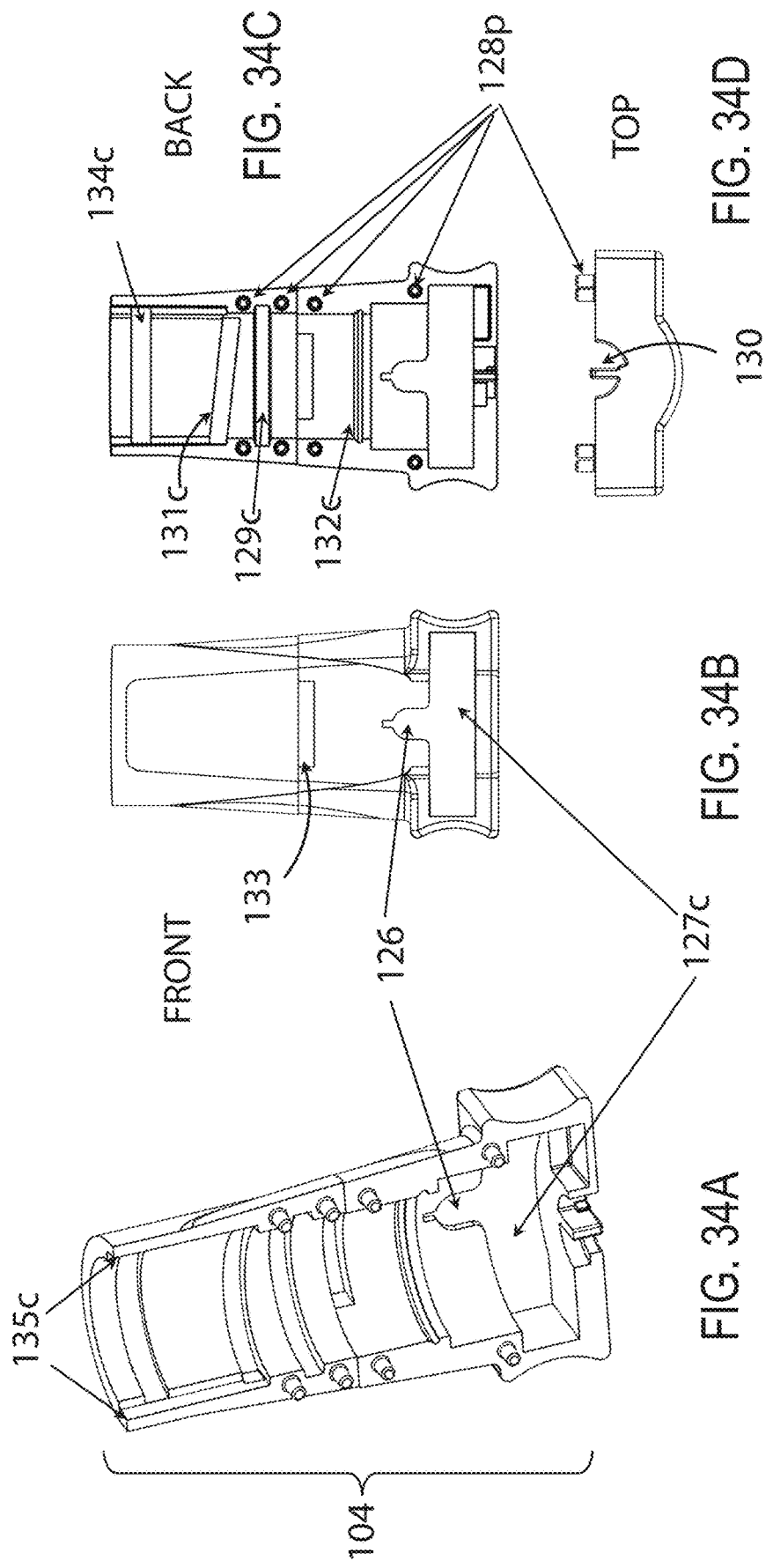

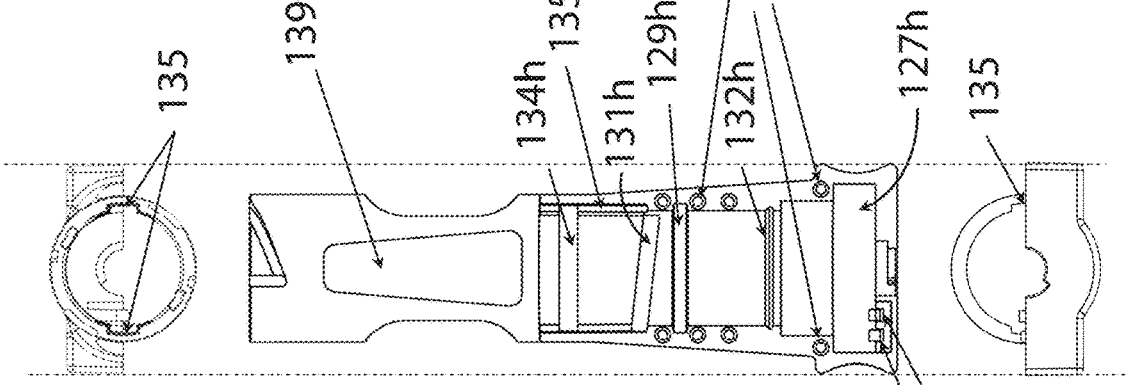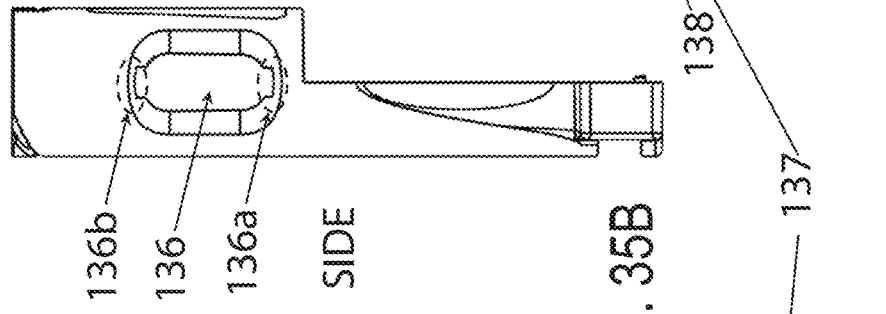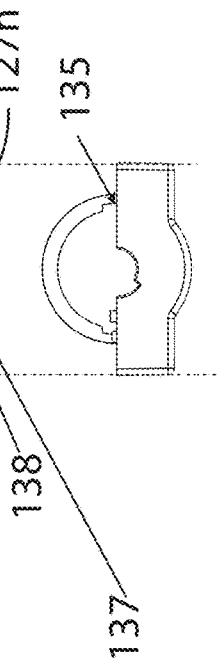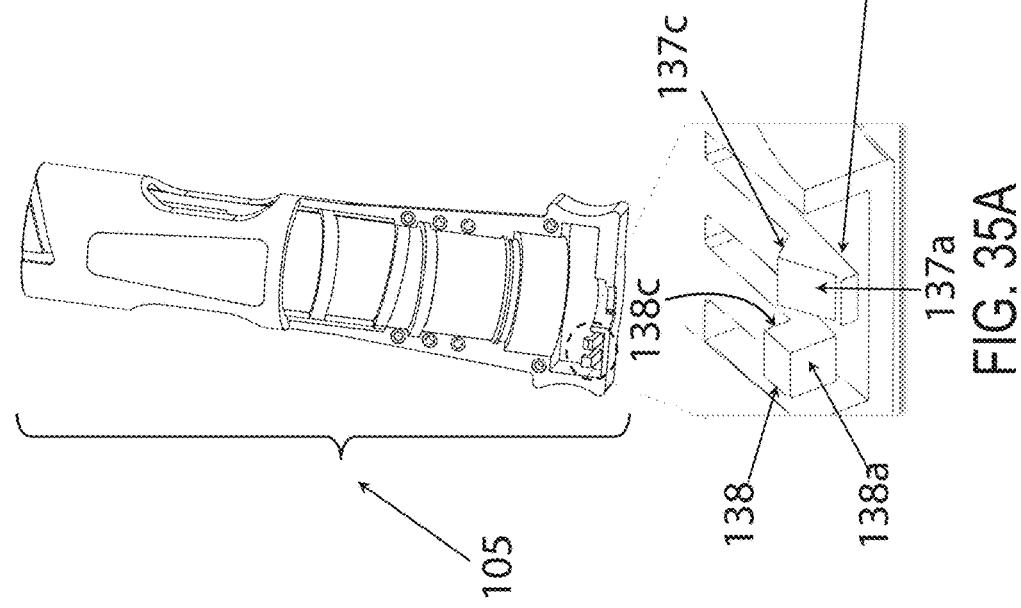

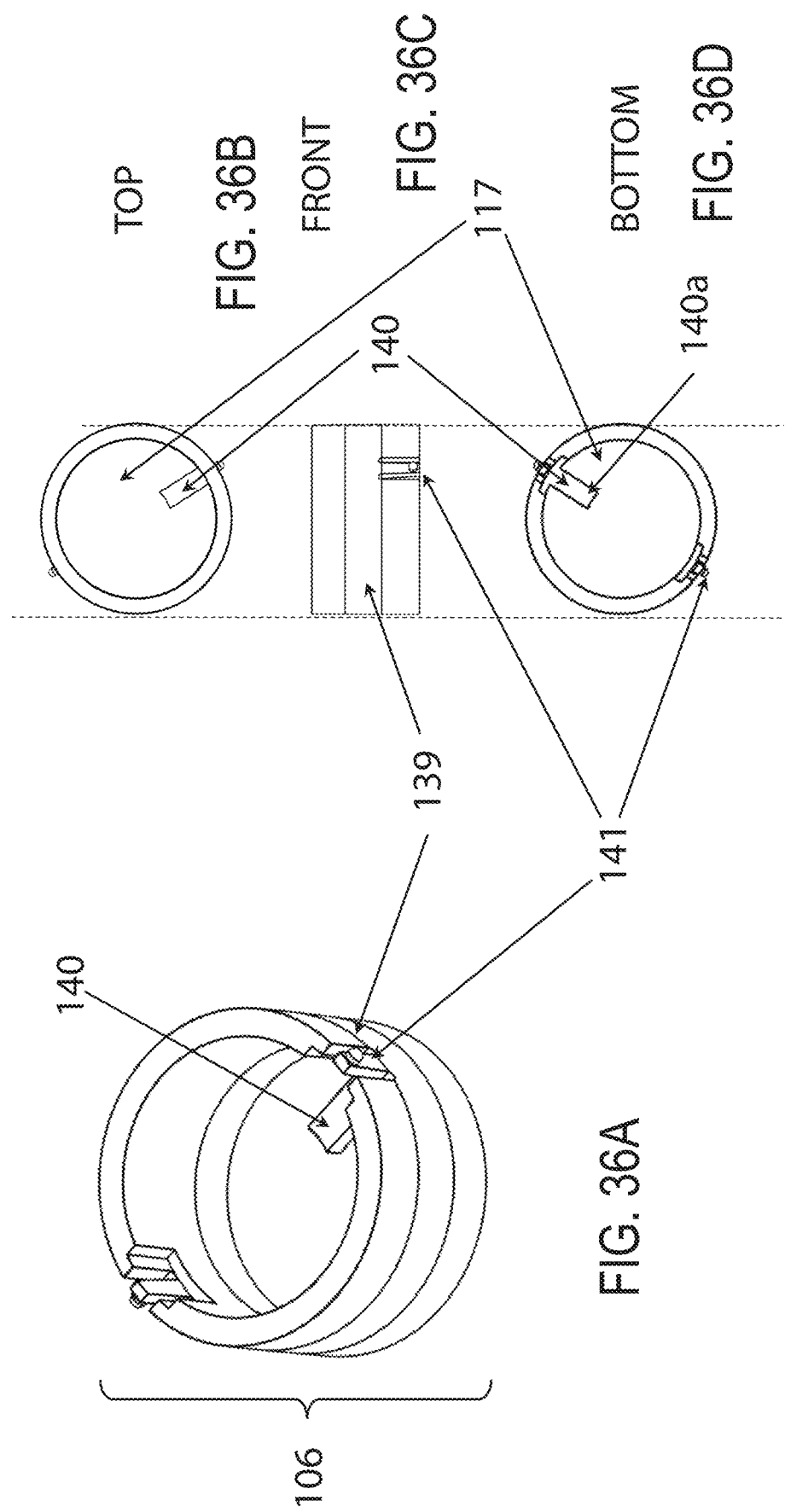

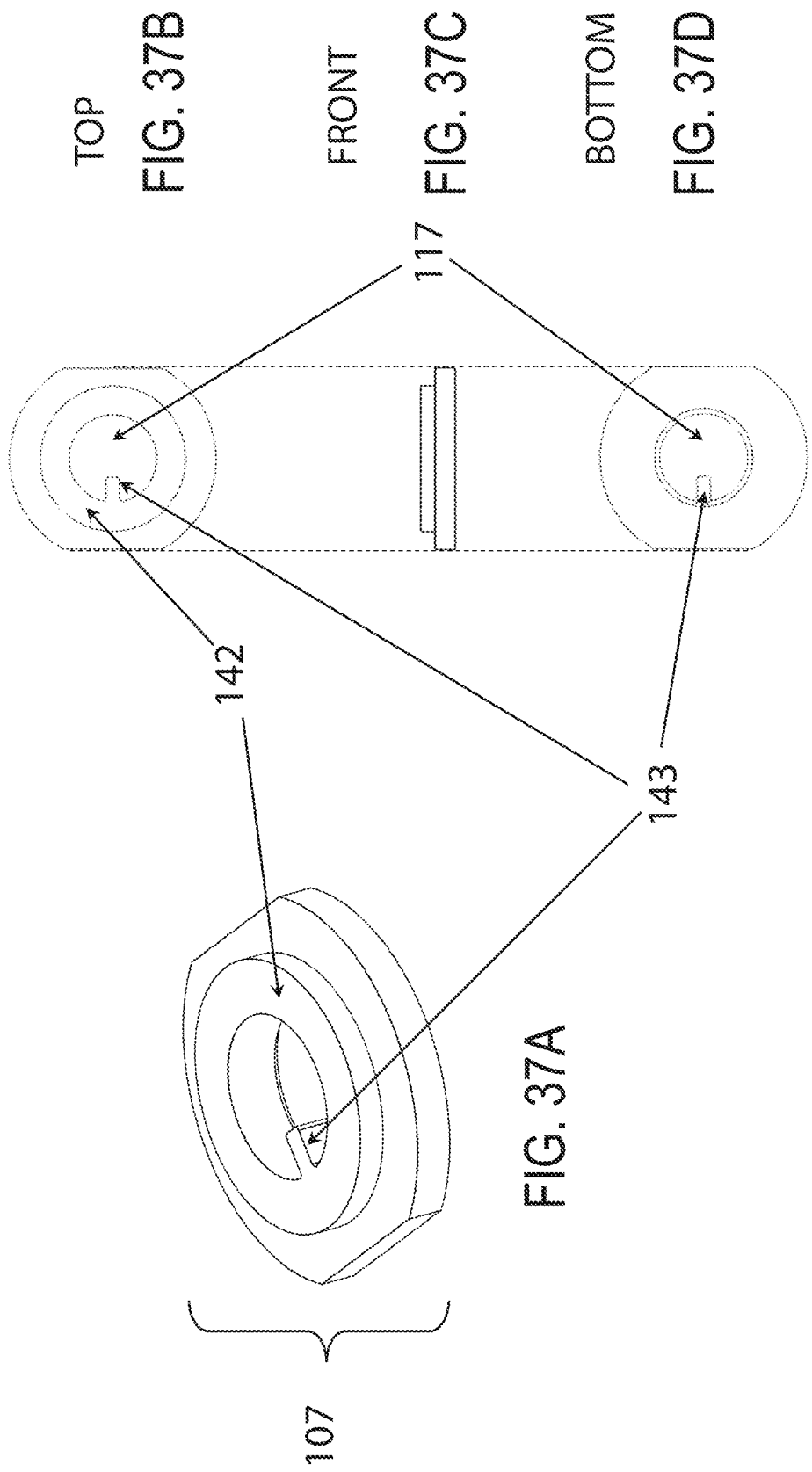

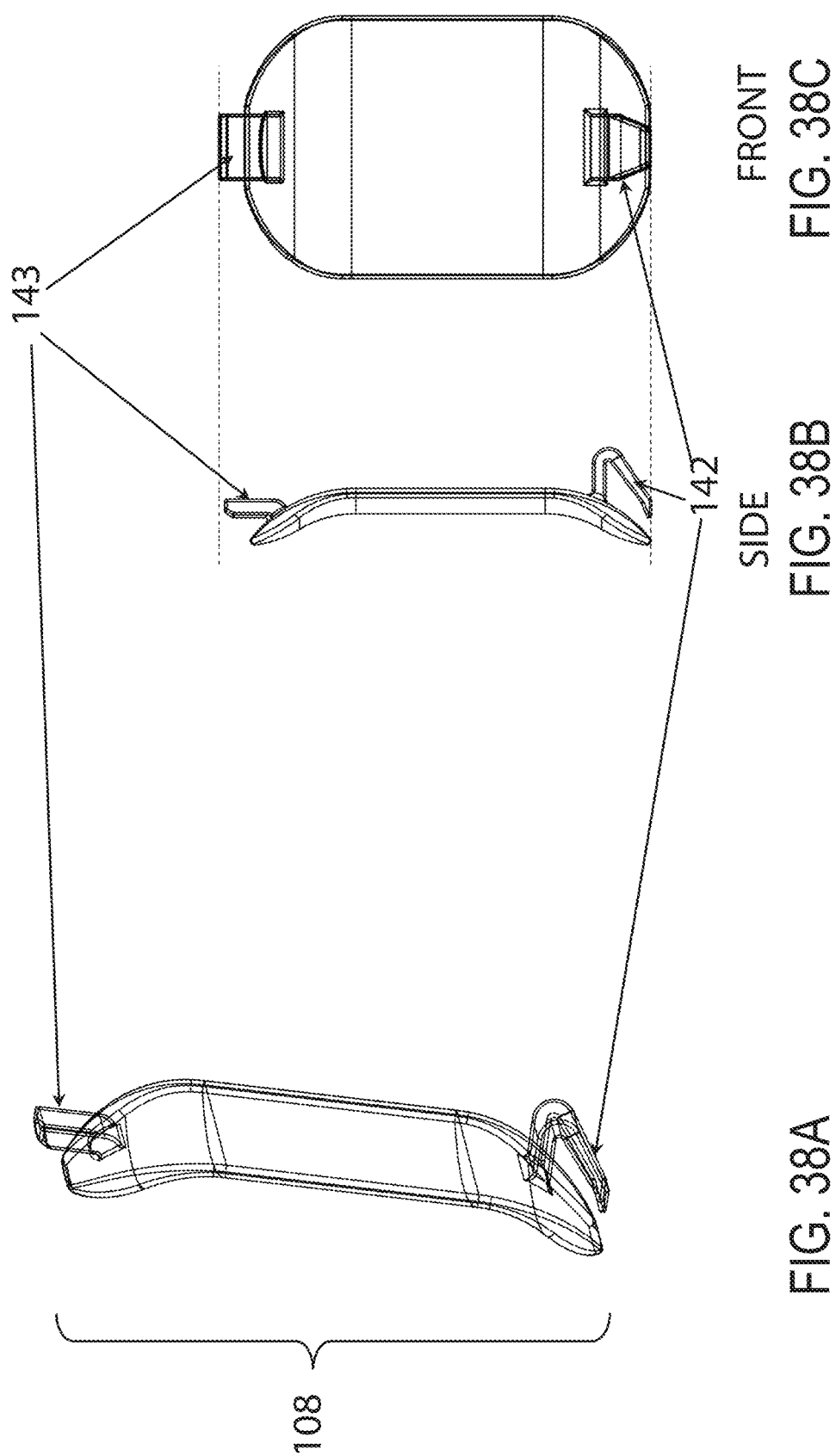

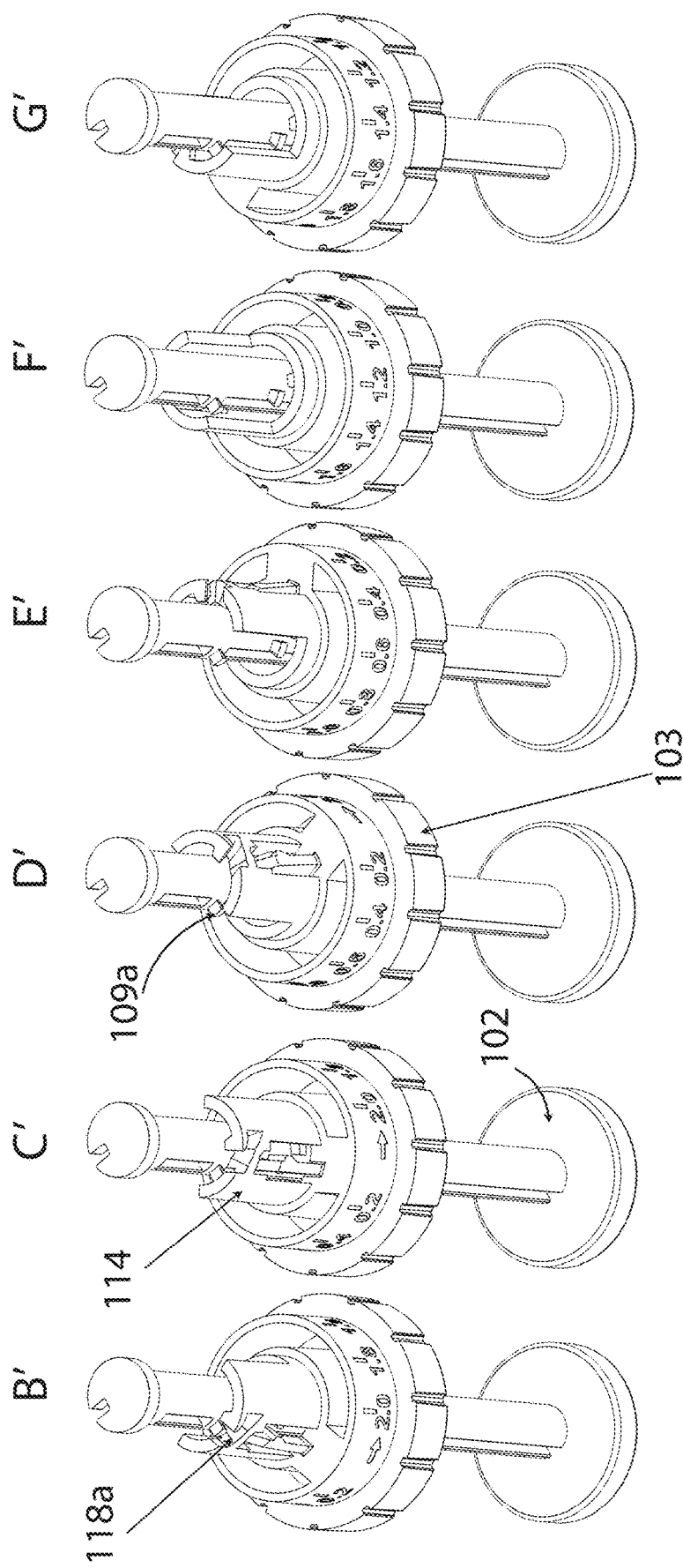

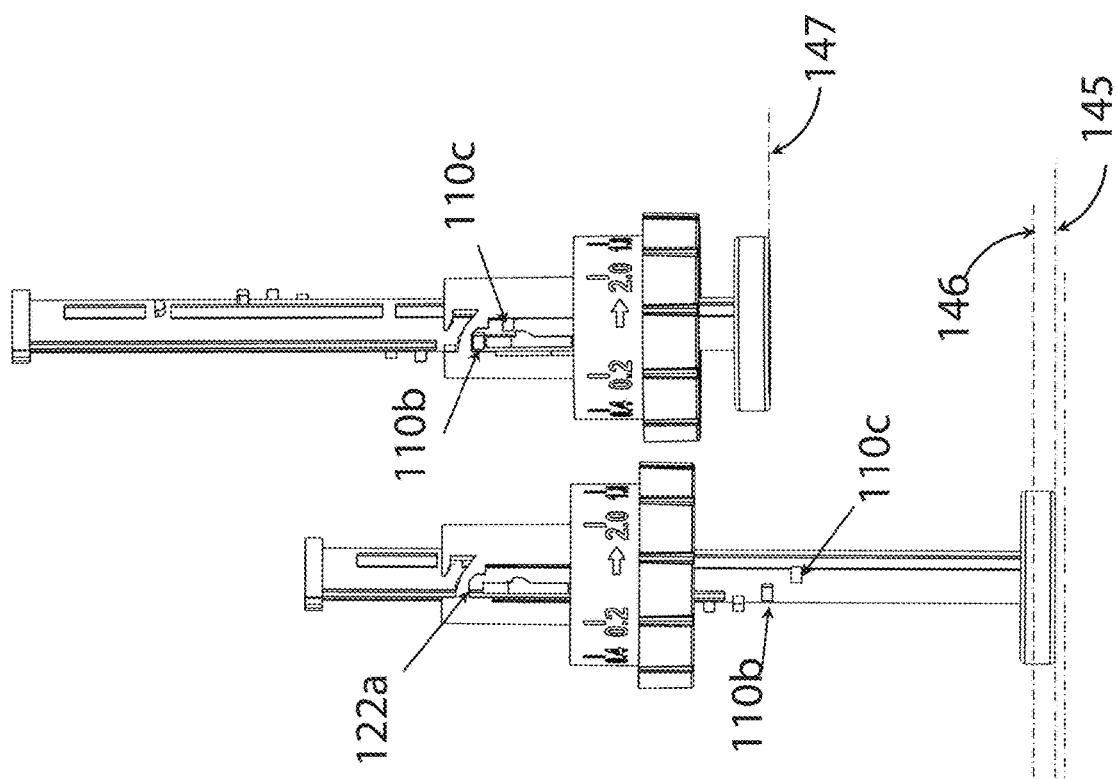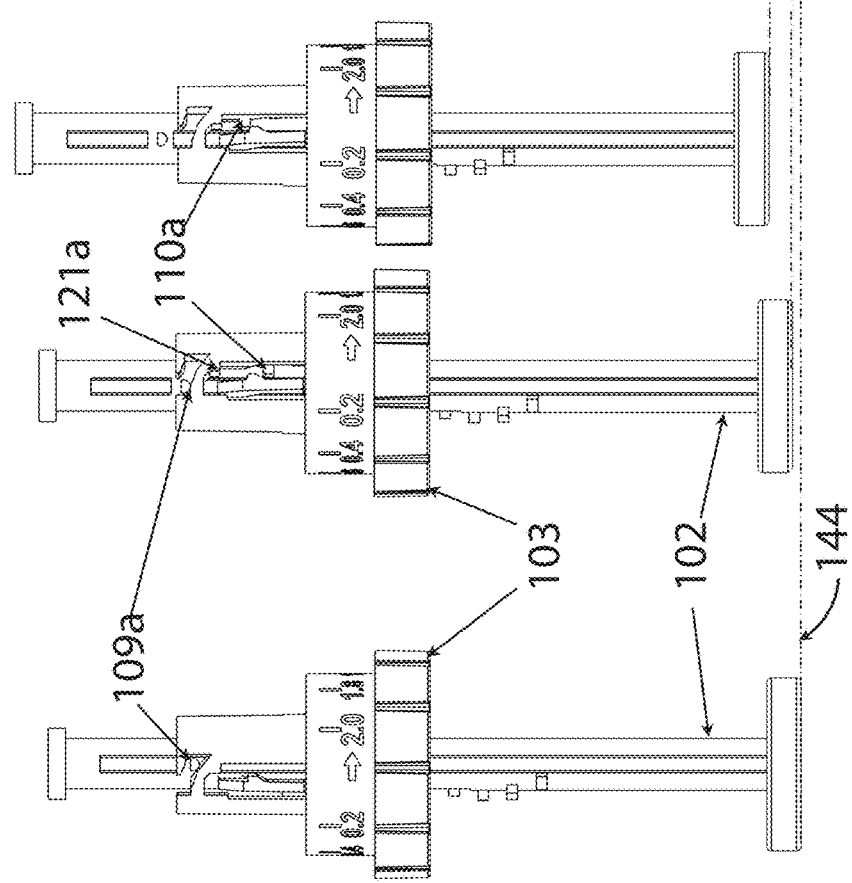
FIG. 42A  FIG. 42B  FIG. 42C  FIG. 42D  FIG. 42E

VARIABLE DOSING SYRINGE

CROSS-REFERENCE TO RELATED APPLICATIONS

This application claims the benefit of U.S. Provisional Application No. 62/935,193, filed on Nov. 14, 2019, the entire contents of which are incorporated herein by reference and for all purposes.

FIELD

The disclosure generally relates to drug delivery devices and, in particular, to metered dosing systems for prefilled syringes

BACKGROUND

Syringes are very commonly used for administration of injectable therapeutics or fluids. Syringes typically consist of a cylindrical Barrel, lubricated on its inner surface to enable an elastomeric Plunger Stopper to be axially manipulated with a Plunger Rod. There are several types of syringes designed with intended application in mind. Some syringes can also be used to store an injectable drug over several months; these involve specialized materials of construction for the syringe, including syringes that are lubricant-free. Syringes designed to store drugs are called prefillable syringes (PFS). Some syringes have an injection needle pre-attached to the syringe Barrel, while some other syringes have a luer lock feature to connect to other delivery conduits such as a catheter, injections ports and the like. Some syringe Barrels have dose markings printed on the outside surface to provide as a reference the user to set the dose; this is conventional dose metering.

Dose metering allows administration of different amounts of drug (e.g. drug dose) by simply varying the volume of the drug for a given concentration of the drug. The need to administer different drug dose amounts (i.e., dose metering) is driven by a number of factors; for example, in treatments for oncology dose metering helps administration of an amount of drug in accordance to patient weight. Another illustrative example is injection of insulin, where amount of insulin injected is based on the patient's blood glucose levels.

Most drugs have a therapeutic window to maximize the drug's efficacy. Amount of drug administered at a level below therapeutic window can result in sub-optimal efficacy of the drug, and conversely, amount of drug administered in excess of levels defined by the therapeutic window can expose the patient to toxic effects of the drug. Accuracy and precision of drug dose delivery is important to ensure optimal treatment outcomes with a given drug. Accuracy and precision of drug delivery is more challenging with sub-milliliter injection volumes. Injection of Sub-milliliter volumes are relevant in case of applications involving treatment of pediatric patients, injection of highly potent therapeutics (e.g., insulin, oncological agents, immunotherapies, etc.), targeted organ delivery (e.g., eye, brain, inner ear, etc.).

Congruent with need for accurate, precise dosing is the need to minimize the number of SKUs (stock keeping units) a pharmaceutical manufacturer has to maintain in order to streamline supply chain logistics for a drug that needs to be metered for aforementioned reasons. Each drug SKU has overheads involving formulation development, regulatory approvals, testing, manufacturing, storage, customer support, etc. Maintaining multiple SKUs of the same drug would have inherent redundancies that result in increasing the cost providing the drug to the patient.

Conventional dose metering with current syringes has limitations on the range of the volumes for a given syringe, and are inaccurate & imprecise to administer microliter size volumes. Conventional syringes are also limited in availability of features to maximize safety of drug administration—for example, needlestick prevention, drug counterfeit prevention, preventing abuse of unused drug, etc.

Injection devices also need to incorporate needle safety to mitigate risk from needlestick injuries in order to comply with regulations or ensure suitability of administration in a home setting. Actuation of needle safety should occur independent of dose volume injected. Also, it is important to prevent premature actuation of the needle safety mechanism that may result in non-treatment or under-dosing.

Pen injectors have been widely used in the injection of insulin. Pen injectors allow the user to select a dose amount (injection volume) and self-administer the medication. There are some limitations to broad applicability of pen injectors—a) pen injectors incorporate cartridges (not syringes), b) they need specialized needles for injection, c) designed for multiple use, d) maximum injection volume that can be practically delivered is about 1 mL, e) does not incorporate needle safety.

In any injectable dose delivery system involving a cylindrical barrel (syringe or cartridge), the volume of injected dose is defined by the difference between the beginning of dose position of the plunger stopper and the end of dose position of the plunger stopper (see FIG. 1). Errors in dose volume arise from variability in setting the aforementioned beginning of dose position and/or variability arising from end of dose position. This variability ultimately translates to inaccuracy and imprecision in the final dose volume delivered. Sources of this variability include user error and/or tolerances of components of the delivery system.

Manually operated, conventional dose delivery systems can deliver a range of volumes. All manually operated, conventional injectable dose delivery systems employ the same volume resolution for setting a dose volume irrespective whether a dose volume is selected at the lower end of the delivery volume range or the high end of the delivery volume range. This results in either limiting the maximum deliverable volume for devices with higher resolution for injection volume (e.g., pen injectors), or results in inaccuracy and imprecision at low volumes (microliter range) (e.g., conventional hypodermic and prefillable syringes). Simply increasing the volume range of the aforementioned higher resolution device, would result in increasing the overall size of the device to the point of rendering it impractical for use. Similarly, a large volume device (for e.g., 5 milliliter maximum volume syringe) would be unsuitable to deliver a small volume (for e.g., 10 microliter dose). When employing There is a trade-off between dose volume resolution and volume range in prior art for manually operated drug delivery systems.

The outer diameter of an elastomeric Plunger Stopper is slightly oversized relatively to the inner diameter of a Syringe—this helps create a seal in a prefilled syringe and non-prefilled syringes. After insertion of the Plunger Stopper into the Syringe, and during storage, the Plunger Stopper continues to exert a radially outward force against the inner diameter of the Syringe barrel creating 'stiction'. After extended storage of this prefilled syringe, additional effort is necessary to overcome stiction in order for the Plunger Stopper to break loose from its original position. An axially applied user force is commonly known as 'breakloose' force. Overcoming stiction with breakloose force results in temporary loss of user control of Plunger Rod travel. Consequences of this loss of control are particularly acute if a priming step is required prior to injection. Priming is important to ensure patency of the delivery conduit, such as a needle. Priming would help minimize the risk of air being delivered as part of the injection and hence minimize underdosing. Excess priming resulting in overshooting of the minimum volume necessary to perform the priming step, can result in wastage of drug and/or potentially underdosing of the maximum dose. Overcoming the Plunger Stopper stiction can be uncomfortable for the user.

SUMMARY

According to various embodiments, a plunger rod assembly for a syringe includes fine and course dose setting capability. The syringe can include one or more dials for effecting a fine dose setting and for effecting a coarse dose setting. According to various embodiments, a start of dose delivery position of a plunger rod of the plunger rod assembly that pushes a stopper in a barrel of a syringe to deliver a dose is the same regardless of the dose setting and an end of dose setting for controlling the stop position of the plunger rod is different for different doses. According to various embodiments, one or more rotational inputs can effect fine dose setting and coarse dose setting. In some embodiments, different dials serve as the user input for fine and coarse dose setting and in other embodiments, the same dial serves as the user input for both fine and coarse dose settings.

According to various embodiments, a plunger rod assembly for a syringe includes a main body, a plunger rod at least partially received in the main body and comprising a set of one or more protrusions, and a dosage setter operatively coupled to the plunger rod and comprising a rotatable body that comprises a set of one or more stops for engaging the set of one or more protrusions of the plunger rod depending on at least a rotational position of the set of one or more stops relative to the set of one or more protrusions, wherein a first rotational adjustment associated with the dosage setter is configured to set a first dosage increment by adjusting a relative axial position between the rotatable body and the plunger rod, and a second rotational adjustment associated with the dosage setting assembly is configured to set a second dosage increment that is larger than the first dosage increment by adjusting a relative rotational alignment between the set of one or more stops and the set of one or more protrusions.

In any of these embodiments, the first rotational adjustment can include a rotatable dial that engages the rotatable body and can rotate relative to the rotatable body to axially translate the rotatable body relative to the main body. In any of these embodiments, the rotatable dial can include a thread that engages a thread of the rotatable body.

In any of these embodiments, the second rotational adjustment can include a dial for rotating the rotatable body. In any of these embodiments, the rotatable body can translate relative to the dial. In any of these embodiments, the rotatable body and the dial can be fixed relative to one another.

In any of these embodiments, the first rotational adjustment can adjust an axial position of the rotatable body relative to the main body.

In any of these embodiments, the first rotational adjustment can adjust an axial position of the plunger rod relative to the main body.

In any of these embodiments, the plunger rod can be rotationally fixed.

In any of these embodiments, the rotatable body can be laterally offset relative to the plunger rod.

In any of these embodiments, a rotational axis of the rotatable body can intersect the plunger rod.

In any of these embodiments, the set of one or more protrusions can include a single protrusion and the set of one or more stops comprises a plurality of stops.

In any of these embodiments, the set of one or more protrusions can include a plurality of protrusions and the set of one or more stops comprises a single stop.

In any of these embodiments, the first rotational adjustment can include a slot in the rotatable body that receives a portion of the plunger rod, and the slot comprises a ramped surface that axially pushes the portion of the plunger rod received in the slot as the rotatable body rotates. In any of these embodiments, the set of one or more protrusions can include a single protrusion and the portion of the plunger rod is the single protrusion. In any of these embodiments, the portion of the plunger rod can escape one circumferential end of the slot such that continued rotation of the rotatable body does not cause further axial translation of the plunger rod relative to the rotatable body.

According to various embodiments, a plunger rod assembly includes a main body, a plunger rod at least partially received in the main body and comprising one or more protrusions, and a dosage setter that includes a rotatable body that comprises one or more first stops that align with the one or more protrusions to define a dosage delivery end position of the plunger rod, wherein different alignments of the one or more first stops with the one or more first protrusions define different dosage settings, and a second stop that engages the one or more protrusions of the plunger rod to define a dosage delivery start position of the plunger rod, wherein the dosage delivery start position of the plunger rod is the same for the different dosage settings.

In any of these embodiments, the one or more protrusions of the plunger rod can include a first protrusion, and wherein engagement between the first protrusion and the second stop defines the dosage delivery start position and engagement between the first protrusion and the one or more first stops defines the dosage delivery end position.

In any of these embodiments, the one or more protrusions of the plunger rod can include a first protrusion and a second protrusion, and wherein engagement between the first protrusion and the second stop defines the dosage delivery start position and engagement between the second protrusion and the one or more first stops defines the dosage delivery end position.

In any of these embodiments, the second stop can include a slot that receives a first protrusion of the one or more protrusions.

In any of these embodiments, the slot can include a ramped surface that pushes the first protrusion received in the slot as the rotatable body rotates in a rotation direction.

In any of these embodiments, the first protrusion can escape the slot as the rotatable body continues to rotate in the rotation direction, In any of these embodiments, the dosage setter can include a rotatable dial that engages the rotatable body and can rotate relative to the rotatable body to axially translate the rotatable body relative to the main body.

In any of these embodiments, the rotatable dial can include a thread that engages a thread of the rotatable body.

In any of these embodiments, the dosage setter can include a dial for rotating the rotatable body.

In any of these embodiments, the rotatable body can translate relative to the dial.

In any of these embodiments, the rotatable body and the dial can be fixed relative to one another.

In any of these embodiments, the rotatable body can translate relative to the main body to define the dosage delivery end position of the plunger rod.

In any of these embodiments, translation of the rotatable body can provide a first resolution of dosage setting and rotation of the rotational body defines a second resolution of dosage setting.

In any of these embodiments, the plunger rod can be rotationally fixed.

In any of these embodiments, the rotatable body can be laterally offset relative to the plunger rod.

In any of these embodiments, a rotational axis of the rotatable body can intersect the plunger rod.

In any of these embodiments, the rotatable body can include the second stop.

In any of these embodiments, the assembly can include a locking mechanism to rotationally constrain the dose setting dial at the dose delivery end position of the plunger rod.

According to various embodiments, a syringe includes any of the plunger rod assemblies described above.

In any of these embodiments, the syringe can be a prefilled syringe.

In any of these embodiments, the syringe can be a single use syringe for injection of only one dose.

In any of these embodiments, the syringe can include a retractable needle cover that is locked in an extended position at an end of dosage delivery.

According to various embodiments, a method for setting and delivering a dosage with a prefilled syringe includes applying a first rotational input to a dosage setter of the syringe to adjust a relative axial position between at least a portion of the dosage setter and a plunger rod of the syringe to set a first dosage increment; applying a second rotational input to the dosage setter of the syringe to adjust a rotational position of the at least a portion of the dosage setter to set a second dosage increment, wherein the second dosage increment is greater than the first dosage increment; and axially advancing the plunger rod to deliver the dosage from a dose-independent start of dose position.

In any of these embodiments, the first rotational input can be applied to a dial that is rotatable relative to the at least a portion of the dosage setter.

In any of these embodiments, the second rotational input can be applied to a second dial that is rotationally coupled to the at least a portion of the dosage setter.

In any of these embodiments, the at least a portion of the dosage setter can be axially translatable relative to the second dial.

In any of these embodiments, the at least a portion of the dosage setter can be axially translatable relative to the first dial.

In any of these embodiments, the first and second rotational inputs can be applied to a dial of the at least a portion of the dosage setter.

In any of these embodiments, applying the first rotational input can axially advance the plunger rod relative to a barrel of the syringe.

In any of these embodiments, applying the first rotational input can axially advance the at least a portion of the dosage setter relative to a barrel of the syringe.

In any of these embodiments, the at least a portion of the dosage setter can include at least one stop, the plunger rod can include at least one protrusion, and adjusting the rotational position of the at least a portion of the dosage setter can include aligning the at least one stop with the at least one protrusion.

In any of these embodiments, the second rotational input can be applied after the first rotational input is completed.

In any of these embodiments, the method can further include constraining the dose setter after delivering the dosage.

According to various embodiments, a method for setting and delivering a dosage with a prefilled syringe includes adjusting a relative axial position between at least a portion of a dosage setter of the syringe and a plunger rod of the syringe; rotating the at least a portion of the dosage setter to align at least one stop of the at least a portion of the dosage setter with at least one protrusion of the plunger rod; and axially translating the plunger rod to deliver the dosage until the at least one protrusion of the plunger rod engages the at least one stop of the at least a portion of the dosage setter.

In any of these embodiments, adjusting the relative axial position between the at least a portion of the dosage setter and the plunger rod comprises adjusting an axial position of the at least a portion of the dosage setter relative to a barrel of the syringe.

In any of these embodiments, adjusting the relative axial position between the at least a portion of the dosage setter and the plunger rod can include adjusting an axial position of the plunger rod relative to a barrel of the syringe.

In any of these embodiments, adjusting the relative axial position between the at least a portion of the dosage setter and the plunger rod can include a user-applied rotational input to the dosage setter.

In any of these embodiments, the rotational input can be applied to a dial of the dosage setter that rotates relative to the at least a portion of the dosage setter and can engage the at least a portion of the dosage setter such that the at least a portion of the dosage setter axially translates via rotation of the dial.

In any of these embodiments, the rotational input can be applied to a dial that is translationally fixed relative to the at least a portion of the dosage setter.

In any of these embodiments, rotating the at least a portion of the dosage setter can include a user-applied rotational input.

In any of these embodiments, the plunger rod can remain translationally fixed as the at least a portion of the dosage setter is rotated.

In any of these embodiments, the at least a portion of the dosage setter can remain translationally fixed as the at least a portion of the dosage setter is rotated.

In any of these embodiments, the method can further include axially constraining the plunger rod at end of delivery of dosage.

According to various embodiments, a method of delivering a dosage with a prefilled syringe includes setting a dosage of the syringe by setting an end of travel of a plunger rod of the syringe; axially translating the plunger rod of the syringe to deliver the dosage from a dose-independent start position; and revealing a completion of dosage delivery indicator at the end of travel of the plunger rod.

In any of these embodiments, the method can further include generating an audible indication of the completion of dosage delivery at the end of travel of the plunger rod.

In any of these embodiments, the method can further include locking a dose setter of the syringe apparatus at the end of the travel of the plunger rod.

In any of these embodiments, the method can further include withdrawing the syringe from an injection site after the completion of the dosage delivery and locking a needle shield in place.

In any of these embodiments, a fraction of dosage corresponding to difference between the total dosage and the delivered dosage can be retained in the syringe after completion of dosage delivery.

It will be appreciated that any of the variations, aspects, features and options described in view of the devise and assemblies apply equally to the methods and vice versa. It will also be clear that any one or more of the above variations, aspects, features and options can be combined.

BRIEF DESCRIPTION OF THE DRAWINGS

The invention will now be described, by way of example only, with reference to the accompanying drawings, in which:

FIG. 7 illustrates a plunger rod, according to various embodiments;

FIGS. 12A-12F illustrate a process for setting and delivery a dose, according to various embodiments;

FIGS. 13A-13C illustrate locking of a dose setting dial at an end of the dose delivery, according to various embodiments;

FIGS. 16A-16B illustrate a plunger rod, according to various embodiments;

FIGS. 17A-17F illustrate a housing, according to various embodiments;

FIGS. 18A-18D illustrate a clicker, according to various embodiments;

FIGS. 19A-19E and 20 illustrate aspects of a dose setter, according to various embodiments;

FIGS. 27A-27C and 28 illustrate a syringe cover, according to various embodiments;

FIGS. 31A-31B illustrate a plunger rod, according to various embodiments;

FIGS. 32A-32D and 33A-33D illustrate a dose setter, according to various embodiments;

FIGS. 34A-34D illustrate a cover, according to various embodiments;

FIGS. 35A-35E illustrate a housing, according to various embodiments;

FIGS. 36A-36D illustrate an end of dose indicator, according to various embodiments;

FIGS. 37A-37D illustrate a disc for preventing rotation of a plunger rod, according to various embodiments;

FIGS. 38A-38C illustrate a window cover, according to various embodiments;

FIGS. 40A-40G, 41A-41F, and 42A-42E illustrate various dose settings and dose delivery, according to various embodiments.

DETAILED DESCRIPTION

Figure 1:
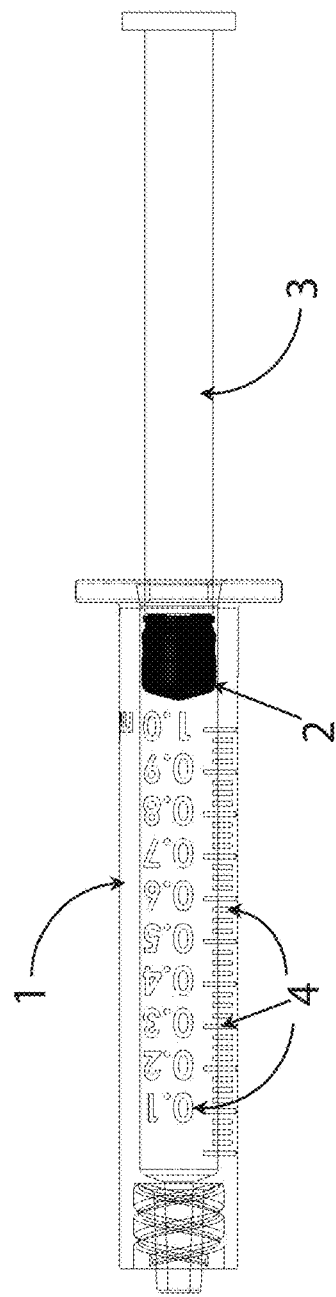
FIG. 1 shows a conventional syringe.

Devices and methods described herein, according to various embodiments, are directed to controlling dosage delivery, such as using a syringe or a cartridge. In order to provide appropriate resolution when setting the dose for either low volumes (less than 100 microliters) or higher volume (>100 microliter through milliliters), various embodiments include separate features for higher volume and low volume dose setting—often referred to below as coarse and fine dosage setting, respectively. A combination of the two settings provides wide range of dose setting options from low microliters through milliliters in a compact configuration that would be practical to use. Separating coarse and fine injection dose volume settings avoids redundancy of having microliter level resolution for milliliter dose volume, but providing necessary resolution for injecting microliter volumes.

According to various embodiments, a controlled dosage delivery device can include a syringe, a plunger stopper, a plunger rod, a dose stop, one or more dose setting dials, which can include a fine dose setting dial and a coarse dose setting dial or a single dial that can control both fine and coarse dose setting. According to various embodiments, the syringe can be a prefilled syringe with an elastomeric plunger stopper that is translated by a plunger rod. The plunger rod axial travel dispenses the injectable drug filled in the syringe. The amount of plunger rod axial travel defines the volume of injected dose. The plunger rod axially translates until a design feature on the plunger rod rests against a 'stop' feature of a dose stop.

According to various embodiments, the dose stop can have one or more radially arranged 'stop' features and the plunger rod can have one or more radially arranged protrusions, with a respective alignment between a stop feature and a protrusion corresponding to a dose setting. The 'stop' features and/or protrusions can be arranged at different longitudinal/axial positions. For example, the dose stop may include a plurality of stop features at different axial and circumferential positions and rotation of the dose stop can align a particular stop feature with a protrusion of the plunger rod to set the dosage corresponding to the particular stop feature. Aligning a different stop feature with the protrusion will set a different dose.

According to various embodiments, a fine dose setting dial can engage with the dose stop such that rotation of the fine dose setting dial results in axial translation of the dose stop, which axially translates the one or more stop features of the dose stop to provide a fine adjustment of the dose setting. The dose stop and/or dial can have a thread and the thread angle and thread pitch can define the resolution of fine dose adjustment. The selectability of alignment of a particular stop feature with a particular protrusion can provide a coarse dose setting adjustability while the axial/longitudinal position of the dose stop can provide a fine dose setting adjustability. The dose amount is hence user selectable by a combination of the fine dose setting dial and the coarse dose setting dial.

According to various embodiments, a higher resolution of plunger rod travel is reserved for a portion of total plunger rod travel, such as for micro-advancing the plunger rod to prime the syringe and/or to aid in overcoming stiction of the plunger stopper in a controlled manner. According to various embodiments, a single dose setting dial incorporate features for both high and coarse resolution of plunger rod axial translation. One or more stop features corresponding to various user-selectable dose amounts can be incorporated into the dose setting dial or the plunger rod, as discussed above. The plunger rod can include one or more radially extending protrusions, one or more of which may serve the dual purposes of interacting with the one or more stop features on the dose setting dial and enabling micro-advancing (high resolution travel) of the plunger rod caused by partial rotation of the dose setting dial. The plunger rod can incorporate features to provide audible and visual end of dose indicators in addition to tactile end of dose indication resulting from the protrusion on the plunger rod resting against the stop features on the dose setting dial at the end of dose. Visual and audible end of dose indicators can be important to provide user confirmation that the injection procedure is complete in a system where the end of dose position of the plunger rod varies depending on the dose selected by the user.

According to various embodiments, according to various embodiments, stop features corresponding to various user-selectable dose amount are incorporated onto the plunger rod. Depending on the dose volume selected, one of these stop features can translate until it reaches a stop feature of the dose stop to define the end of the delivery of the intended dose (end of dose). According to some embodiments, concurrent with this end of dose is an audible and/or visual end of dose indication to the user. The visual end of dose indication can include an end of dose drum that axially translates towards the end of injection stroke with a marked colored feature becoming visible to the user towards the end of injection stroke.

According to various embodiments, a syringe is a pre-filled single use syringe for injecting only one dose. According to various embodiments, in instances where maximum possible volume of drug in a syringe is not administered, the undelivered drug remaining in the syringe is considered a biohazard. To minimize likelihood of abuse of this unused drug by reusing the device, the plunger rod and dose setting dial can be locked in position.

According to various embodiments, a drug delivery device can include one or more needle safety features for embodiments in which a needle is pre-attached (staked) to the syringe in any of the device embodiments described above. According to various embodiments, a needle safety is actuated independently of the dosing mechanism. According to other embodiments, the needle safety is actuated by the injection stroke, such as toward the end of dose. Actuation of needle safety can disable the injection device. Thus, according to various embodiments, actuation of the needle safety by completion of the injection can disable the injection device and ensure that the needle safety is actuated only when the user-selected dose is delivered.

According to various embodiments, prefillable syringes can have flanges, such as rounded or having diametrically opposite flats, and one or more features on elements incorporated into syringe retention components in the device minimize rotation of the syringe irrespective of the design of the syringe flange.

In the following description of the disclosure and embodiments, reference is made to the accompanying drawings in which are shown, by way of illustration, specific embodiments that can be practiced. It is to be understood that other embodiments and examples can be practiced, and changes can be made, without departing from the scope of the disclosure.

In addition, it is also to be understood that the singular forms "a," "an," and "the" used in the following description are intended to include the plural forms as well, unless the context clearly indicates otherwise. It is also to be understood that the term "and/or," as used herein, refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units, but do not preclude the presence or addition of one or more other features, integers, steps, operations, elements, components, units, and/or groups thereof.

FIG. 1 illustrates a conventional syringe-based delivery system, which includes a cylindrical barrel 1 which may be lubricated on its internal surface to enable an elastomeric plunger stopper 2 to translate along the barrel axis by a standard plunger rod 3. The user can select a dose by aligning the tip of stopper with dose volume markings 4 printed on the external surface of barrel 1. This would be the start of dose position. The user then inserts the delivery conduit (for e.g., a needle, catheter, etc. connected to or pre-attached to the syringe) into the injection site and axially depresses the plunger rod 3 until the plunger stopper bottoms out. The aforementioned dose markings 4 provide the same resolution for dose setting irrespective of whether the user selects a dose at low or high end of the volume range. In the example illustrated in FIG. 1, if the intended dose was less than 0.1 ml, having more resolution would be desirable to ensure accurate, precise delivery. Conversely, the resolution needed for accurate, precise delivery of a 0.9 ml dose is adequate in the illustrated example. Also, if a low volume (e.g., 0.1 ml in current examples of FIG. 1) was required to be administered using a prefilled syringe (where 1 ml of the drug was filled by the drug manufacturer), the user would have to squirt out 0.9 ml of the drug before administering the injection. This exposure of the wasted drug to the user can be potentially harmful to the user, caregiver, family members in case of potent drugs such as chemotherapeutics, oncolytic viruses, gene therapies, etc. This situation is endemic to all non-pen injector-based drug delivery device solutions in the prior art. If a fraction of the total drug enclosed in the syringe is to be delivered, it is desirable to administering the intended dose only and retain the remained of the dose in the syringe. The used syringe with the undelivered drug can be disposed safely without unnecessary exposure to the drug.

Figure 2:
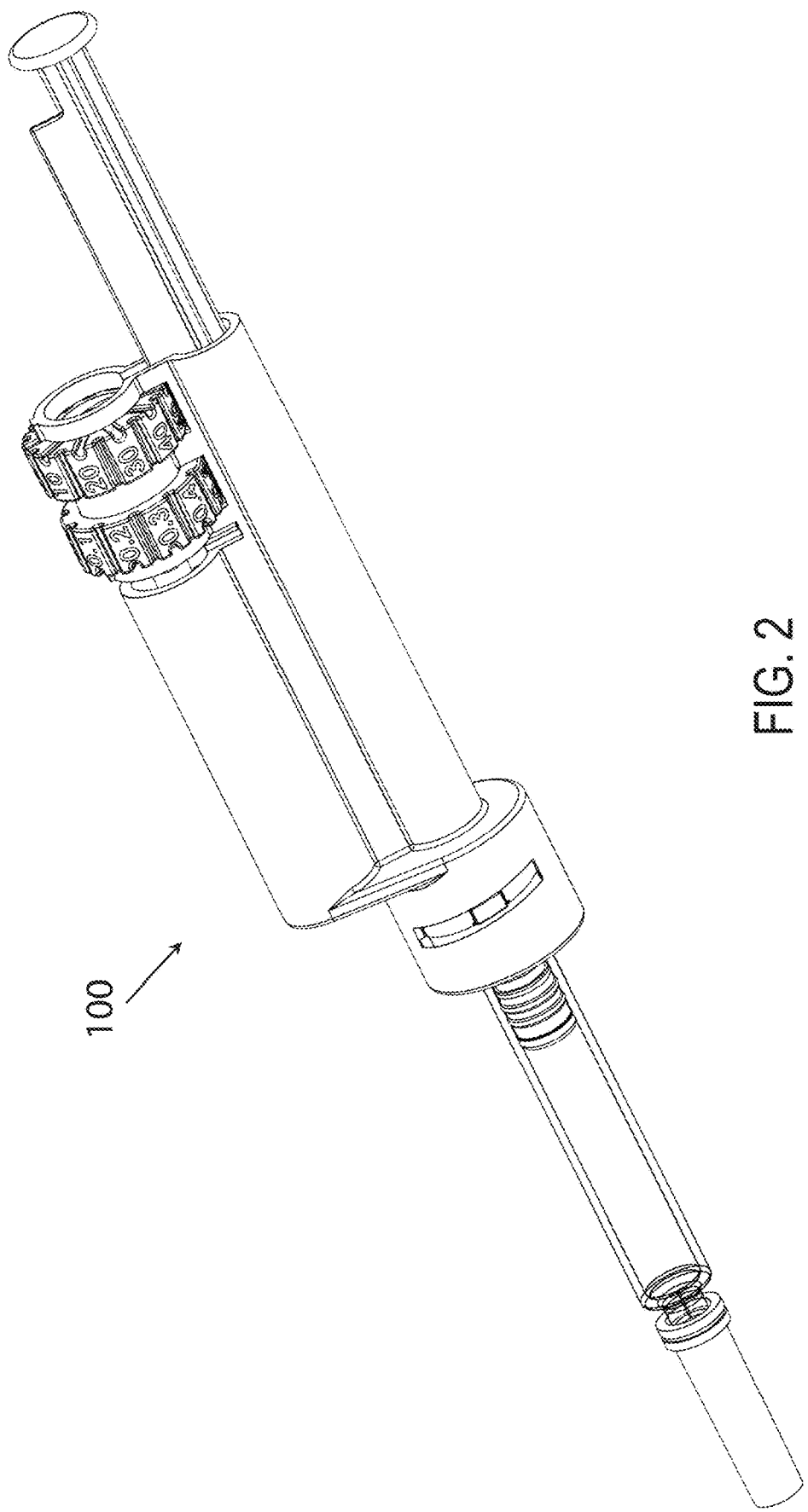
FIG. 2 illustrates a syringe, according to various embodiments.
Figure 3:
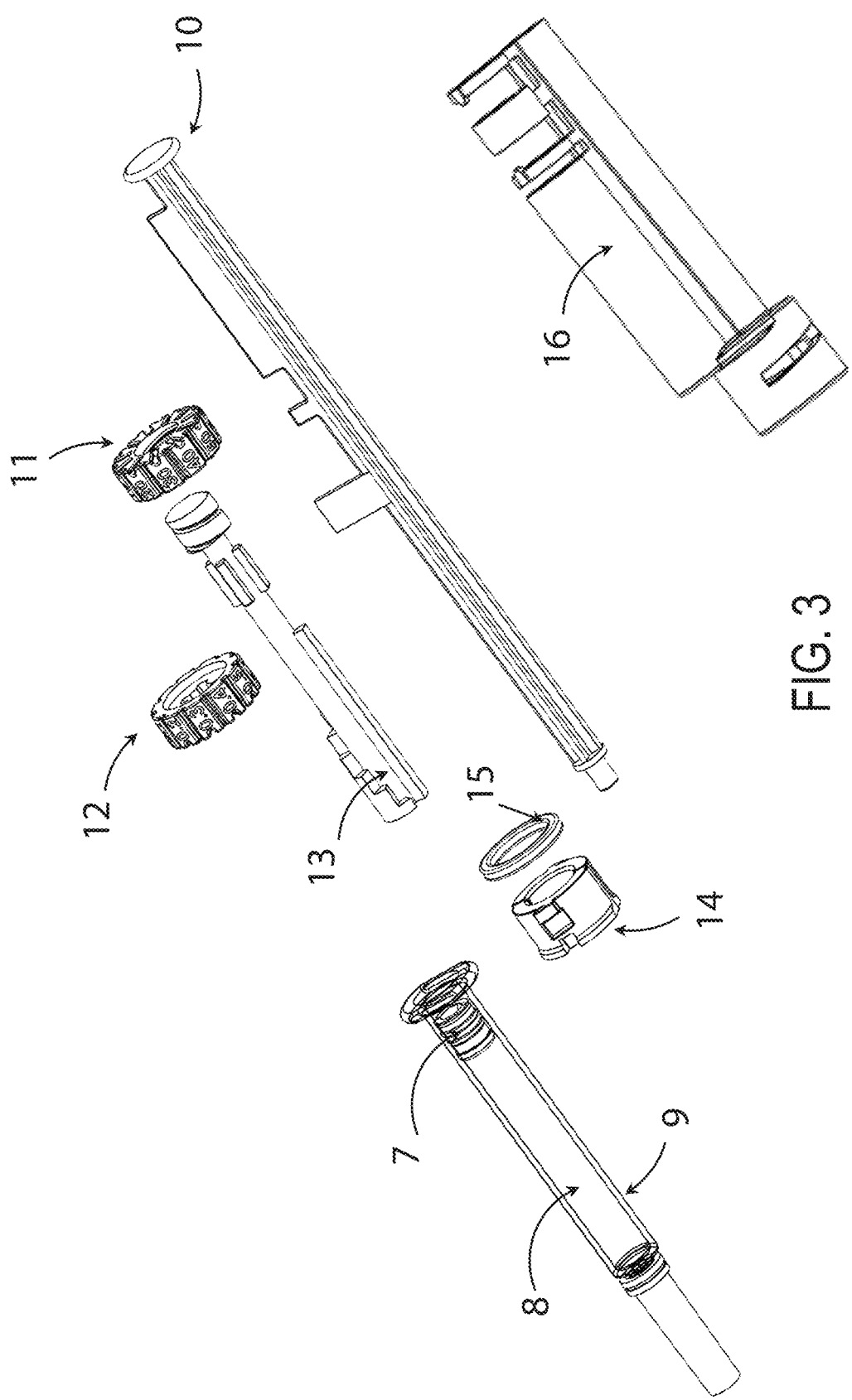
FIG. 3 is an exploded view of various aspects of the syringe of FIG. 2, according to various embodiments.

According to various embodiments, a variable dosing syringe 100 configured to provide user-control over resolution of dose setting, enabling the user to select the volume of injection and prevent unnecessary exposure to excess drug is illustrated in FIG. 2. The variable dosing syringe embodiment provides separate fine and coarse setting of the intended dose volume. Illustrated is an embodiment intended to deliver up to 1 milliliter with resolution of setting a dose either 0.1 milliliter or 0.01 milliliter (i.e., 10 microliters) depending on the desired volume to be injected. Therefore, 100 dose volume levels (0.01 milliliter minimum dose through 1 milliliter maximum dose in 0.01 milliliter increments) can be achieved by variable dosing syringe illustrated here. Components of the variable dosing syringe 100, according to various embodiments, are illustrated in FIG. 3. As an example, a standard prefillable syringe 9 with maximum fill volume of 1 ml with needle pre-attached (staked) into it can be used but it should be understood that the devices, methods, and principles described herein can be used with any syringe size and any syringe configuration.

The variable dosing syringe 100 includes a plunger rod assembly that can be attached to a proximal end of the syringe 9, such as via clip 14 and x-ring 15. The plunger rod assembly can include a housing 16 (also referred to herein as a main body), a plunger rod 10, a dosage setter that includes a rotatable body 13 (also referred to below as a "dose stop") and one or more dials (dials 11 and 12 are shown). The syringe 9 can be filled with injectable drug 8 and contains an elastomeric plunger stopper 7. According to various embodiments, fine and coarse dose volume setting is facilitated by fine dose setting dial 11 and coarse dose setting dial 12 respectively. The device includes a dose stop 13. The aforementioned components are supported or contained within a housing 16. Retention of the prefillable syringe 9 to the housing 16 is accomplished with clip 14 and an elastomeric x-ring 15.

Figure 4:
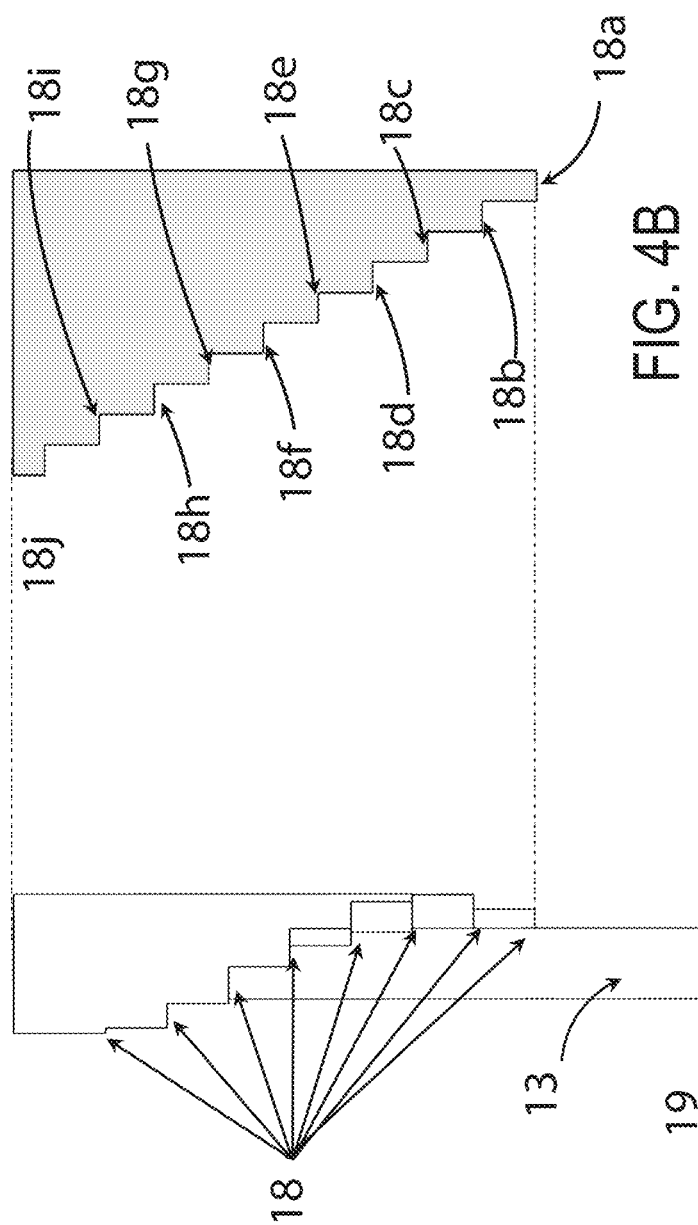
FIGS. 4A and 4B illustrate various aspects of a dose stop, according to various embodiments.
Figure 10:
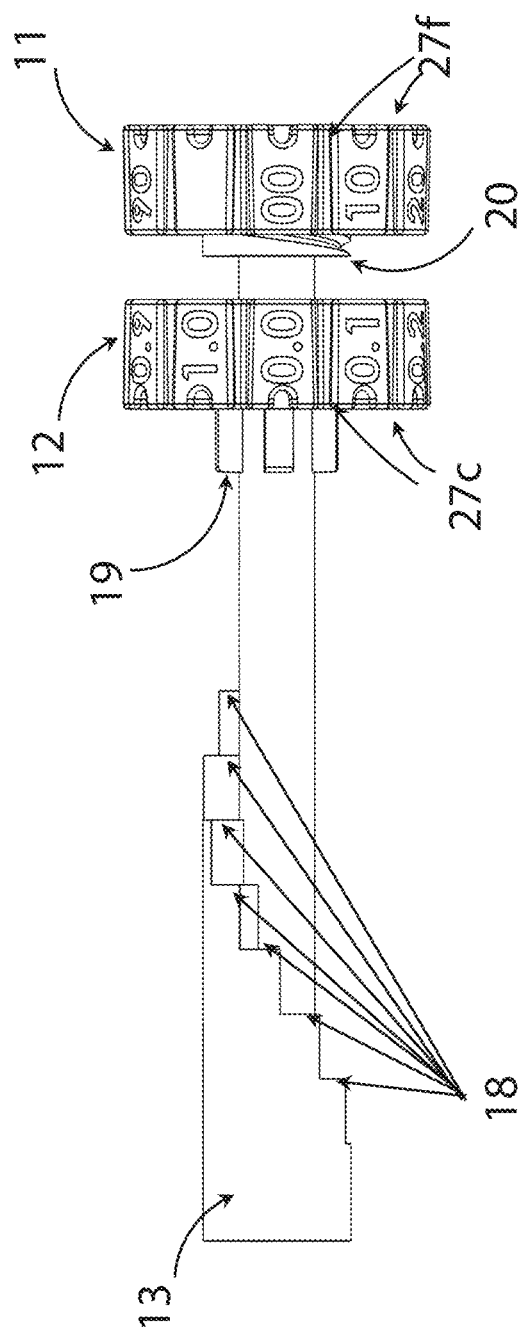
FIG. 10 illustrates a dose setter, according to various embodiments.

It is common for prefilled syringes with pre-attached (or staked) needle to be made available to the user in a ready to inject presentation. Similarly, according to various embodiments, the variable dosing syringe 100 can have a prefilled syringe 9 in which the axial position of the plunger rod 10 is in the start of dose position as provided to the end user. The end of dose position can be defined by the dose stop 13. An embodiment of dose stop 13 is illustrated in FIG. 4A. As shown in FIG. 4A and FIG. 10, end of dose is facilitated by a stop surfaces 18 on dose stops 13. Each stop surface 18 is circumferentially arranged and each corresponds to coarse dose volume that can be set. The axial position of each stop surface 18 is defined by dose volume amount on the coarse dose setting dial 12. The dose stop 13 includes four spline segments 19, each of the same length, placed at the same axial position on the dose stop 13, and arranged 90 degrees relative to each other. These spline segments 19 interact with the coarse dose setting dial 12. Dose stop 13 also includes threads 20, which interact with fine dose setting dial 11. Unfolding the dose stop surface portion of the cylindrical dose stop 13 in FIG. 4B and FIG. 10 show stop surface 18$a$ corresponds to the lowest volume on the coarse dose setting dial 12 and stop surface 18$j$ corresponds to the highest volume on the coarse dose setting dial 12. The end of dose position for the plunger rod 10 is determined by one of the stop surfaces 18, the axial position of which is a combination of the coarse dose amount set and axial advancing of the dose stop 13 mediated by the rotation of the fine dose setting dial 11. The resolution of fine dose setting is determined by the angle of female threads 20.

Figure 5:
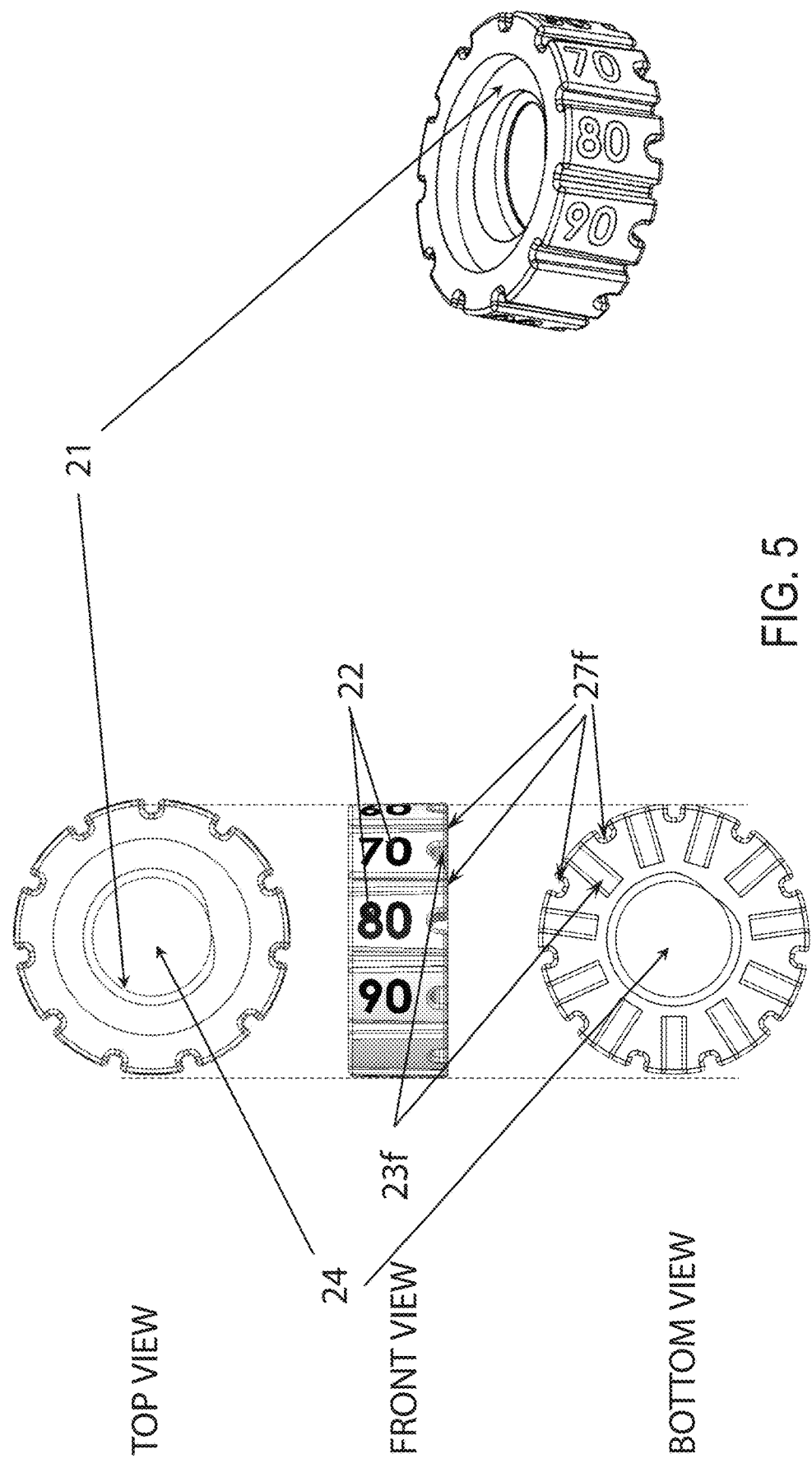
FIGS. 5 and 6 are examples of dose setting dials, according to various embodiments.

Shown in FIG. 5 is an example of a fine dose setting dial 11, which includes male threads 21 to match the pitch and thread angle of female threads 20. Markings 22 corresponding to fine dose levels that provide finer resolution of dose setting are printed on the cylindrical surface of the fine dose setting dial 11. Radial grooves 23$f$ are present on the bottom surface. Each groove 23$f$ is spaced at an angle defined by the amount of rotation of the fine dose setting dial 11 to cause axial translation of the dose stop 13 corresponding to dose volume resolution to be afforded by the fine dose setting dial 11. Grooves 23$f$ help fix the rotation position of the fine dose setting dial 11. The dose stop 13 is disposed within cavity 24. Longitudinal grooves 27$f$ on the cylindrical surface of the fine dose setting dial 11 are separated by the same angle as 23$f$; these longitudinal grooves play a role in locking of the fine dose setting dial at the end of injection. Friction between mating threads 20 and 21 axially constrain the dose stop 13.

Figure 6:
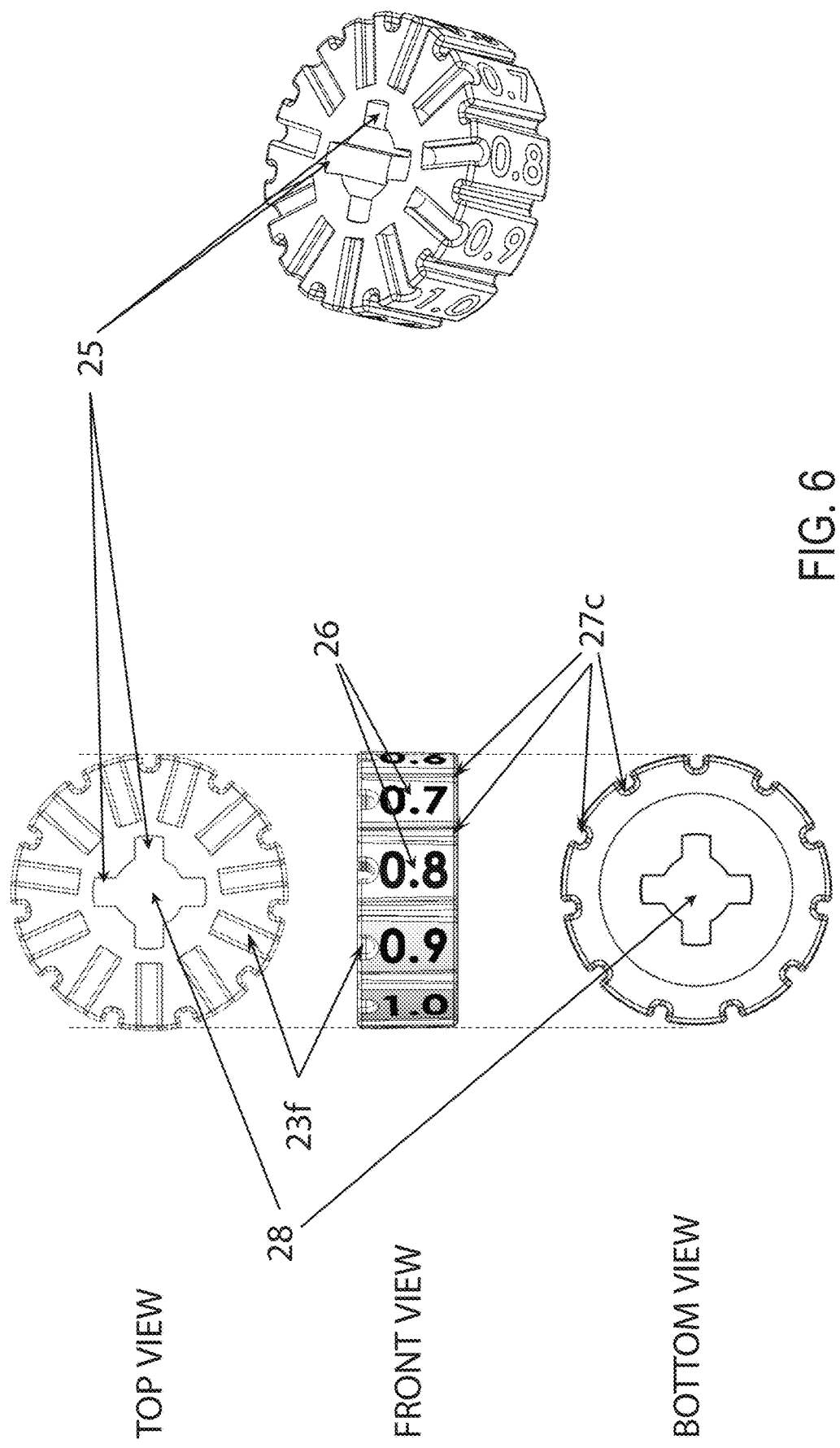

Shown in FIG. 6 is an example of the coarse dose setting dial 12, which include axial keyways 25, that align with and accommodate spline segments 19 on dose stop 13. Radial grooves 23$c$ are present on the top surface. Grooves 23$c$ help fix the rotation position of the coarse dose setting dial 12. Each groove 23$f$ is spaced at an angle same as angle between the stop surfaces 18 and the number of grooves 23$c$ are one more than the number of stop surfaces 18. Longitudinal grooves 27$c$ on the cylindrical surface of the coarse dose setting dial 12 are separated by the same angle as 23$c$; these longitudinal grooves play a role in locking of the fine dose setting dial at the end of injection. The dose stop 13 is disposed within cavity 28. Markings 26 corresponding to coarse dose levels that provide coarse resolution of dose setting are printed on the cylindrical surface of the fine dose setting dial 12.

According to various embodiments, features of the plunger rod 10 are illustrated in FIG. 7. Locking blade 29 and low dose locking blade 30 are longitudinally placed but axially separated from each other and from dose stop flag 31. The user administers the injection by pushing the finger seat 32, which helps axially translate the plunger 10 until dose stop flag travel is interrupted by a stop surface 18 on dose stop 11; this stop surface and its axial distance from the start of injection is defined by the fine dose setting dial 11 and coarse dose setting dial 12. Distal end 43 of the plunger rod interfaces with the side opposite to the drug contacting side of plunger stopper 7. This distal end 43 may be adapted to mate with the plunger stopper 7 in some applications.

Figures 8A, 8B:
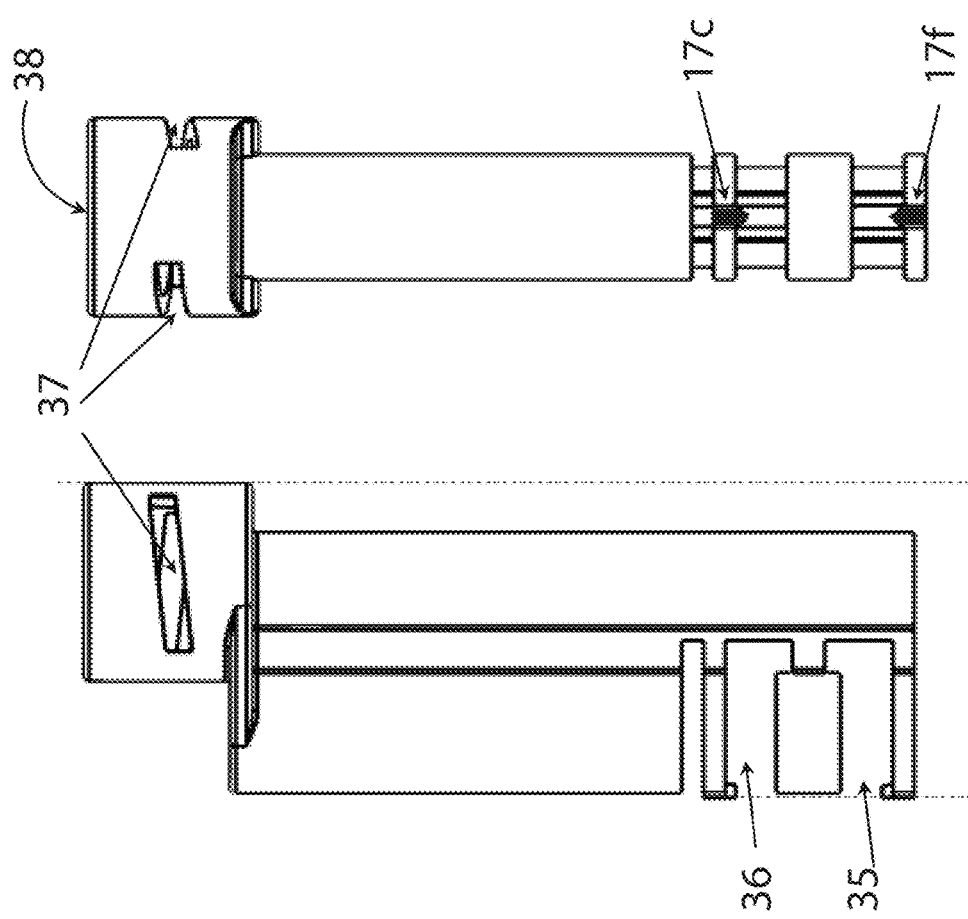
FIGS. 8A-8B illustrate a housing of a plunger rod assembly, according to various embodiments.

Features of housing 16 are shown in FIGS. 8A-8B. Axial cavities 33 and 34 contain the dose stop 13 and plunger rod 10 respectively. The fine dose setting dial 11 is placed in side slot 35, whereas the coarse dose setting dial 12 is placed in side slot 36. Along the axis of the device, side slot 35 is constrained by a hollow circular beam with marked tip 17$f$. The tip of 17$f$ when located within the trough of radial grooves 23$f$ help register dose set position for the fine dose setting dial 11. Along the axis of the device, side slot 36 is constrained also by a hollow circular beam with marked tip 17c. The tip of 17c when located within the trough of radial grooves 23c help register dose set position for the coarse dose setting dial 12. Both circular beams deflect enough to enable rotation of the fine and coarse dose setting dials. The fine and coarse dose setting dials are axially constrained by the housing 16 and radially constrained by the dose stop 13. The syringe is attached to the housing 16 by placing it into cavity 38.

Figures 9B, 9C:
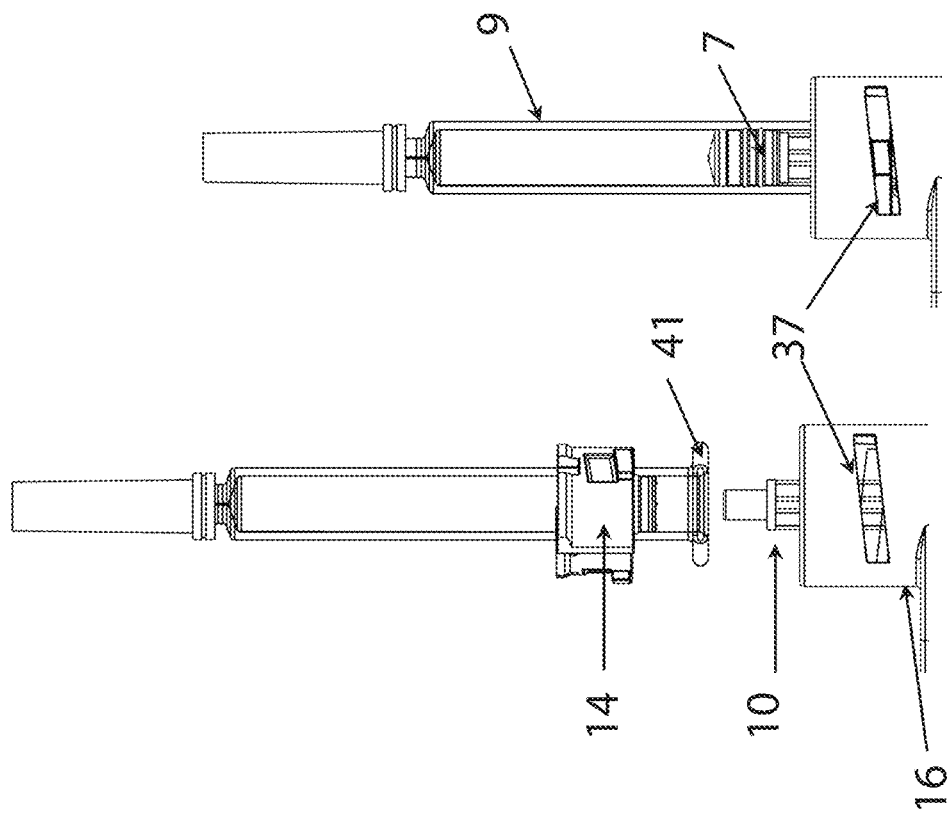
FIGS. 9A-9C illustrate various features for retention of a plunger rod assembly on a syringe body, according to various embodiments.
Figure 9A:
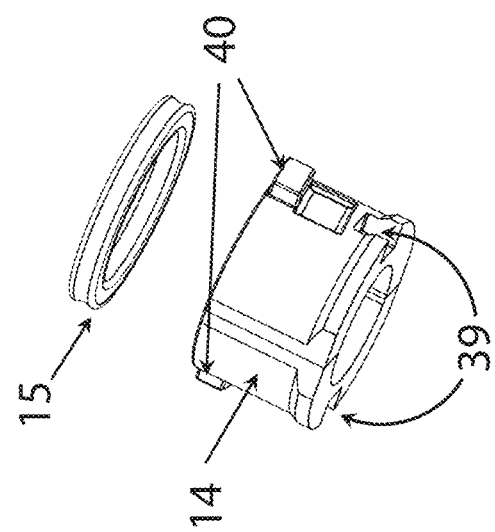

Clip 14 and x-ring 15 may be involved in the attachment of a prefilled syringe 9 to the housing 16 (see FIGS. 9A-9C). The x-ring is placed in cavity 38. In order to attach the syringe 9 to the housing 16, the syringe flange 41 is placed between clip 14 and the housing 16 as it is inserted into cavity 38 such that tabs 39 on the clip 14 are aligned with axial keyways on the housing 16 until ramp slots 37 are reached. Using a torque wrench with adaptor to mate with slots 39, the clip the turned along ramp defined by slots 37 until tight. The prefilled syringe is now secured onto the housing 16 and hence the device.

Mating features 19 and 25 can be used to enable the coarse dose setting dial 12 to be rotationally keyed to dose stop 13, and for the coarse dose setting dial 12 to axially slip relative to dose stop 13. The stop surfaces 18 on dose stop 13 define the end of dose position for the plunger rod dose stop flag 31. Rotation of the fine dose setting dial 11 causes axial translation of the dose stop 13. The end dose position is defined by the axial position of the stop surface 18, which in turn depends on a combination of the volume selected on the coarse dose setting dial 12 and the volume selected on the fine dose setting dial 11. Manipulation of the fine dose setting dial 11 modulates axial position of stop surface 18 corresponding to each setting of the coarse dose setting dial 12. The user is hence able to selectively deploy higher resolution of dose setting or coarse resolution of dose setting or a combination thereof to effectively set a dose volume to be injected. Another dose setting advantage over variable dosing systems such as pen injectors in the prior art is that the user does not have to translate through all the dose levels to set the target dose volume. For example in order to set 0.2 milliliter dose, the user simply has to rotate the coarse dose set dial 12 to set a 0.2 milliliter dose without having to go through 0.01 milliliter increments through to 0.2 milliliter.

Figure 11D:
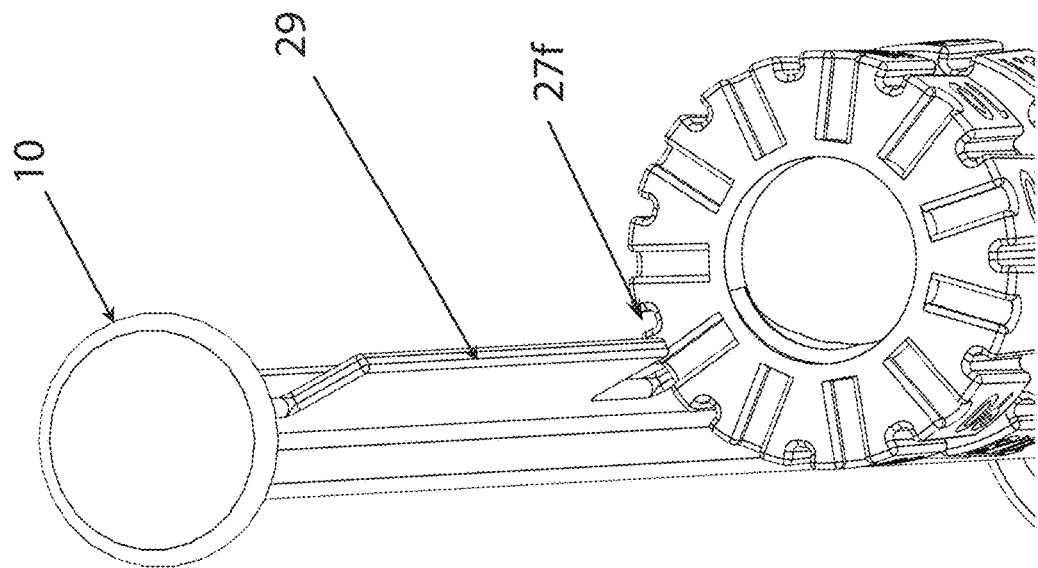
FIG. 11D illustrates a position of a plunger rod relative to a groove, according to various embodiments.
Figure 11A:
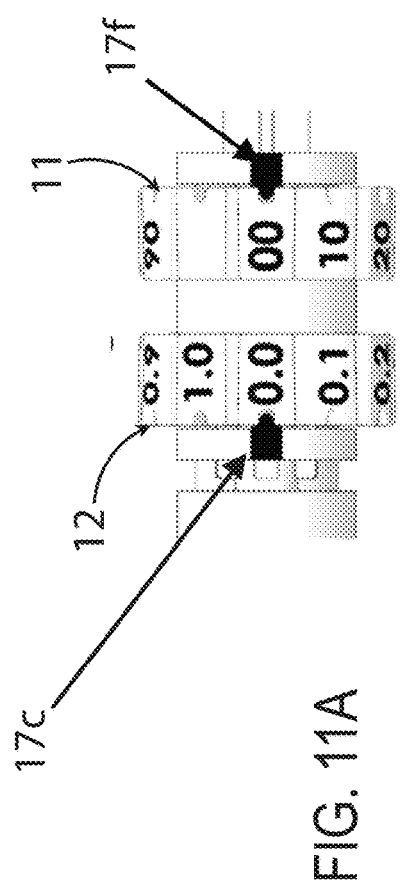
FIGS. 11A-11C illustrate various dose settings, according to various embodiments.
Figure 11B:
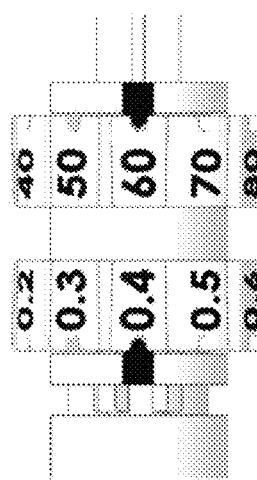
Figure 11C:
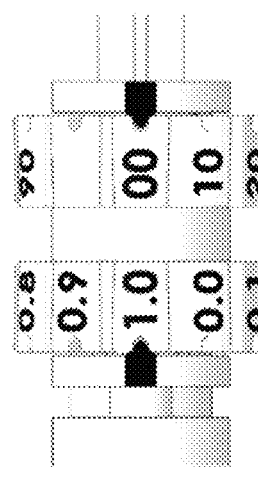

FIG. 11A shows positions of coarse dose setting dial 12 and fine dose setting dial 11 prior to user manipulation to set the dose, according to various embodiments. According to various embodiments, the start of dose position of the plunger rod 10 is defined by abutment between a locking blade 29 of the plunger rod 10 and a proximal end of dial 11, which prevents the plunger rod 10 from being advanced by the user. Markings 17c and 17f on the circular beams on the housing 16 provide the user with a visual reference to set the dose volume based on markings 22 and 26 on the fine and coarse setting dials respectively. Shown in the example of FIGS. 11A, 11B, and 11C are dose volumes set 0.000, 0.460 and 1.000 milliliter injections. Corresponding to when the dose volume is at 0.000, the locking blade 29 of plunger rod 10 is longitudinally misaligned with groove 27f as seen in FIG. 11D. Setting of the dose longitudinally aligns the locking blade with groove 27f The plunger rod 10 is now in the start of dose position.

FIGS. 12A-12F show various aspects of an internal mechanism for dose setting and end of dose for an exemplary 0.440 milliliter injection, according to various embodiments. The internal mechanism involving the fine dose setting dial 11, coarse dose setting dial 12, dose stop 13 and plunger rod 10 corresponding to the state of the device as received by the user is depicted in 'a'. Rotating the fine dose setting dial to align the '40' mark with marking 17f on the housing 16 and rotating the coarse dose setting dial to align the '0.4' with the marking 17c on the housing 16 help rotationally align and axially position the stop surface 18 on dose stop 13; this is shown in 'b'. Shown is 'c' is after the user depresses the plunger rod 10 resulting in axial translation of the plunger rod 10 until the end of dose flag 31 rests against the stop surface 18; this also provides tactile feedback to the user that the intended dose has been delivered. The aforementioned total axial travel is the injection stroke 42.

It may be beneficial to lock the dose setting dials after the end of injection; this option is illustrated in FIGS. 13A-13C. For the same aforementioned 0.440 milliliter example, 'b' in FIG. 13 shows the internal mechanism when the dose is set by the user. After injection stroke 42 is completed, the locking blade 29 axial translates within grooves 27c and 27f of the coarse dose setting dial 12 and fine dose setting dial 11. The presence of the locking blade 29 prevents further rotation of either fine dose setting dial 11 or coarse dose setting dial. This renders the device unusable for delivery of any undelivered drug in the syringe 9 after end of intended dose. The low dose locking blade 30 comes in to play for locking the coarse dose setting dials only for low dose volumes.

Figure 14:
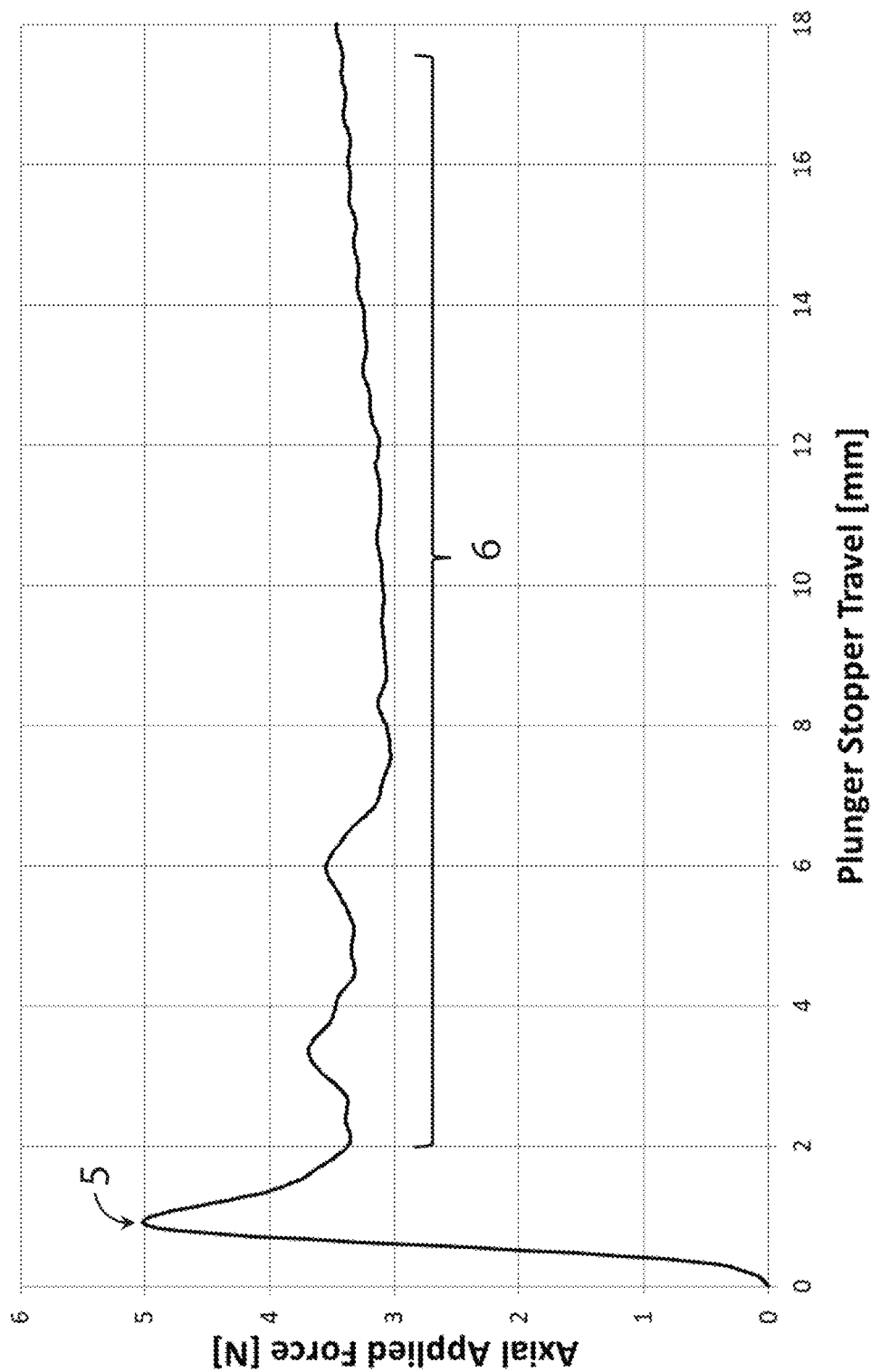
FIG. 14 illustrates an exemplary plunger stop force, according to various embodiments.

In embodiments involving prefilled syringes or prefilled cartridges, a syringe (or cartridge) is stoppered with an elastomeric plunger stopper after the drug is aseptically filled. The plunger stopper is radially oversized relative to the internal diameter of the syringe (or cartridge) to provide and maintain an aseptic barrier. Over time and during storage of the prefilled drug, the elastomeric plunger stopper creates inertia to movement called stiction, where the plunger stopper has to break loose before it axially translates. Shown in FIG. 14 is an exemplary injection force profile illustrating this phenomenon. There are several practical implications of stiction. The increasing amount of axially applied force 5 to overcome stiction can result in loss of user control (due to momentum) over plunger stopper travel. This loss of user control can ultimately result in waste of drug. Increase in force 5 can also trigger occlusion alarms in automated delivery systems such as infusion pumps. Also, shown in FIG. 14 is that the amount of plunger stopper travel corresponding to when stiction comes into play is very small relative to the total expected travel of the plunger stopper to administer the intended drug volume. It is desirable to be able to controllably advance the plunger stopper to overcome stiction before the drug can be shown be advanced by predictable force 6.

Figure 15B:
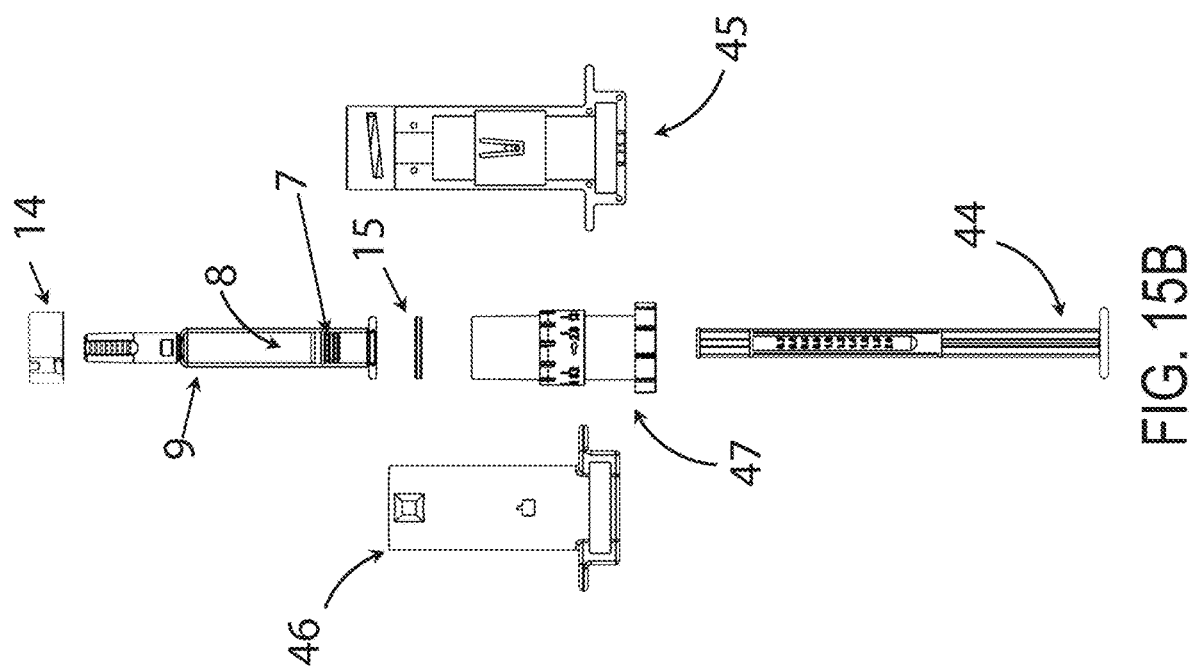
FIGS. 15A-15B illustrate a syringe, according to various embodiments.
Figure 15A:
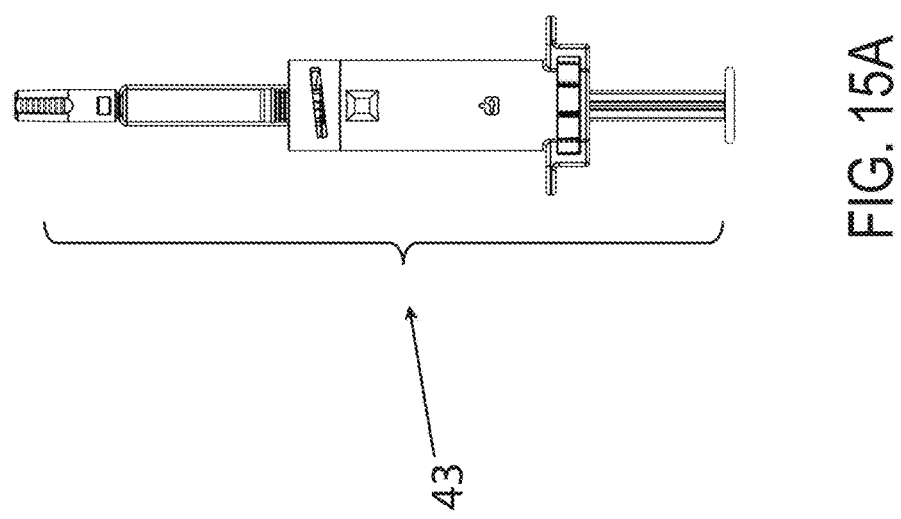

In light of the above, it is desirable in prefilled syringe (or cartridge) base drug delivery applications to have higher resolution of plunger stopper travel to overcome stiction—i.e., reserve higher resolution for amount of plunger stopper travel only to overcome plunger stopper stiction. This can then be followed by providing coarser resolution for other preset dose volume amounts. Pre-setting dose levels is only possible when the various dose amounts are known beforehand for the given injectable drug 8. FIGS. 15A-15B illustrate a variable dosing syringe 43 that can overcome plunger stopper stiction and provide fine and coarse resolution, according to various embodiments. Syringe 43 can be used, for example, to deliver a minimum of 0.2 milliliter and a maximum of 2.0 milliliters in increments of 0.2 milliliter (i.e., 10 dose volume levels—0.2, 0.4, 0.6, 0.8, 1.0, 1.2, 1.4, 1.6, 1.8, 2.0 milliliters). It should be understood that these delivery amounts and increments are merely exemplary and the syringe 43 can be configured to deliver any suitable amounts and increments.

Syringe 43 includes a plunger rod assembly that can be assembled to a syringe 9. The plunger rod assembly can include plunger rod 44, housing 45, cover 46 and dose setter 47 (also referred to herein as a dose set dial 47). The illustrated embodiment incorporates a prefilled syringe 9 containing injectable drug 8 stoppered with plunger stopper 7. This is prefilled syringe 9 is secured to the housing 45 using a clip 14 and elastomeric x-ring similar to syringe 100 of FIG. 2.

Plunger rod 44, according to various embodiments, is shown in FIGS. 16A-16B. Patient end of the plunger rod 44 contains a disc 48 to allow the user to manually advance the plunger rod 44 after the dose is set. The cylindrical patient end 49 abuts the plunger stopper 7 upon assembly. This end 49 can also be modified to have threads to interlock with the axial, non-drug contacting side of the plunger stopper 7. A drag latch 47 may be employed to provide control of axial plunger rod 44 travel. The plunger rod 44 contains four longitudinal ribs 50, which along with features on the housing 45 and cover 46 help prevent rotation of the plunger rod 44 during device operation. Flag 51 consists of a high-resolution drive surface 52 on the non-patient end, and a stop surface 53 on the patient end. The plunger rod 44 also consists of a beam 54 which helps provide an audible end of dose indication, and axially locks the plunger rod 44 once selected dose is completely delivered (end of dose). The plunger rod 44 also consists of a flat surface with end of dose markings 55 corresponding to various deliverable dose volumes. Spacing of the dose volume markings corresponds to injection strokes for the respective dose volumes.

Housing 45, according to various embodiments, is illustrated in FIGS. 17A-17F. It consists of a dose setting clicker ratchet 56. Portions 57 of flanges for user to hold the device during injection are provided. Cavity 58 radially constrains plunger rod 44. Side slot 59 is provided to allow user access to dose set dial 47. Axial slots 60 provide alignment for insertion of tab 40 on clip 14 during insertion of syringe 9 prior to attachment. Slots 61 provide ramped slots for tabs 40 upon rotation of clip 14 to securely attach syringe 9 to the housing 45. Detailed in FIGS. 18A-18D is clicker 56, according to various embodiments, shown consisting of a hemispherical peg 63 and clicking peg 62. The height of hemispherical peg is slightly greater than the height of clicking peg 62. Clicker 56 provides tactile and audible feedback to the user during dose setting, and interacts with features on the dose set dial 47 contained within a recessed cylindrical section 66 of the housing 45. Surfaces 64 and 65 help axially constrain the dose set dial 47.

The dose set dial 47, according to various embodiments, is shown in FIGS. 19A-19E. Dose set dial 47 includes a rotatable body that has a plurality of dose stops 76 that engage the flag 51 of the plunger rod 44 to stop axial travel of the plunger rod 44 to control the end of the dose delivery. Portion 67 of the dose set dial 47 are contained within section 66 of the housing 45. Dose markings 68 are printed to enable the user to select the injection volume (dose setting). Part of the markings 69 includes an '→' marking indicating to the user initial direction of rotation of the dose set dial 47. Only one of these markings 68 is visible to the user through cover 46. Surface 69 rests against surface 64 of the housing 45 axially constraining the dose set dial 47 towards the patient end. Surface 70 is constrained by surface 65 of the housing 45, hence constraining the dose set dial 47 in the non-patient end direction. The dose set dial 47 consists of a number of longitudinal splines 71. Constrained within these splines 71 is the flag 51 of the plunger rod 44. Longitudinal grooves 72 on portion 67 of the surface of dose set dial 47 interact with pegs 62 and 63 of the clicker 56. Among them, grooves 72a, 72b and 72c are longer than the other grooves to accommodate both pegs 62 and 63. Remainder of the grooves 72 accommodate only peg 63. Pegs 62 and 63 are in groove 72a when unused. The shape of groove 72a ensures rotation of dose set dial 47 only in the direction indicated by '→' part of marking 68. After rotating dose set dial 47 by an angle corresponding to 74, and upon reaching groove 72b, the dose volume is set at 0.2 milliliter. The shape of groove 72b (identical to shape of 72a) prevents the user from going back to '→'; this groove 72 accommodates both pegs 62 and 63. Continued rotation towards other hemispherical grooves 72 engages only the hemispherical peg 63. The hemispherical shape of the other grooves 72 allows bi-directional rotation of dose set dial 47 except at those corresponding to 0.2 and 2.0 milliliter. This arrangement prevents a transition from either 2.0 milliliter to the '→' location or transition from 0.2 milliliter to '→' location, but at the same time allowing flexibility to the user to go back and forth between other dose levels prior to injection. Side slot 73 provides and defines the fine resolution for this embodiment. This slot constrains flag 51 of the plunger rod 44. When the device is unused, the flag 51 is at location 75a. Surface 52 of flag 51 contacts surface 73a. Upon rotation of dose set dial 47, flag 51 axially translates by a distance 75 to location 75b. There is more axial constraint on stop surface 53 on plunger rod 44 once the flag 51 reaches 75b. The plunger rod 44 is in the axial start of dose position for any of the dose volumes settable with this embodiment. The dose at this rotational position of the dose set dial 47 is set at 0.2 milliliters in this example. Distance 75 is fine resolution of axial translation of plunger rod 44 that helps overcome stiction of plunger stopper 7, and also in some instances help prime the delivery conduit such as an injection needle. The end of dose position is defined by surfaces 76, which are axially separated based on injection stroke corresponding to dose volume selected by the user by rotation of dose set dial 47. The surface 76 corresponding to the user set dose volume longitudinally aligns with stop surface 53 on the plunger rod 44. Plunger rod 44 is contained within cavity 78.

Figure 20:
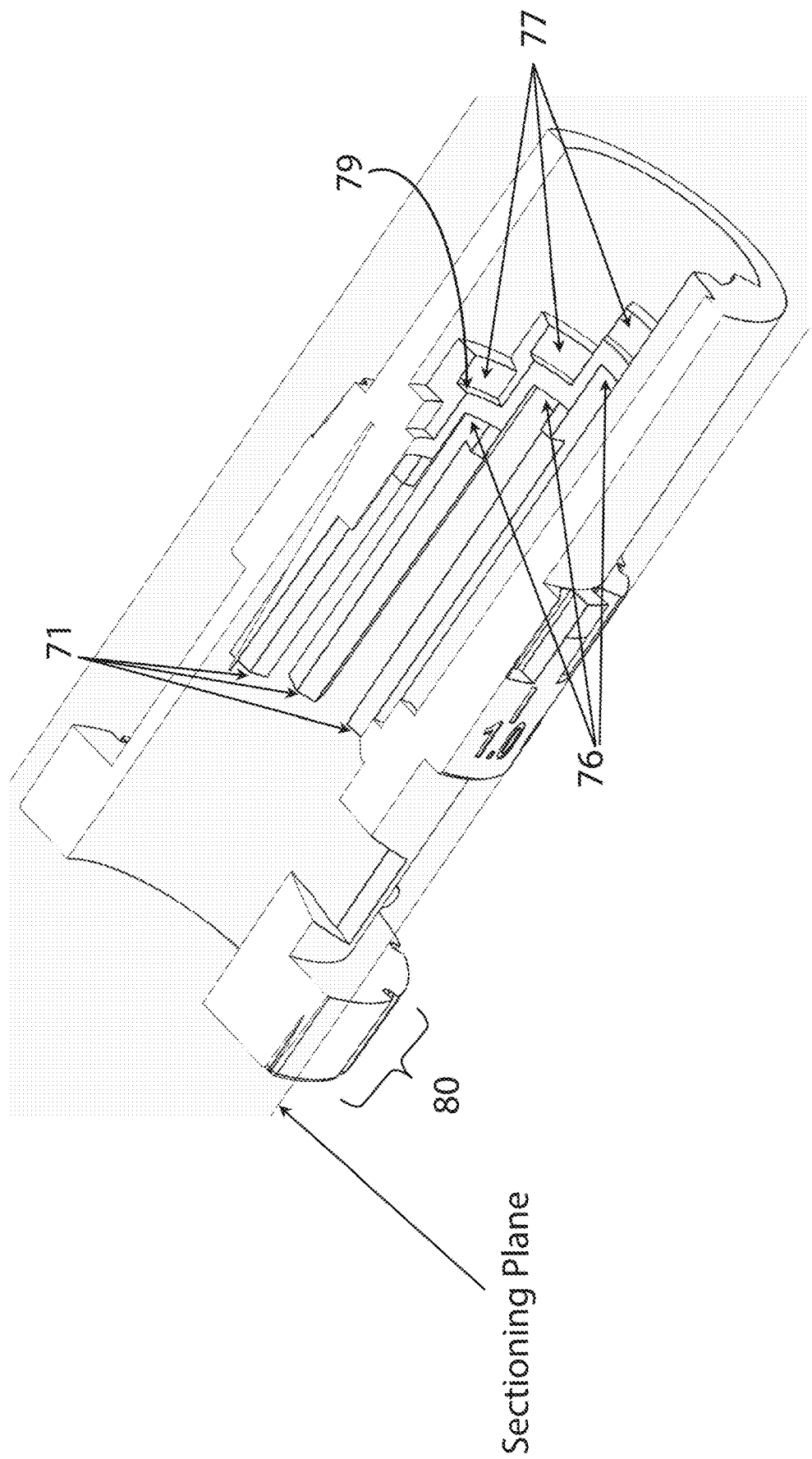
Figure 21:
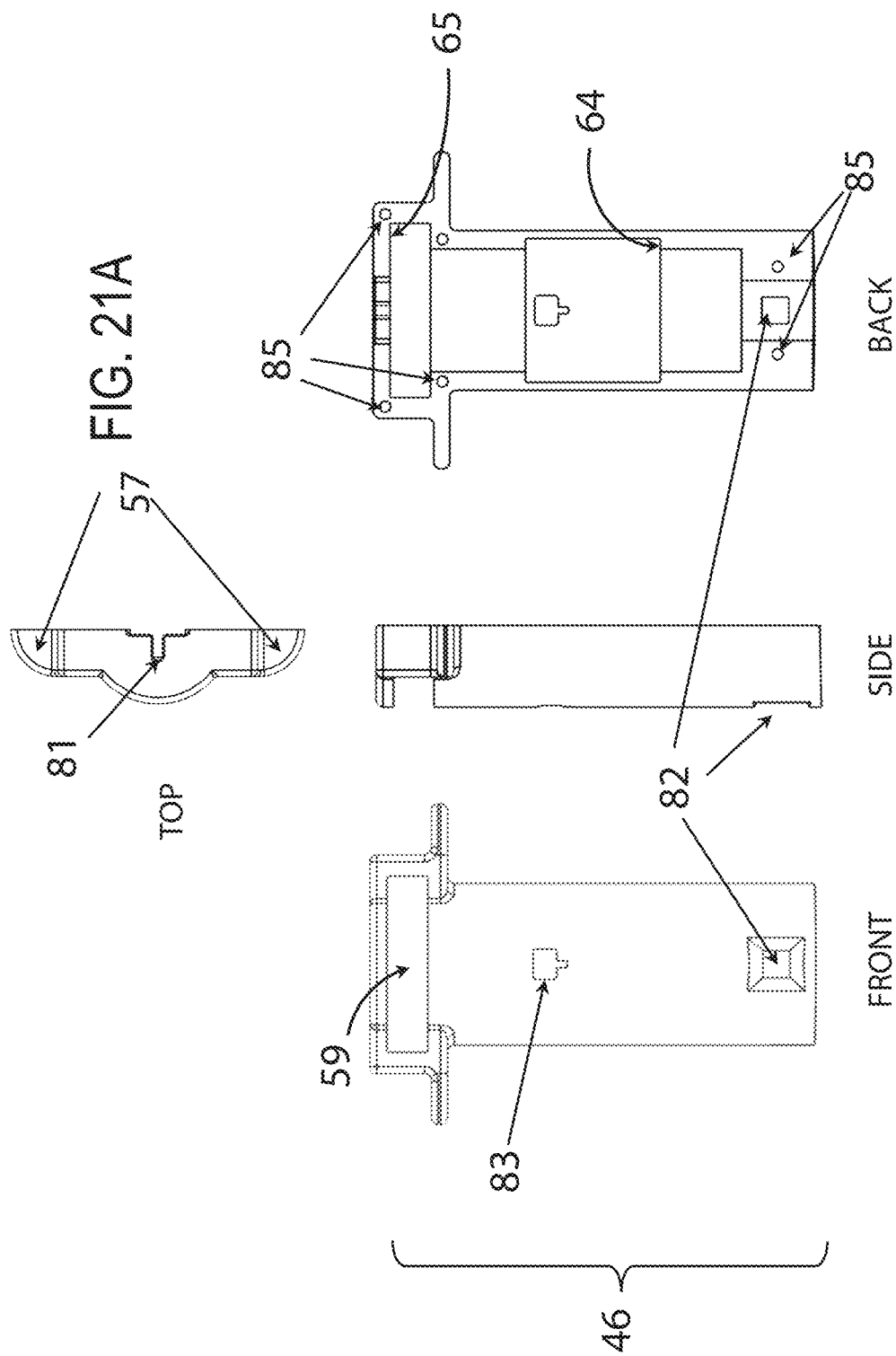
FIGS. 21A-21D and 22 illustrate a cover, according to various embodiments.

FIG. 20 provides a cross section view of features on dose set dial 47. Surface 77 engages tip of beam 54 of the plunger rod 44. At the end of dose, beam 54 hits surface 77 to provide an audible end of dose indication. Surface 79 engages beam 54 such it is axially locks plunger rod 44 in the non-patient direction at end of dose. Hence, at end of dose, the plunger rod is axially locked in the patient direction by engagement of surfaces 53 and 76 and in the non-patient direction by interaction of beam 54 and surface 79. The user interface 80 on dose set dial 47 to rotate it may contain striations or textures for gripping. Unlike the previous embodiment shown in FIG. 2, the fine resolution travel and dose stops are encoded onto the dose set dial 47.

The interaction between surfaces 73a and 52 is analogous to portion of the fine resolution travel adjustment between threads 21 and 20 in syringe 100 in FIG. 2. The coarse dose setting interactions between surfaces 53 and 76 are analogous to features 18 and 31 for embodiment in FIG. 2.

Figure 22:
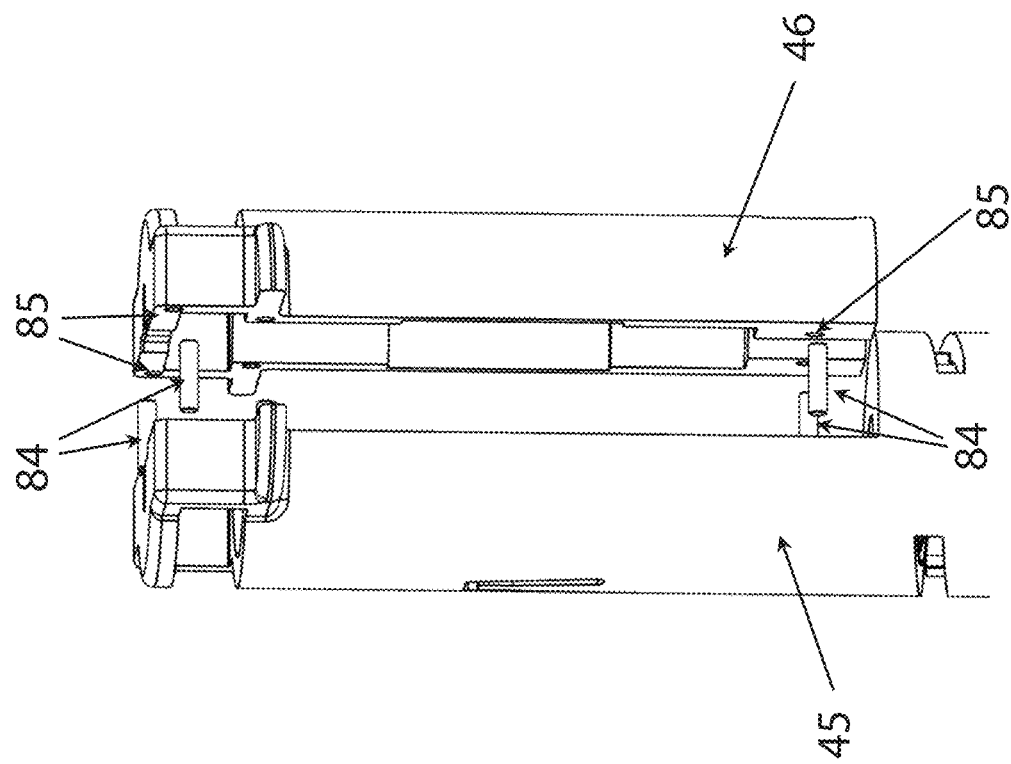

The device cover 46, according to various embodiments, is shown in FIGS. 21A-21D. It contains the other half of flange 57 and slot 59 for dose set dial 47. Surfaces 64 and 65 along with those in housing 45 internally provide axial constraint to the dose set dial 47. Slot 81 on the top surface engages rotationally constrains ribs 50 of plunger rod 44. Since the plunger rod 44 is axially locked when end of dose is reached, rotational locking of the plunger rod 44 by slots 81, prevents rotation of dose set dial 47 since its splines 71 are rotationally keyed with flag 51 of the plunger rod 44. Hence, at end of dose in addition to the plunger rod 44 being axially locked, the dose set dial 47 is rotationally locked thereby disabling the device and preventing reuse even though some amount of undelivered drug 8 remains in the syringe 9 contained within the device 43. At the end of dose, window 82 provides visibility to the markings 55 corresponding to the dose volume injected. During dose setting, only the marking 68 corresponding to the dose volume set is made visible to the user through window 83. Upon receipt of device 43, the user sees '→' in window 83. Pinholes 85 are used during assembly as shown in FIG. 22. Dowel pins 85, that are slightly oversized (radial) relative to pinholes 85 are used to assemble the cover 46 onto the housing 45. The dowel pins 85 can also be incorporated as posts and molded as part of either cover 46 or housing 45.

Figure 23:
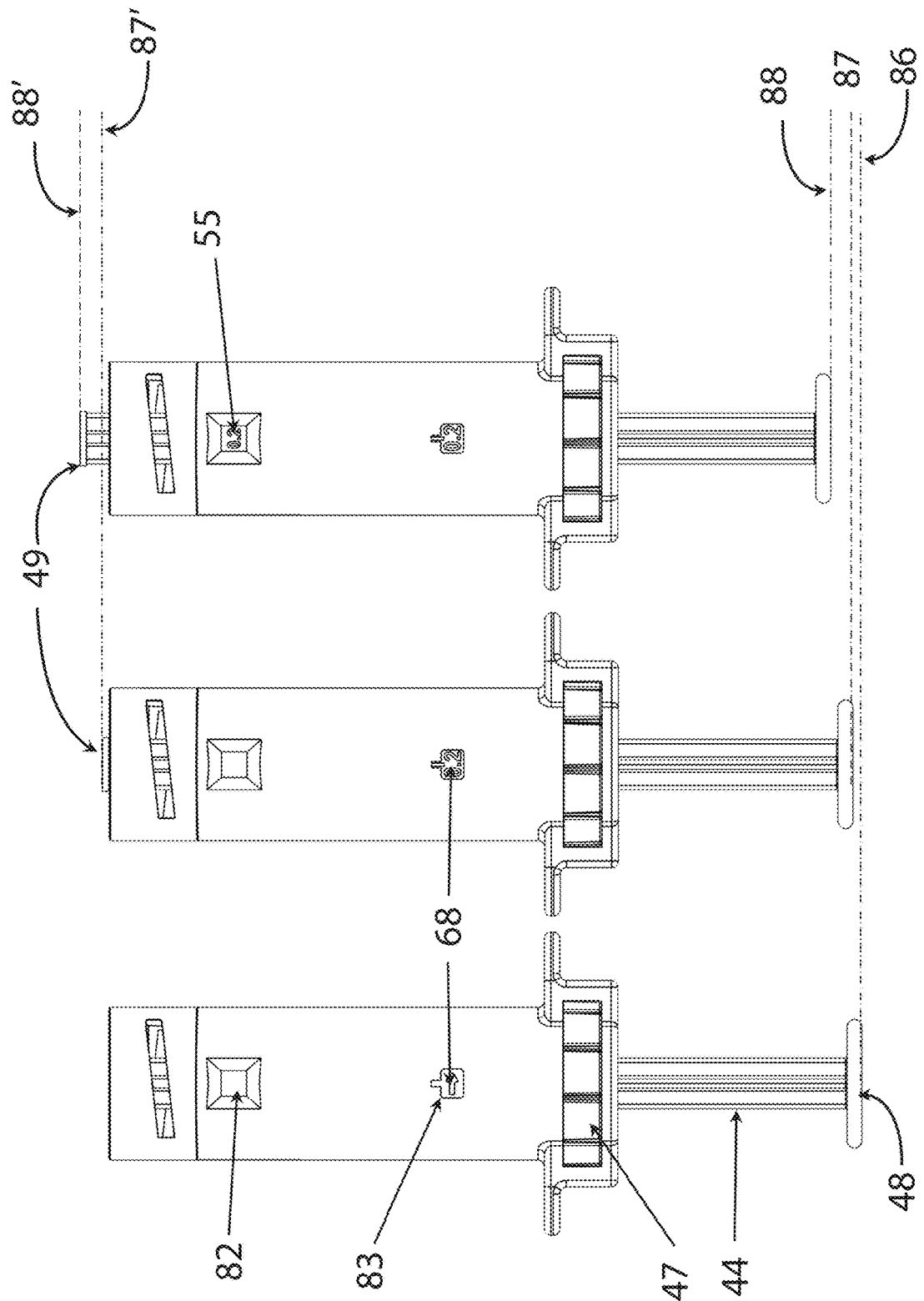
FIGS. 23A-23C illustrate a process for setting and delivering a dose, according to various embodiments.

Device operation to set and deliver a 0.2 milliliter dose is shown in FIGS. 23A-23C. Device as received by the user is depicted in 'a'. The '→' is visible in window 83. The corresponding plunger rod 44 axial position is shown as '86'. The user rotates dial 47 in the direction indicated by the '→' marking 68. Once the dose set dial is rotated by angle 74, the dose volume is now set to '0.2' milliliters (depicted in 'b'). The corresponding plunger rod 44 axial position 87 is the start of dose position. Once the delivery conduit, such as a needle is in the injection site, the user then depresses plunger rod 44 using disc 48 until the plunger rod 44 cannot translate any further; this is the end of dose position depicted by 88. At this position, marking 55 is also visible in window 82 providing a visual end of dose indication to the user. At the end of dose the markings 68 and 55 are the same dose volume amount. Positions of patient end 49 of plunger rod 44 at beginning of dose 87' and end of dose 88' are also shown. The difference in axial positions between 88 and 87 and between and 88' and 87' are identical and represent the injection stroke for the dose set by the user, which in this case is 0.2 milliliters. The distance traversed between plunger rod 44 position 86 and position 87 is the fine resolution travel that helps overcome stiction of plunger stopper 7. This travel is the same as 75 shown in FIGS. 19A-19E. In some cases, this fine resolution travel can also help prime the delivery conduit to minimize risk of underdosing.

Figure 24:
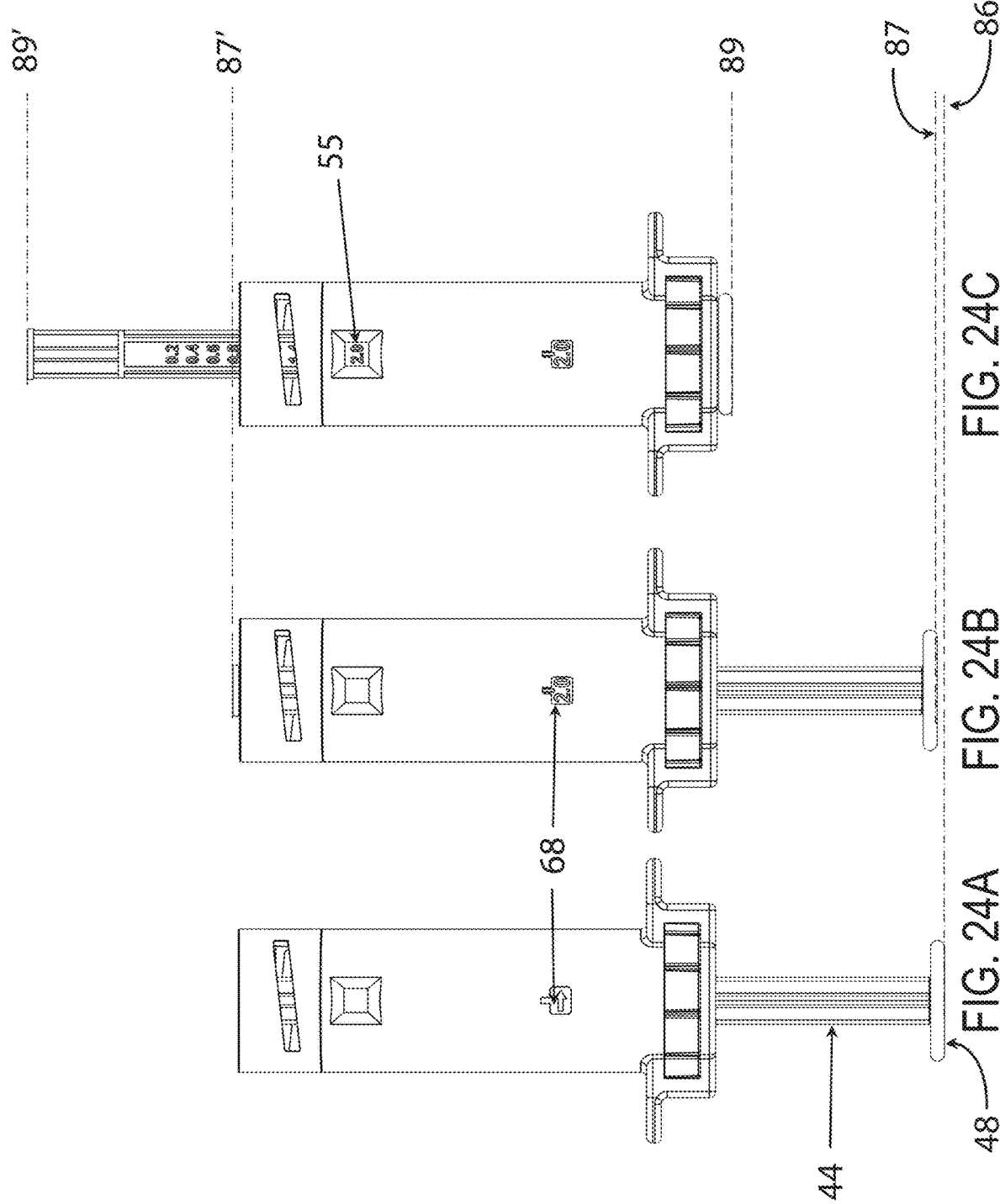
FIGS. 24A-24C illustrate a process for setting and delivering a dose, according to various embodiments.

FIGS. 24A-24C illustrate operation of the device to set and deliver a 2.0 milliliter dose, according to various embodiments. Even when dose is set at 2.0 milliliters, the corresponding start of dose position 87 is the same as that when a 0.2 milliliter dose is set; this is true also for all other dose volumes in between. The end of dose position corresponding to the 2.0 milliliter dose is depicted by 89, and corresponding position of patient end of plunger rod is 89'. Axial difference between 89 and 87 and 89' and 87' is the injection stroke for a 2.0 milliliter dose in syringe 9.

Figure 25:
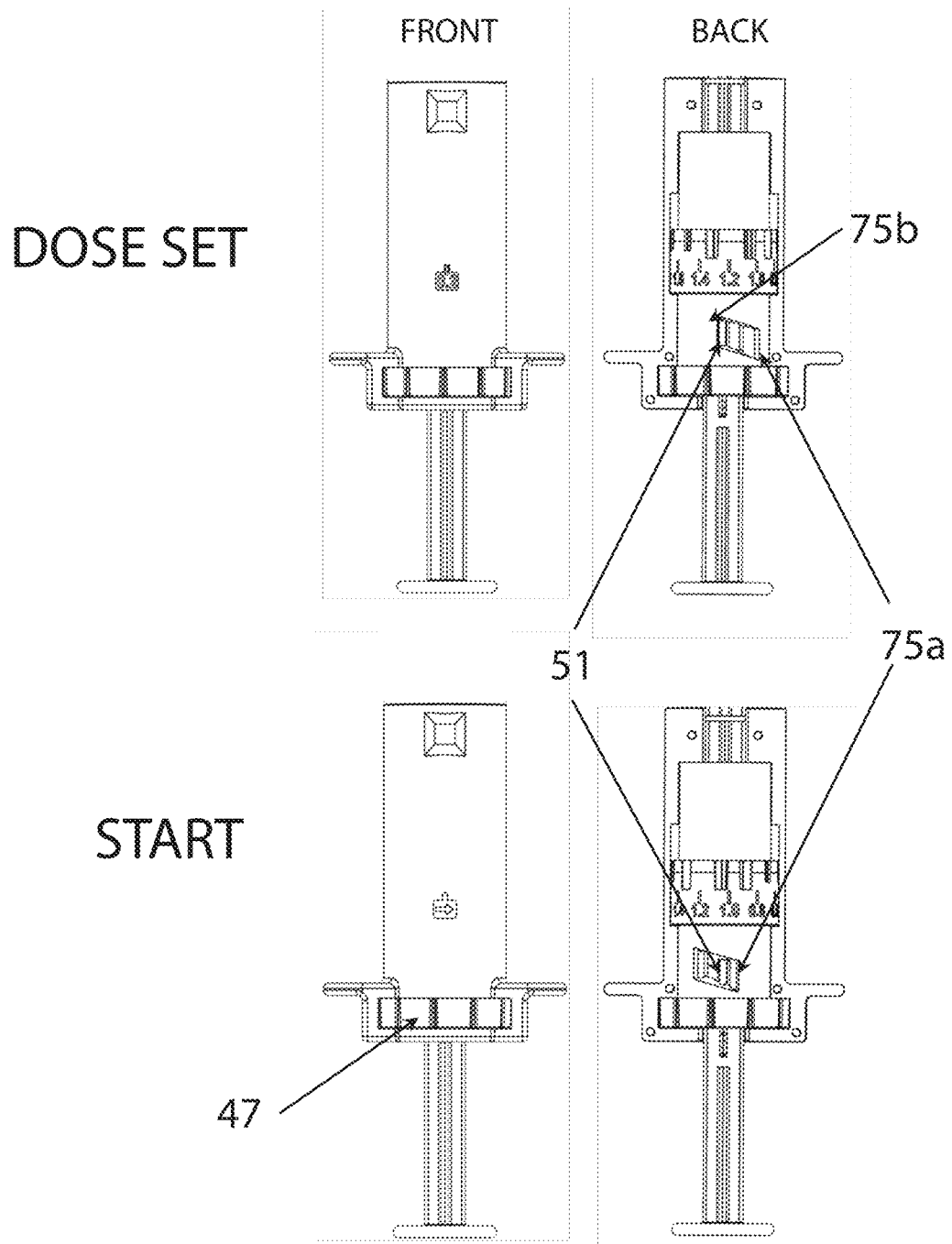
FIG. 25 illustrates a fine resolution plunger rod travel, according to various embodiments.

FIG. 25 further illustrates fine resolution travel to overcome stiction of plunger stopper 7 (and potential priming). Front and back (without showing housing) views show how rotation of the dose set dial 47 causes flag 51 to move from 75a to 75b resulting in higher resolution of axial travel 75 (shown in FIGS. 19A-19E).

Figures 26A, 26B, 26C:
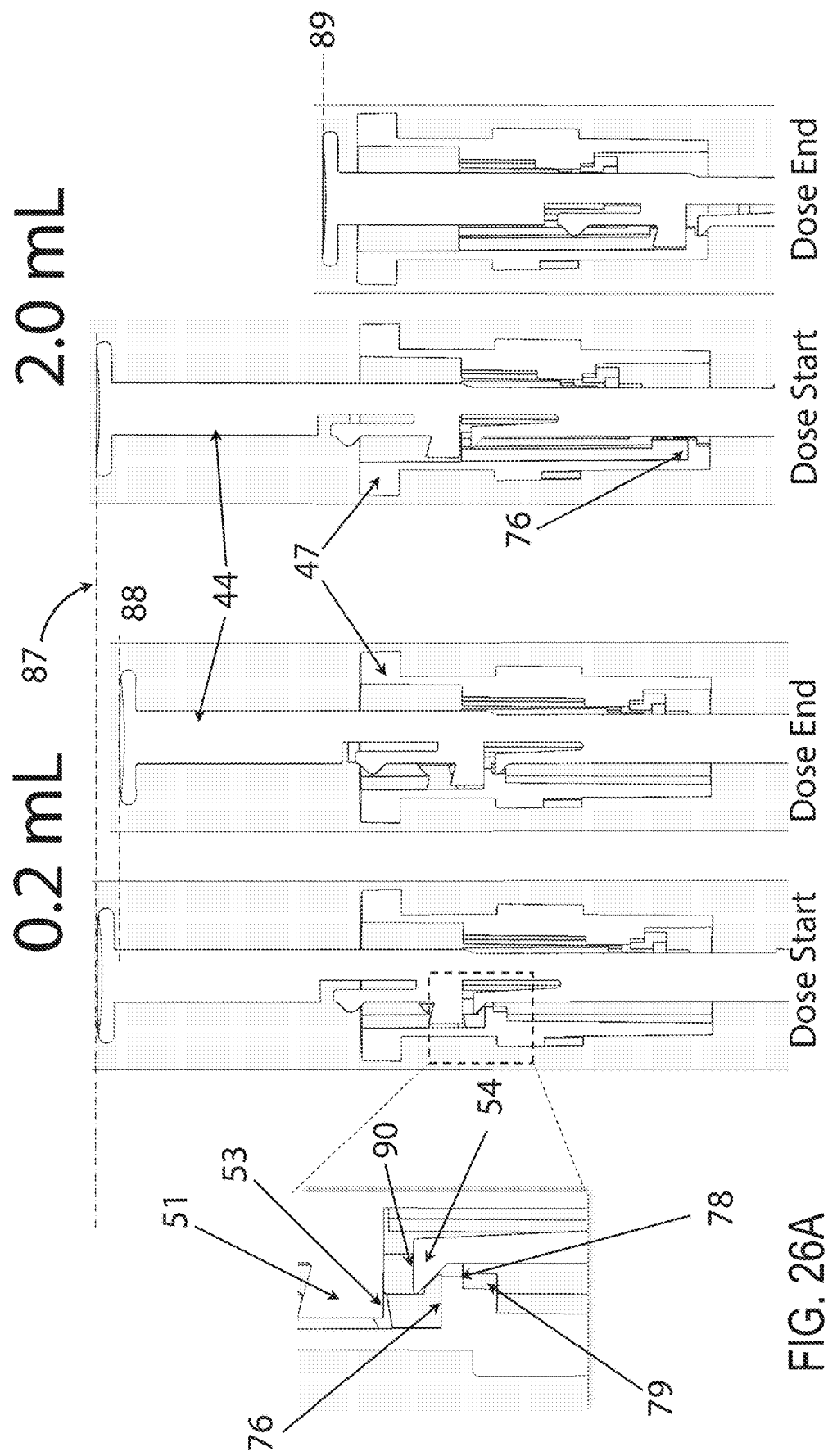
FIGS. 26A-26C illustrate plunger rod travel for two different dose settings, according to various embodiments.

Section views in FIGS. 26A-26C illustrate device operation (dose start and dose end) to deliver an exemplary 0.2 milliliter dose and 2.0 milliliter dose, according to various embodiments. When a 0.2 milliliter dose is set, then plunger rod 44 flag 51 and beam 54 are longitudinally aligned with the end of dose position 76 corresponding to the 0.2 milliliter dose volume. The plunger rod 44 position here is 87. When the user depresses the plunger rod 44, the plunger rod 44 axially translated until stop surface 53 reaches end of dose position 76. Concurrently, beam 54 deflects onto surface 79. Surface 90 of beam 54 is axially constrained in the non-patient direction by surface 78. The user rotation of dose set dial 47 to set a 2.0 milliliter dose until the rotational position of the end of dose position 76 corresponding to the 2.0 milliliter dose is longitudinally aligned with the stop surface 53 of the plunger rod 44.

Figure 27C:
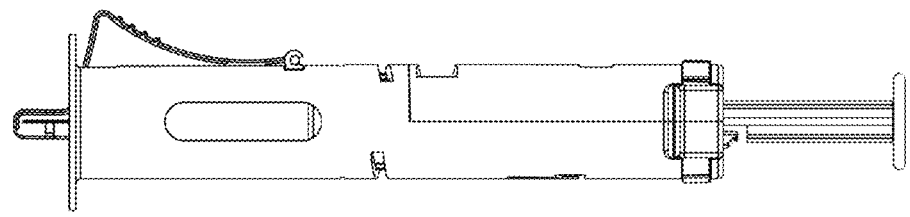
Figure 27B:
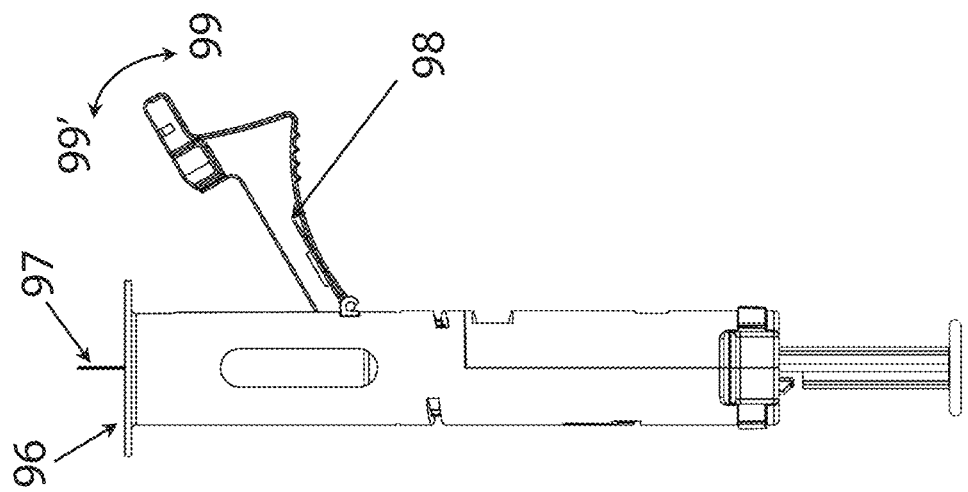
Figure 27A:
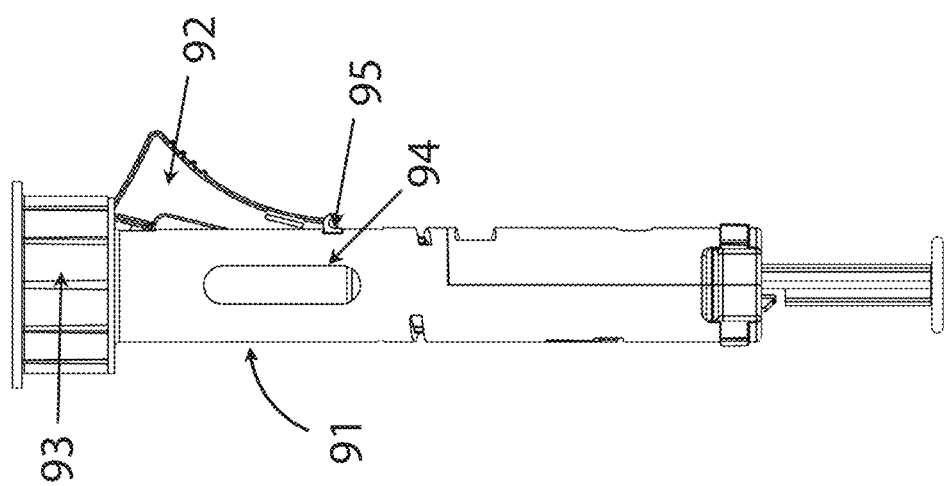

In order to protect the syringe 9 incorporated into the device, it may be desirable to include a cover. In addition, to minimizing risk of needlestick injuries and to comply with regulations (or facilitate at-home injections) it is desirable to incorporate a safety mechanism to shield the needle after use. An exemplary cover 91 is illustrated in FIGS. 27A-27C. The syringe cover 91 can be an extension of the housing 45, with diametrically opposite windows 94 to enable the user to inspect the drug in the syringe 9 prior to injection. Needle safety clip 92 pivots about a hinge 95. The needle safety clip is aligned as shown in 'a' when the user receives the device with enclosed drug. When the cap 93 is removed (shown in 'b'), a spring beam 98 moves the needle safety clip 92 in direction 99. Surface 96 ensures that the angle of insertion of needle 97 is perpendicular to the injection site to ensure correct depth of exposed needle insertion. Once the injection is completely administered and the device is removed from the injection site, the user can push the needle safety clip 92 in direction 99' until it locks with the needle 97 (shown in 'c'). The tip of needle 97 is now completely encased within the safety clip 92. Shown in FIG. 28 is latch 100 that grabs the needle 97 preventing exposure to the used needle 97.

Unlike syringe 100 shown in FIG. 2, syringe 43 includes sequential deployment of fine resolution and coarse resolution. Syringe 43 described herein involves higher resolution first followed by various dose levels (coarse resolution) defined by end of dose position 76. Also syringe 43 is illustrated herein as having are 10 dose volume levels. However, various embodiments including fewer than 10 or more than 10 dose levels are included within the scope of this disclosure.

According to various embodiments, coarse resolution can be deployed prior to fine resolution of plunger rod 44 travel. This would be pertinent in applications where the delivery conduit has a large dead space—for e.g., delivery using a catheter tubing and the dose volume is very small relative to the volume necessary to prime the catheter. In this case, when dose set dial such as 47 is set to prime position, end of dose position 76, which is at a distance corresponding to the stroke needed to priming volume is longitudinally aligned with the stop surface 53 of the plunger rod 44. This priming stroke is the coarse resolution. At the end of priming stroke, there is no locking of beam 54. There is also no spline 71, allowing rotation of dose dial 47 at the end of priming to set the desired dose volume. Axial position of end of dose position 76 for the small dose provides the fine resolution.

Also, envisioned are embodiments where sequential delivery of several equal or unequal volumes is desired. This can be achieved by removing the splines 71 in dose set dial 47 in syringe 43 are removed to achieve sequential delivery of several equal or unequal volumes.

Various embodiments described above have fine and coarse resolution encoded into the dose set dial 47. Shown in FIGS. 29A-29B, according to various embodiments, is syringe 101 where the fine and coarse resolution is encoded onto a plunger rod 102 and the stop surface conversely to embodiment 43 is on a dose set dial 103.

Syringes 100 and 43 discussed above can have the fine and coarse resolution for dose volumes and plunger rod travel encoded onto the dose setting dial. Alternatively, the fine and coarse resolution for dose volumes and plunger rod travel can be encoded onto a plunger rod, as described below with respect to syringe 101 illustrated in FIGS. 29A-29B. Syringe 101 can include a plunger rod assembly attached to a syringe 9. The plunger rod assembly can include a plunger rod 102, a dose setter 103 (also referred to herein as a dose setting dial 103), cover 104, housing 105, end of dose drum 106, disc 107, window covers 108. The illustrated embodiment incorporates a prefillable syringe 9 filled with an injectable drug 8, which is enclosed by an elastomeric plunger stopper 7. The syringe has a pre-attached (staked) needle 97 as a delivery conduit. This filled syringe is secured to the device using a clip 14 and elastomeric x-ring 15. Embodiment 101 is illustrated to deliver a minimum of 0.2 milliliters and a maximum of 2.0 milliliters in increments of 0.2 milliliters for a total of 10 dose volume levels.

Figure 29B:
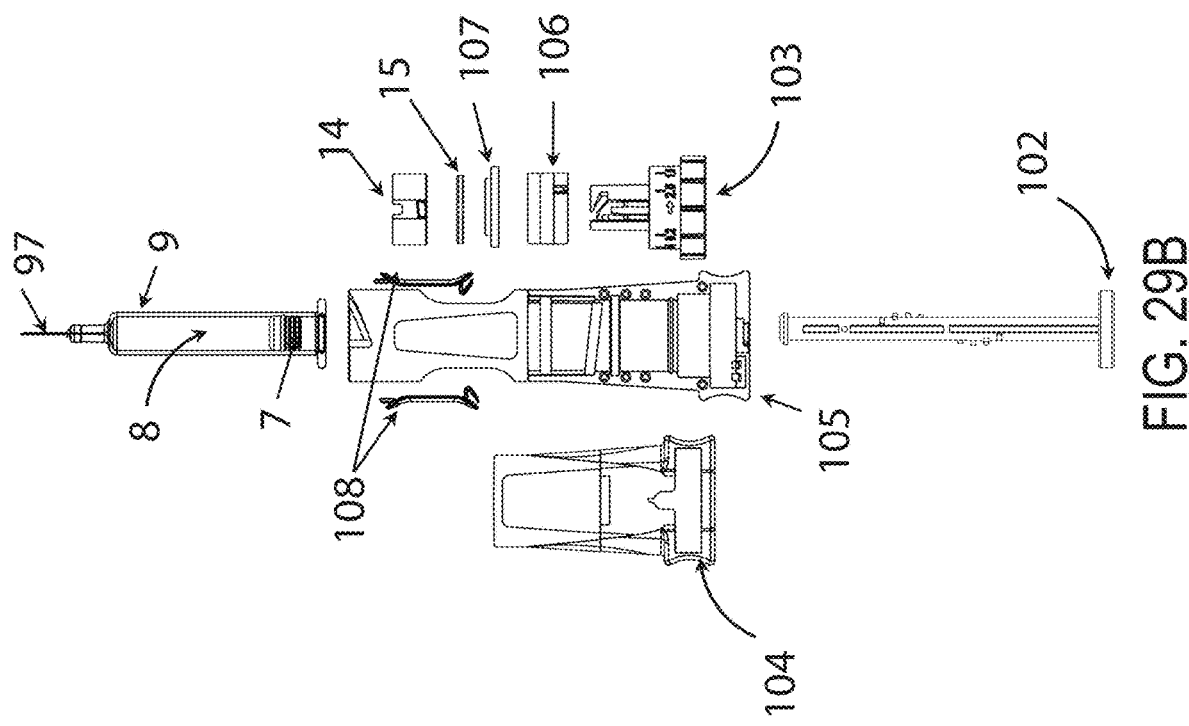
FIGS. 29A-29B illustrate a syringe, according to various embodiments.
Figure 29A:
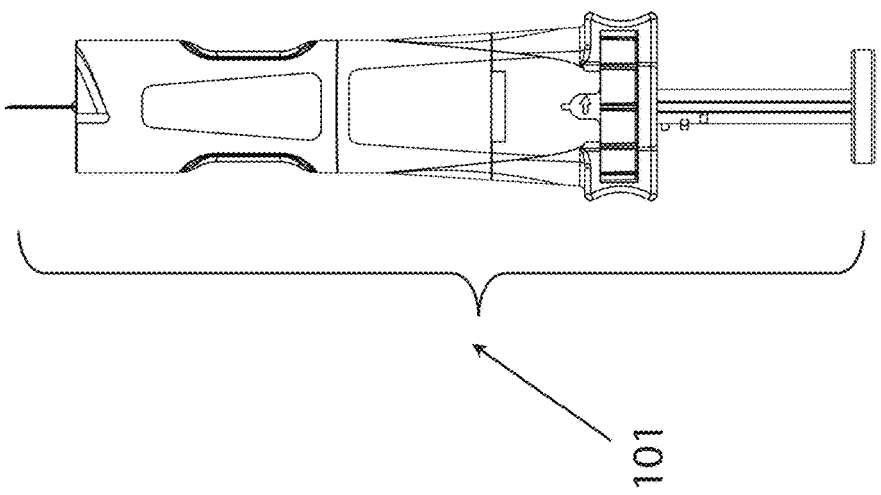
Figures 30A, 30B:
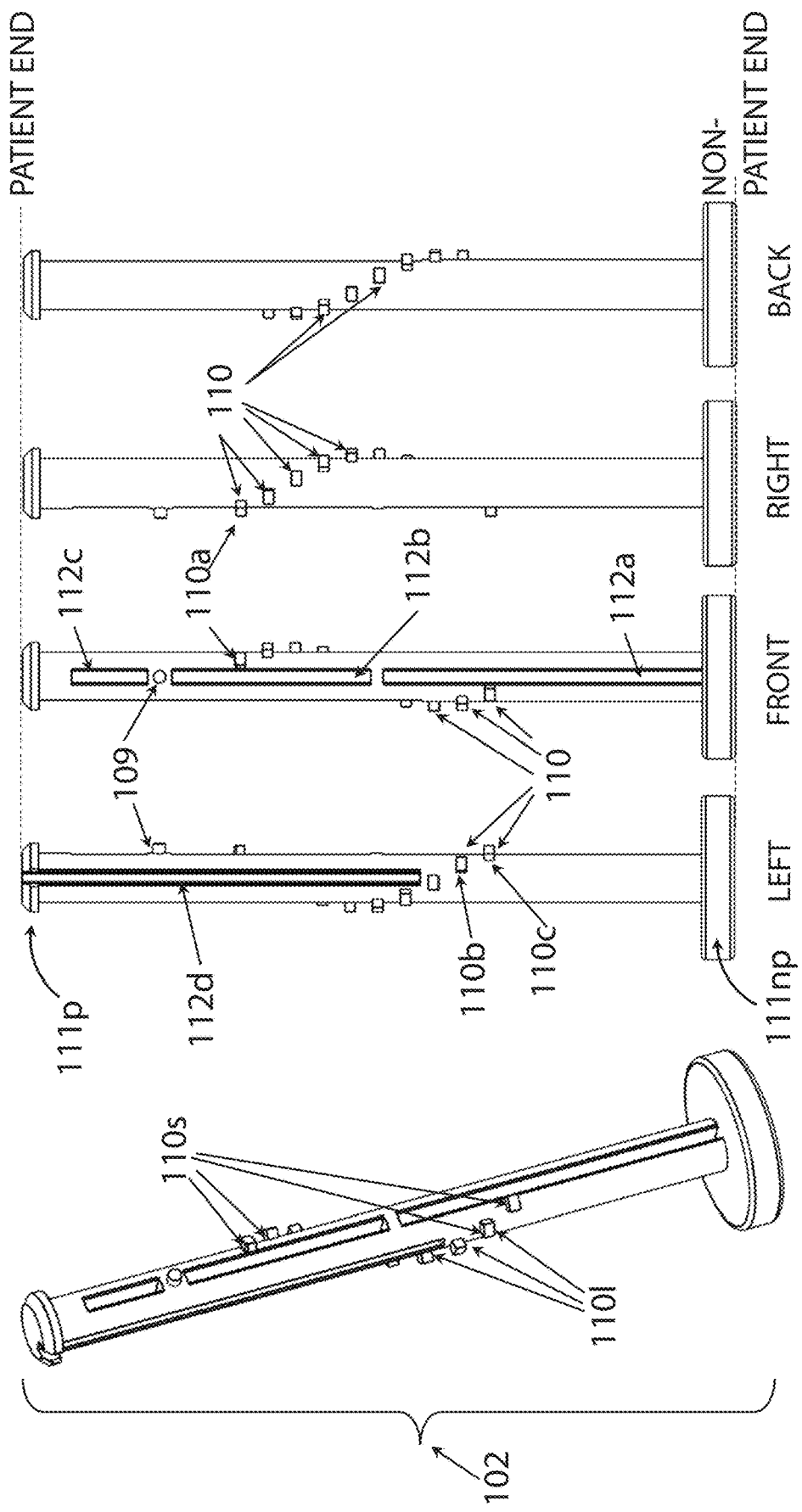
FIGS. 30A-30B illustrate a plunger rod, according to various embodiments.

The plunger rod 102 for the embodiment in FIGS. 29A-29B includes patient end 111p and non-patient end 111np (see FIG. 30). The user axially depresses the circular disc 111np to administer a dose. Plunger rod 102 consists of cylindrical fine resolution peg 109 and a number of pegs 110 corresponding to the various dose volumes that can be set and injected using this device 101. Peg 110a corresponds to the lowest deliverable dose volume and peg 110c corresponds to the highest deliverable dose volume. Also shown in FIGS. 30A-30B are axial slots 112d and 112a, both of which help prevent rotation of the plunger rod 102 during device operation. Slots 112b and 112c help improve manufacturability of plunger rod 102. The peg 110 surfaces 110s are involved with the end of dose. Peg 110 surfaces 1001 are involved with axial locking of the plunger rod 102 in the non-patient direction after end of dose is accomplished. FIGS. 31A-31B show modifications to plunger rod 102 within the scope of device 101. Fine resolution peg 109a may have a flat surface and the patient end 111p-a of the plunger rod 102 may have a flat surface (as shown in FIGS. 31A-31B) contacting plunger stopper 7 compared to 111p on plunger rod 102. It is possible that this end of the plunger rod may have other modifications to engage with plunger stopper 7.

Features of dose set dial 103 are detailed in FIGS. 32A-32D, according to various embodiments. The dose set dial 103 includes a rotatable body that includes a first stop that has a surface 118a that defines a start of dose delivery position of the plunger rod 102 and a second stop having surface 122a that defines an end of dose delivery position of the plunger rod 102. The dose set dial 103 can include three segments—user contacting and dose setting 113, dose volume referencing 114 and end of dose apparatus 115. Markings 116 providing the user with visual aid on dose volume to be set are printed on the cylindrical segment 114. Dose set dial 103 has an axial cavity 117 within which plunger rod 102 is placed. End of dose apparatus 115 consists of portion of a cylinder 114s with features on the cylindrical surface extending radially towards the axis of the dose set dial 103. Through side slots 118 and 119 exist on cylinder 114s. Slot 118 engages the fine resolution peg 109 (or 109a). Surface 118a contacts the surface on peg 109 on its non-patient side. Slot 119 is compartmentalized by beam 120 into primary end of dose slot 121e, start of dose slot 121s and secondary end of dose slot 122. When the user selects and sets a dose volume for injection, the peg 110 corresponding to the selected dose volume on plunger rod 102 is longitudinally aligned with slot 121e. Except for the lowest dose volume setting and in all other dose volumes set by the user, the peg 110 corresponding to a dose amount immediately lower than the one selected by the user is longitudinally aligned with secondary end of dose slot 122. At the end of delivery of this aforementioned, user selected dose volume, the aforementioned peg corresponding to the immediate lower volume is contained in and constrained within secondary end of dose slot 122 and axially constrained by surface 122a. Deflection of beam 120 immediately prior to end of dose by peg corresponding to dose volume selected and its subsequent return to position illustrated in FIGS. 32A-32D provides the audible end of dose indication. The user is able to rotate the dose set dial 103 by manipulating the user contacting and dose setting segment 113. The bottom of dose set dial 103 has features for control and alignment of dose setting dial. Rectangular groove segments 124 each correspond to different dose volumes that can be set using this embodiment; there is also one rectangular groove segment 124a corresponding to the '→' marking 116. Groove 124b corresponds to the lowest injection volume (0.2 milliliter) and groove 124c corresponds to the highest injection volume that can be set (2.0 milliliter) in the embodiment 101 illustrated here. Circular groove segment 123 covers the cumulative rotational angle traversed by the dose set dial 103 between the lowest dose volume and the highest dose volume, i.e., the angle between 123b and 123c. 123a corresponds to the position of the '→' marking 116. Ramp 125 enables beam 138 on the housing 105 to traverse from the within the groove starting at 123a to outside the groove. The interaction between surface 118 and 109 is analogous to portion of the fine resolution travel adjustment between threads 21 and 20 in embodiment in FIG. 2. The coarse dose setting interactions between pegs 110 and surface 122a are analogous to features 18 and 31 for embodiment in FIG. 2.

Various views of beam 120 by creating sections of dose set dial 103 are shown in FIGS. 33A-33D. Surface 120a contacts plunger rod 102. A protrusion 120-1 on beam 120 helps axially constrain the peg 110 (and hence plunger rod 102) corresponding to the dose volume set for injection in the non-patient direction. At the end of dose delivery, the peg 110 corresponding to dose volume set and beam 140 of the end of dose drum 106 together are constrained between surface 120b and 121a. Immediately, prior to end of dose, the ramped feature on 120-1 enables beam 140, to deflect beam 120 from 'b' to 'a'. After the peg 110 corresponding to dose volume set has reach the end of dose position, the beam 120 relaxes back to position 'a' with surface 120b locking retraction of the plunger rod 102. This also creates an audible sound indicating end of dose. For all dose volumes except the lowest dose volume, a peg 110 corresponding to the volume immediately lower than the set volume is axially constrained between surfaces 120c and 122a at end of dose. Immediately prior to end of dose for all dose volume levels except the lowest settable volume, peg 110 also deflects beam 120 from 'd' to 'c'. Once end of dose is reached, the peg 110 escapes this beam 120 allowing it to relax back to position 'd', which also creates an audible indication of end of dose.

Cover 104, according to various embodiments, is illustrated in FIGS. 34A-34D. A cutout 126 on the cover 104 provides a window to only the dose marking 116 corresponding to the dose volume set by the user. The other markings are obscured by rest of the cover 104. Slot 127c provide user access to segment 114 of the dose set dial 103, which enables the user to rotate the dose set dial 103 in order to set a dose volume. In order to facilitate attachment to the housing 105, the cover 104 has a number of cylindrical posts 128*p*. Slot 129*c* along with identical slot 129*h* in the housing 105 allows placement and axial constraint for disc 107. An anti-rotation feature 112*a* plunger rod ramped slot 131*c* is used to engage tab 40 of clip 14 used in the attachment of a syringe 9 in a manner identical to the previously disclosed embodiments. 132*c* is use to engage a feature in the end of dose drum 106. The end of dose drum is visible through slot 133. Semicircular transverse slot 134*c* is also incorporated into the cover 104 to aid in attachment of a needle shielding apparatus.

Housing 105, according to various embodiments, is shown in FIGS. 35A-35E. Slot 129*h* is complementary to slot 129*c* to secure placement and axial constraint for disc 107. 131*h* is used to engage one of the tabs 40 of clip 14 used in the attachment of a syringe 9 similar to slot 131*c*. During assembly, the tabs 40 of clip 14 are axially aligned with axial keyways 135 until they reach slot 131*h* and 131*c*. The clip 14 is torqued until tight securing attaching syringe 9 to the housing 105. Slot 132*h* is identical and complimentary to slot 132*c* on cover 104. Semicircular transverse slot 134*h* can aid in attachment of a needle shielding apparatus. The housing 105 also includes two symmetric slots 136 diametrically across from each other to allow the user to inspect the drug 8 in syringe 9 prior to the injection. Features 136*a* and 136*b* are formed by intersection of slot 136 and axial keyways 135. Clicker beam 137 interacts with rectangular groove segments 124 on dose set dial 103. Surfaces 137*a* and 137*c* are angled such that they can transition in or out of rectangular groove segments 124 depending on direction of rotation of dose set dial 103. Each time, clicker beam 137 transitions into rectangular groove segment 124, the user hears an audible sound and user is provided with tactile feedback. When the clicker beam 137 is contained within a rectangular groove segment, a corresponding dose amount marking 116 is visible to the user through cutout 126 on cover 104. For example, when the clicker beam 137 is contained within rectangular groove segment 124*a*, '→' is visible through cutout 126. Also, when the clicker beam 137 is contained within rectangular groove segment 124*b*, '0.2' is visible through cutout 126. Also, in this example, when the clicker beam 137 is contained within rectangular groove segment 124*c*, '2.0' is visible through cutout 126. Clicker beam 138 is disposed within circular groove segment 123. Upon receipt for first time by the user, clicker beam 138 is placed with surface 138*a* contacting edge 123*a*; concurrently, the '→' marking 116 is visible through cut out 126. Surface 138*a* ensures that a rotational input to dose set dial 103 by the user can be applied only in the direction of ramp 125 to 123*b* by deflecting the clicker beam 138. Once surface 138*a* is at 123*b*, the '0.2' part of marking 116 is visible through cut out 126. Once at 123*b*, clicker beam returns to its undeflected state, and surface 138*a* prevents rotation of the dose set dial 103 in the direction of 125. The rotational angle between 123*a* and 123*b* is the same as rotational angle between '→' and '0.2' markings 116. Surface 138*b* hence prevents transition of the dose set dial 103 from '0.2' to '→'. After transitioning from '→' to '0.2', continued rotation of dose set dial 103 is allowed until surface 138*c* contacts 123*c*, at which time the '2.0' (maximum deliverable dose for illustrated embodiment) marking 116 is visible through cut out 126. The dose set dial 103 can be rotated in either direction except when clicker beam 138 is at 123*b* and 123*c*. The interaction between surfaces 138*c* and surface by edge 123*c* prevents transition from '2.0' to '→' markings 116 on the dose set dial 103.

The end of dose drum 106 is illustrated in FIGS. 36A-36D. It consists of two flexible beams 141 with hemispherical pegs that help it rotate within slot 132*c* and 132*h* of the cover 104 and housing 105 respectively. A colored band 139 is printed on the external cylindrical surface of end of dose drum 106; this band 139 provides the user with a visual end of dose indication and becomes visible to the user at end of dose through slot 133 on the cover 104. The inner diameter of the end of dose drum 106 defining cavity 117 is slightly larger than segment 115 on the dose set dial 103 and its outer diameter is smaller than the diameter of segment 114 of the dose set dial 103. The end of dose drum 106 is placed coaxial with dose set dial 103. A radially inward oriented beam 140 is disposed within in slot 121*s* of dose set dial 103 at the beginning of dose; this rotationally keys the end of dose drum 106 with the dose set dial 103. When the patient facing side of peg 110 corresponding to the dose volume set by the user axially advances towards 121*a* of the dose set dial 103 to deliver the dose, the beam 140 is advanced from slot 121*s* to slot 121*e*. At the end of dose, beam 140 is between peg 110 and surface 121*a*. This axial translation causes hemispherical pegs on beams 141 to be released from slot 132*c*, 132*h*, and causes the colored band 139 to be visible to the user at end of dose through slot 133 on the cover 104. This method of indicating end of dose to the user is the same irrespective of the volume injected. This providing uniformity in conveying information to the user. It possible to envision the end of dose drum 106 to alternatively be a fraction of a cylinder.

FIGS. 37A-37D illustrate disc 107, which can be placed in 129*c* and 129*h*. It includes a radially inward oriented protrusion 143, which is placed within slot 112*d* of the plunger rod 102. This protrusion 143 helps prevent rotation of plunger rod 102. X-ring 15 is placed around cylindrical feature 142. Upon assembly, plunger rod 102 is placed within cavity 117.

Two, optically clear window covers 108 shown in FIGS. 38A-38C are attached to slots 136. The window cover 108 is attached to housing 105 by first placing feature 143 into 136*a* of the housing 105, and then placing clip 142 into 136*b*, thereby locking it and covering slot 136.

Figure 39:
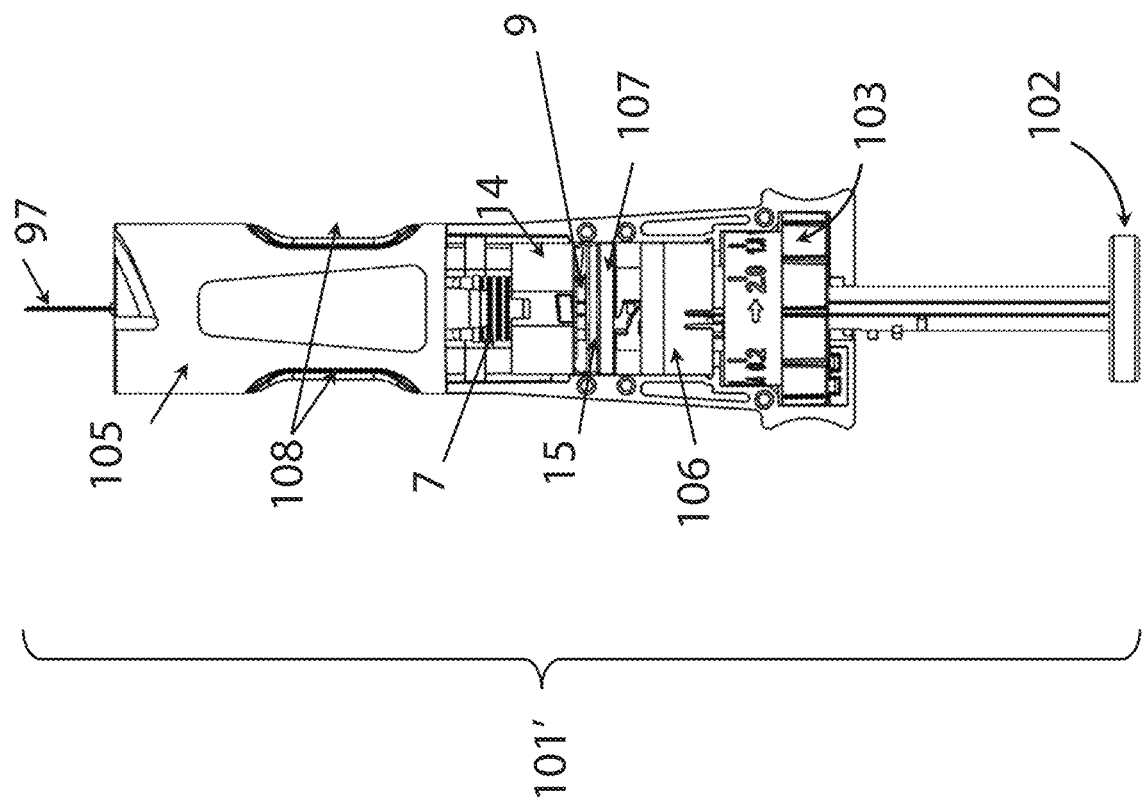
FIG. 39 illustrates a syringe, according to various embodiments.
Figures 40A, 40B, 40C, 40D, 40E, 40F, 40G:
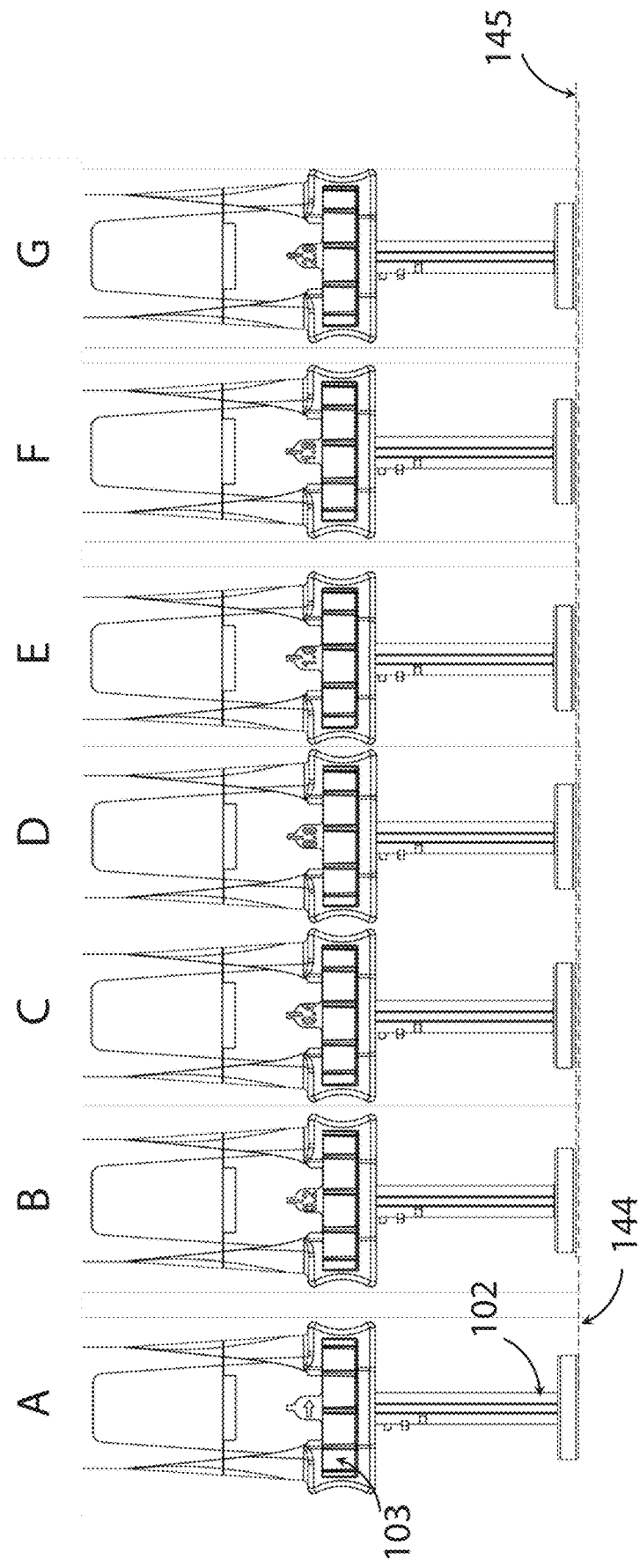
Figure 43B:
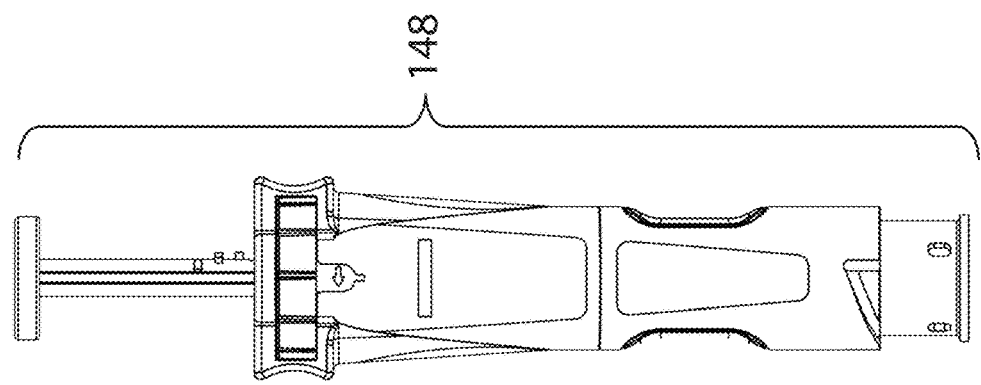
FIGS. 43A-43B illustrate a syringe with a needle shield, according to various embodiments.
Figure 43A:
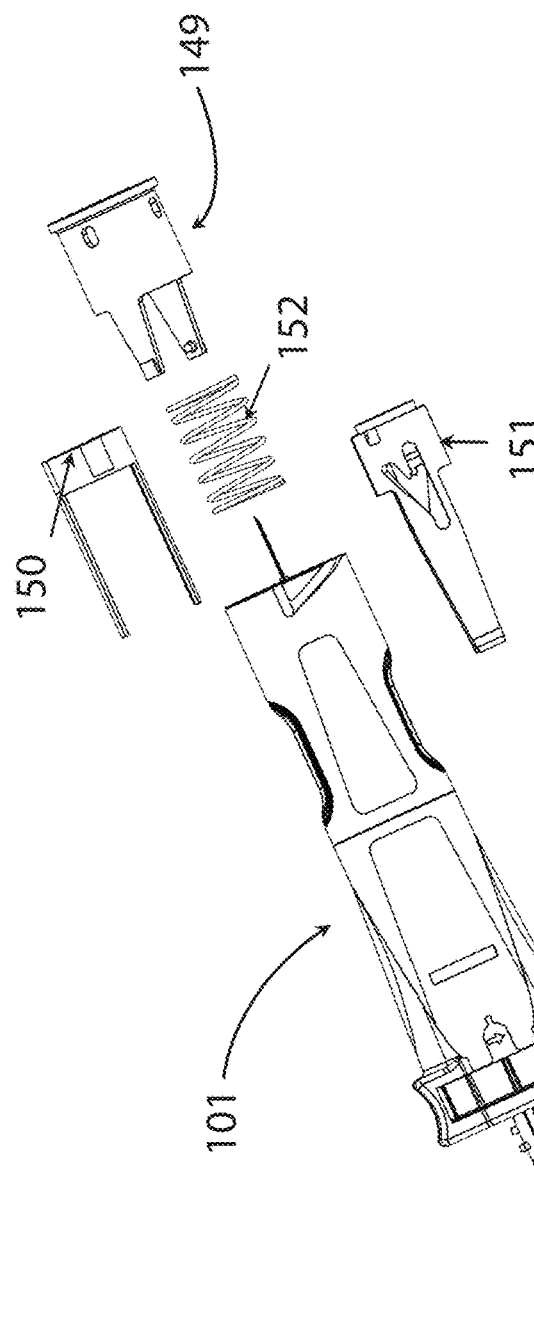

The assembled syringe 101 is shown without its cover 104 as 101' in FIG. 39, according to various embodiments.

Portion of external views of dose setting using embodiment 101 are shown in FIGS. 40A-40G, according to various embodiments. 'a' corresponds to view when the embodiment is received by the user. The axial position of plunger rod 102 is labelled 144. When dose set dial 103 is rotated by the user to get 'b' (0.2 ml), 'c' (0.4 ml), 'd' (0.8 ml), 'e' (1.0 ml), 'f' (1.8 ml) or 'g' (2.0 ml), the axial position of the plunger rod 102 changes to 145. However, this axial position 145 is the same irrespective of dose volume set for 'b', 'c', 'd', e' or 'f'. Axial translation from 144 to 145 is the fine resolution of plunger rod 102 travel followed by setting for coarser resolution of travel of plunger rod 102.

Relative positions of the plunger rod 102 and dose set dial 103 after initial translation facilitated by fine resolution travel is illustrated in FIGS. 41A-41F. Fine resolution travel is complete when surface 118*a* axially advances peg 109*a* to position shown in b'. B' corresponds to 0.2 milliliter dose volume start of dose in the illustrated embodiment. Upon immediate further rotation of dose set dial 103 as shown in c', peg 109*a* is placed behind largest inner diameter of segment 114, but at the same axial position as b'. Continued rotation of dose set dial 103 yields views d', e', f' and g', where the peg 109*a* is positioned at its axial position depicted in b' and c'.

Dose setting and dose delivery for 0.2 and 2.0 milliliter dose volumes are illustrated in FIGS. 42A-42E showing interaction between dose setting dial 103 and plunger rod 102. The position of dose set dial 103 relative to plunger rod 102 prior to dose setting is shown by 'a'. Once the dose set dial 103 is rotated to set a 0.2 milliliter dose volume (shown in 'b'), the plunger rod 102 advances from axial position 144 to position 145; this is the fine resolution travel that could help with overcoming plunger stopper 7 stiction in a controlled fashion. Concurrently, peg 110a on plunger rod 102 is longitudinally aligned with stop surface 121a. After the user has axially advanced the plunger rod 102 to administer the 0.2 milliliter set dose as shown by 'c', the axial position 146 of the plunger rod 102 is the end of dose position. Concurrent to this end of dose position 146, the peg 110a is in 121e. Between the patient facing side of peg 110a and stop surface 121a is beam 140 of the end of dose drum 106 (not shown here for sake of visualization clarity). 'd' depicts configuration when a 2.0 ml dose (maximum dose for illustrated embodiment) is set. The axial position 145 of plunger rod 102 at start of dose in 'd' is same as in 'b'. Peg 110c and peg 110b on the plunger rod are longitudinally aligned with dose set dial 103 stop surfaces 121a and 122a respectively. After the user has axially advanced the plunger rod 102 to administer the 2.0 milliliter set dose as shown by 'e', the axial position 147 of the plunger rod 102 is the end of dose position. Concurrent to this end of dose position 147, the peg 110c is in 121e. Between the patient facing side of peg 110c and stop surface 121a is beam 140 of the end of dose drum 106 (not shown here for sake of visualization clarity). Also, at this time, peg 110b is axially constrained within cavity 122 and is contacting surface 122a. Cavity 122 is vacant only in case of the lowest dose volume (0.2 milliliter in this illustrated example). For all other doses, cavity 122 axially and rotationally constrains the peg 110 on the plunger rod corresponding to the volume immediately lower level to the one set for injection.

It may be desirable in some applications to shield view of the needle prior to and after an injection. Embodiment 148 illustrates one such example where needle shield 149 obscures view of the injection needle 97. The needle shield 149 is guided into tracks 135 of the housing 105. Contained within needle shield 149 is the end of procedure indicator drum. When the needle shield 149 is pressed against the injection site to insert the obscured needle 97, the needle shield 149 upon retraction into the housing 105 rotates a slider 150, which contains a track to guide a feature on the needle shield 149. The slider 150 is axially constrained within slot 134c and 134h. After injection procedure is complete, spring 152 pushes the needle shield 149 to cover the needle 97, and axially locking the needle shield 149 due to a locking feature on the slider 150.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A plunger rod assembly for a syringe comprising:
   a main body;
   a plunger rod at least partially received in the main body and comprising a set of one or more protrusions; and
   a dosage setter operatively coupled to the plunger rod and comprising a rotatable body that comprises a set of one or more stops for engaging the set of one or more protrusions of the plunger rod depending on at least a rotational position of the set of one or more stops relative to the set of one or more protrusions, wherein a first rotational adjustment associated with the dosage setter is configured to set a first dosage increment by adjusting a relative axial position between the rotatable body and the plunger rod, and a second rotational adjustment associated with the dosage setting assembly is configured to set a second dosage increment that is larger than the first dosage increment by adjusting a relative rotational alignment between the set of one or more stops and the set of one or more protrusions.

2. The plunger rod assembly of claim 1, wherein the first rotational adjustment comprises a rotatable dial that engages the rotatable body and can rotate relative to the rotatable body to axially translate the rotatable body relative to the main body.

3. The plunger rod assembly of claim 2, wherein the rotatable dial comprises a thread that engages a thread of the rotatable body.

4. The plunger rod assembly of claim 1, wherein the second rotational adjustment comprises a dial for rotating the rotatable body.

5. The plunger rod assembly of claim 4, wherein the rotatable body can translate relative to the dial.

6. The plunger rod assembly of claim 4, wherein the rotatable body and the dial are fixed relative to one another.

7. The plunger rod assembly of claim 1, wherein the first rotational adjustment adjusts an axial position of the rotatable body relative to the main body.

8. The plunger rod assembly of claim 1, wherein the first rotational adjustment adjusts an axial position of the plunger rod relative to the main body.

9. The plunger rod assembly of claim 1, wherein the plunger rod is rotationally fixed.

10. The plunger rod assembly of claim 1, wherein the rotatable body is laterally offset relative to the plunger rod.

11. The plunger rod assembly of claim 1, wherein a rotational axis of the rotatable body intersects the plunger rod.

12. The plunger rod assembly of claim 1, wherein the set of one or more protrusions comprises a single protrusion and the set of one or more stops comprises a plurality of stops.

13. The plunger rod assembly of claim 1, wherein the set of one or more protrusions comprises a plurality of protrusions and the set of one or more stops comprises a single stop.

14. The plunger rod assembly of claim 1, wherein the first rotational adjustment comprises a slot in the rotatable body that receives a portion of the plunger rod, and the slot comprises a ramped surface that axially pushes the portion of the plunger rod received in the slot as the rotatable body rotates.

15. The plunger rod assembly of claim 14, wherein the set of one or more protrusions comprises a single protrusion and the portion of the plunger rod is the single protrusion.

16. The plunger rod assembly of claim 14, wherein the portion of the plunger rod can escape one circumferential end of the slot such that continued rotation of the rotatable body does not cause further axial translation of the plunger rod relative to the rotatable body.

17. A syringe comprising the plunger rod assembly of claim 1.

18. The syringe of claim 17, wherein the syringe is a prefilled syringe.

19. The syringe of claim 18, wherein the syringe is a single use syringe for injection of only one dose.

20. The syringe of claim 17, further comprising a retractable needle cover that is locked in an extended position at an end of dosage delivery.

21. A plunger rod assembly comprising:
a main body;
a plunger rod at least partially received in the main body and comprising one or more protrusions; and
a dosage setter that comprises:
a rotatable body that comprises one or more first stops that align with the one or more protrusions to define a dosage delivery end position of the plunger rod, wherein different alignments of the one or more first stops with the one or more first protrusions define different dosage settings, and
a second stop that engages the one or more protrusions of the plunger rod to define a dosage delivery start position of the plunger rod, wherein the dosage delivery start position of the plunger rod is the same for the different dosage settings.

22. The plunger rod assembly of claim 21, wherein the one or more protrusions of the plunger rod comprises a first protrusion, and wherein engagement between the first protrusion and the second stop defines the dosage delivery start position and engagement between the first protrusion and the one or more first stops defines the dosage delivery end position.

23. The plunger rod assembly of claim 21, wherein the one or more protrusions of the plunger rod comprises a first protrusion and a second protrusion, and wherein engagement between the first protrusion and the second stop defines the dosage delivery start position and engagement between the second protrusion and the one or more first stops defines the dosage delivery end position.

24. The plunger rod assembly of claim 21, wherein the second stop comprises a slot that receives a first protrusion of the one or more protrusions.

25. The plunger rod assembly of claim 24, wherein the slot comprises a ramped surface that pushes the first protrusion received in the slot as the rotatable body rotates in a rotation direction.

26. The plunger rod assembly of claim 25, wherein the first protrusion escapes the slot as the rotatable body continues to rotate in the rotation direction.

27. The plunger rod assembly of claim 21, wherein the dosage setter comprises a rotatable dial that engages the rotatable body and can rotate relative to the rotatable body to axially translate the rotatable body relative to the main body.

28. The plunger rod assembly of claim 27, wherein the rotatable dial comprises a thread that engages a thread of the rotatable body.

29. The plunger rod assembly of claim 21, wherein dosage setter comprises a dial for rotating the rotatable body.

30. The plunger rod assembly of claim 29, wherein the rotatable body can translate relative to the dial.

31. The plunger rod assembly of claim 29, wherein the rotatable body and the dial are fixed relative to one another.

32. The plunger rod assembly of claim 21, wherein the rotatable body can translate relative to the main body to define the dosage delivery end position of the plunger rod.

33. The plunger rod assembly of claim 32, wherein translation of the rotatable body provides a first resolution of dosage setting and rotation of the rotational body defines a second resolution of dosage setting.

34. The plunger rod assembly of claim 21, wherein the plunger rod is rotationally fixed.

35. The plunger rod assembly of claim 21, wherein the rotatable body is laterally offset relative to the plunger rod.

36. The plunger rod assembly of claim 21, wherein a rotational axis of the rotatable body intersect the plunger rod.

37. The plunger rod assembly of claim 21, wherein the rotatable body comprises the second stop.

38. The plunger rod assembly of claim 21, comprising a locking mechanism to rotationally constrain the dose setting dial at the dose delivery end position of the plunger rod.

* * * * *